(12) United States Patent
Sesardic et al.

(10) Patent No.: US 8,728,491 B2
(45) Date of Patent: *May 20, 2014

(54) TRANSCUTANEOUS DELIVERY OF THERAPEUTIC AGENTS

(75) Inventors: Dorothea Sesardic, London (GB); Blake Paterson, Baltimore, MD (US)

(73) Assignee: Alba Therapeutics Corporation, Baltimore, MD (US)

( * ) Notice: Subject to any disclaimer, the term of this patent is extended or adjusted under 35 U.S.C. 154(b) by 1059 days.

This patent is subject to a terminal disclaimer.

(21) Appl. No.: 12/599,430

(22) PCT Filed: May 7, 2008

(86) PCT No.: PCT/US2008/062894
§ 371 (c)(1),
(2), (4) Date: Jan. 11, 2011

(87) PCT Pub. No.: WO2009/023311
PCT Pub. Date: Feb. 19, 2009

(65) Prior Publication Data
US 2011/0142881 A1   Jun. 16, 2011

Related U.S. Application Data

(60) Provisional application No. 60/916,503, filed on May 7, 2007, provisional application No. 60/991,058, filed on Nov. 29, 2007.

(51) Int. Cl.
| | | |
|---|---|---|
| A61K 39/15 | (2006.01) | |
| A61K 38/08 | (2006.01) | |
| A61K 38/28 | (2006.01) | |
| A61K 39/00 | (2006.01) | |
| A61K 39/05 | (2006.01) | |
| A61K 39/10 | (2006.01) | |
| A61K 39/20 | (2006.01) | |
| A61K 39/08 | (2006.01) | |
| A61K 39/07 | (2006.01) | |
| A61K 39/12 | (2006.01) | |
| A61K 39/25 | (2006.01) | |
| A61K 38/00 | (2006.01) | |
| A61K 39/295 | (2006.01) | |
| C07K 4/04 | (2006.01) | |
| C07K 4/06 | (2006.01) | |

(52) U.S. Cl.
CPC ............... *A61K 39/08* (2013.01); *A61K 38/00* (2013.01); *A61K 39/295* (2013.01); *C07K 4/04* (2013.01); *C07K 4/06* (2013.01)
USPC ............... 424/261.1; 424/209.1; 424/184.1; 424/251.1; 424/254.1; 424/212.1; 424/219.1; 424/247.1; 424/246.1; 424/256.1; 424/232.1; 514/21.8; 514/21.7; 514/21.6; 514/5.9

(58) Field of Classification Search
None
See application file for complete search history.

(56) References Cited

U.S. PATENT DOCUMENTS

| | | | |
|---|---|---|---|
| 5,665,389 | A | 9/1997 | Fasano |
| 5,827,534 | A | 10/1998 | Fasano |
| 5,864,014 | A | 1/1999 | Fasano |
| 5,908,825 | A | 6/1999 | Fasano |
| 5,912,323 | A | 6/1999 | Fasano |
| 5,945,510 | A | 8/1999 | Fasano |
| 5,948,629 | A | 9/1999 | Fasano |
| 6,355,270 | B1 | 3/2002 | Ferrari et al. |
| 6,458,925 | B1 | 10/2002 | Fasano |
| 6,670,448 | B2 | 12/2003 | Fasano |
| 7,026,294 | B2 | 4/2006 | Fasano et al. |
| 8,198,233 | B2 | 6/2012 | Tamiz et al. |
| 2001/0036463 | A1* | 11/2001 | Compans et al. .......... 424/204.1 |
| 2002/0123047 | A1 | 9/2002 | Burnham |
| 2005/0059593 | A1* | 3/2005 | Fasano et al. ................ 514/12 |
| 2005/0266421 | A1 | 12/2005 | Bird et al. |
| 2006/0276403 | A1 | 12/2006 | Fasano et al. |

OTHER PUBLICATIONS

Berezowska et al. ("Dicarba Analogues of Cyclic Enkephalin Peptides H-Tyr-c[D-Cys-Gly-Phe-D(or L)-Cys]NH2 Retain High Opoid Activity", J. Med. Mar. 2007:50 (6): 1414-1417).*

* cited by examiner

*Primary Examiner* — James H Alstrum Acevedo
*Assistant Examiner* — Tara Martinez
(74) *Attorney, Agent, or Firm* — Cooley LLP

(57) ABSTRACT

The present invention provides materials and methods to facilitate the transcutaneous delivery of therapeutic agents. In some embodiments, agonists of tight junctions are used in compositions to facilitate the uptake of therapeutic agents from the skin. In a particular embodiment, the present invention provides immunogenic compositions comprising a tight junction agonist and an antigen. In a particular embodiment, the present invention provides vaccine compositions comprising a tight junction agonist and an antigen.

**11 Claims, 27 Drawing

FIGURE 2

AT1002 – Peptide

- Peptide dissolved in PBS
- Two doses (25µg and 75µg)
- Peptide received from Istituto Superiore di Sanita (ISS), Italy
- Peptide salt – TFA
- Peptide lot number – to be confirmed

FIGURE 9

Experiment 1 – Conclusions

- Promising results
- Significant increase in anti-tetanus IgG titers after immunization with TT + AT1002 vs. TT alone
- Significant increase in protective anti-tetanus IgG after immunization with TT + AT1002
- TT restimulation led to increased IL-6 production by spleen cells from mice immunized with TT + AT1002
- Cytokine data not matched by proliferation results no spleen cell proliferation observed (potential technical problem)

FIGURE 10

AT1002 – Peptide

- Peptide dissolved in dH$_2$O
- Larger dose range (0.03-300µg)
- Peptide salt – HCl
- **Peptide lot number –
    0604-290 (7/11/06)**

FIGURE 15

Experiment 2 – Conclusions

- Confirms findings of initial study and shows increased anti-tetanus response and protective antibody response induced by AT1002
- Dose-dependent effect of AT1002 for Ab response but not for cellular responses – but note high degree of variability within each group in this study
- Magnitude of response is reduced in comparison with experiment 1 – and fold increase over TT alone is slightly lower at comparable peptide dose
- Increased IL-6 and IFN-g production observed in spleen cells obtained from mice immunized with TT + AT1002 then restimulated with TT – although not at the highest peptide dose

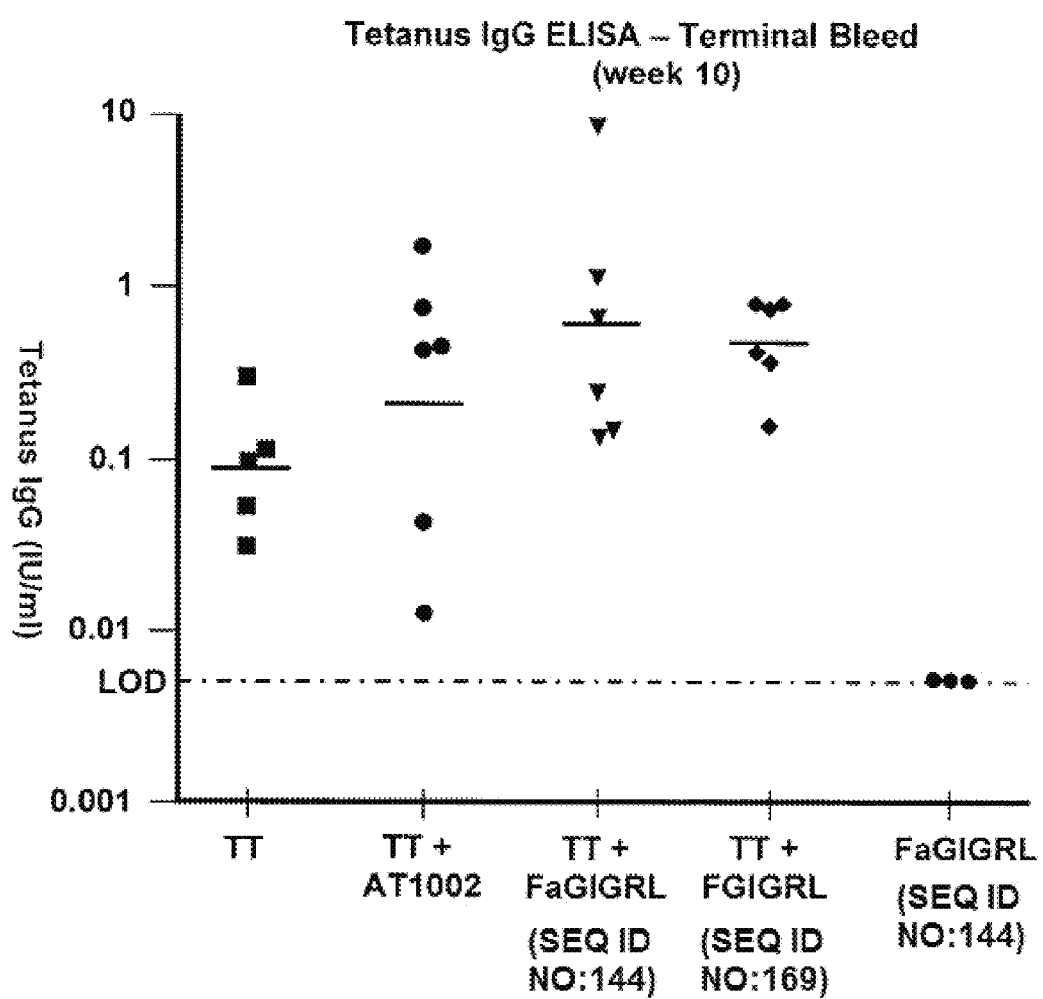

TRANSCUTANEOUS DELIVERY OF THERAPEUTIC AGENTS

STATEMENT CONCERNING RELATED APPLICATIONS

This application is the U.S. National Phase of International Application No. PCT/US08/62894, filed May 7, 2008, which claims priority to U.S. Provisional Application Ser. Nos. 60/916,503, and 60/991,058, filed May 7, 2007, and Nov. 29, 2007 respectively, and herein incorporated by reference in their entireties.

FIELD OF THE INVENTION

Description of the Text File Submitted Electronically

The contents of the text file submitted electronically herewith are incorporated herein by reference in their entirety: A computer readable format copy of the Sequence Listing (filename: ALBA_035_02US_SubSeqList_ST25.txt, date recorded: Feb. 25, 2011, file size 77 kilobytes).

The present invention provides materials and methods to facilitate the transcutaneous delivery of therapeutic agents. In some embodiments, agonists of biological pathways responsible for opening and closing tight junctions (e.g., tight junction agonists, zonulin agonists, ZOT agonists) are used in compositions to facilitate the uptake of therapeutic agents across the skin.

BACKGROUND OF THE INVENTION

The skin provides a protective barrier against deleterious materials present in the environment. Since the skin has a large surface area and is readily accessible, it has been used as the site of therapeutic delivery. Administration to the skin avoids the difficulties of other routes of administration, for example, the acid environment of the stomach encountered when oral administration is used or the pain associated with piercing the skin in parenteral administration. Numerous examples of transcutaneous delivery systems are known in the art, for example, U.S. Pat. Nos. 7,201,919, 7,097,853, and 6,946,144 all disclose various compositions and devices for transcutaneous administration of agents. There remains a need in the art for methods and compositions to improve the uptake of therapeutic agents from the skin. This need and others are met by the present invention.

SUMMARY OF THE INVENTION

In one embodiment, the present invention provides transcutaneous dosage compositions. Such compositions may comprise one or more therapeutic agents and a transcutaneous absorption enhancing amount of one or more tight junction agonists. As used herein, a "tight junction agonist" is a compound that mediates or facilitates or augments the physiological, transient opening of tight junctions, for example, the tight junctions between adjacent epithelial cells. An example of a tight junction agonist is zonula occludens toxin (ZOT), which is produced by *Vibrio cholerae*. A ZOT receptor agonist is a compound which is believed to mediate tight junction opening through the same receptor utilized by ZOT. In another embodiment, a tight junction agonist may comprise zonulin. In some embodiments, a tight junction agonist may comprise a peptide. In some embodiments, a tight junction agonist may be a fragment of ZOT and/or zonulin. In some embodiments, a tight junction agonist comprising a peptide may comprise the amino acid sequence FCIGRL (SEQ ID NO:1). A tight junction agonist comprising a peptide may comprise from about 6 to about 50 amino acids, from about 6 to about 25 amino acids, or from about 6 to about 10 amino acids.

A transcutaneous dosage composition according to the invention may comprise one or more therapeutic agents. Examples of suitable therapeutic agents include, but are not limited to, antibiotics, anti-inflammatories, analgesics, insulin and vaccines. Therapeutic agents for use in the invention may be of any type known to those of skill in the art, for example, small molecules, peptides, proteins, lipids, carbohydrates, and combinations thereof.

Transcutaneous dosage compositions of the invention may be liquids (e.g., aqueous solutions, emulsions, suspensions and the like). In some embodiments, a transcutaneous dosage composition may be an aqueous solution, for example, a saline solution.

Transcutaneous dosage compositions of the invention may also comprise one or more pharmaceutically acceptable excipients. Typical excipients that may be included in the compositions of the invention include, but are not limited to, sugars, salts, buffer salts, stabilizers, surfactants, polymers, preservatives and the like. Any pharmaceutically acceptable excipient known to those of skill in the art may be used.

An example of a transcutaneous dosage composition of the invention is an aqueous solution comprising a tight junction agonist comprising a peptide comprising the sequence FCIGRL (SEQ ID NO: 1) and also comprising at least one antigen.

The present invention also provides methods for treating animals (e.g., mammals including humans) by administering to the animal's skin a composition comprising one or more therapeutic agents and a transcutaneous absorption enhancing amount of one or more tight junction agonist. An example of a method of treating an animal is a method treating diabetes in an animal (e.g., a mammal such as a human) in need thereof, comprising administering to the animal's skin a composition comprising insulin and/or an insulin derivative and a transcutaneous absorption enhancing amount of one or more tight junction agonist. Compositions for use in methods of the invention may be liquids or aqueous solutions and may comprise one or more pharmaceutically acceptable excipients as described above.

In one embodiment, the present invention provides a method of inducing an immune response against an antigen in a mammal comprising administering a peptide having amino acid sequence FCIGRL (SEQ ID NO: 1) or a functional derivative thereof and the antigen to the skin of the animal, wherein the mammal raises the immune response against the antigen. Compositions for use in methods of inducing an immune response may further comprise one or more adjuvants (i.e., compounds that promote an enhanced immune response).

The present invention also provides immunogenic compositions. Such compositions may comprise one or more antigens and a transcutaneous absorption enhancing amount of one or more tight junction agonists. Examples of antigens that may be included in immunogenic compositions of the invention include, but are not limited to, measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens. Such compositions may further comprise one or more adjuvants. Immunogenic compositions of the invention may be liquids and may comprise one or more pharmaceutically acceptable excipients as described above.

In another embodiment, the present invention provides compositions and methods for the transcutaneous delivery of vaccines. Vaccines of the invention may be formulated for transcutaneous delivery. Such vaccines may comprise one or more antigens and a transcutaneous absorption enhancing amount of one or more tight junction agonists (e.g., a ZOT receptor agonist). Any antigen capable of inducing a protective immune response may be used in the vaccines of the invention. Examples of suitable antigens include, but are not limited to, measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens. Such vaccines may further comprise one or more adjuvants. Vaccines of the invention may be liquids and may comprise one or more pharmaceutically acceptable excipients as described above.

In particular embodiments the present invention provides:

A transcutaneous dosage composition, comprising: one or more therapeutic agents; and a transcutaneous absorption enhancing amount of one or more tight junction agonists.

A transcutaneous dosage composition, comprising: one or more therapeutic agents; and a transcutaneous absorption enhancing amount of one or more tight junction agonists, wherein at least one agonist comprises a peptide.

A transcutaneous dosage composition, comprising: one or more therapeutic agents; and a transcutaneous absorption enhancing amount of one or more tight junction agonists, wherein at least one agonist comprises a peptide comprising the sequence FCIGRL (SEQ ID NO: 1).

A transcutaneous dosage composition, comprising: one or more therapeutic agents; and a transcutaneous absorption enhancing amount of one or more tight junction agonists, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A transcutaneous dosage composition, comprising: one or more therapeutic agents; and a transcutaneous absorption enhancing amount of one or more tight junction agonists, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO: 19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A transcutaneous dosage composition, comprising: one or more therapeutic agents; and a transcutaneous absorption enhancing amount of one or more tight junction agonists, wherein at least one agonist comprises a peptide comprising from about 6 to about 10 amino acids.

A transcutaneous dosage composition, comprising: one or more therapeutic agents; and a transcutaneous absorption enhancing amount of one or more tight junction agonists, wherein at least one therapeutic agent is selected from the group consisting of antibiotics, anti-inflammatories, analgesics, insulin and vaccines.

A transcutaneous dosage composition, comprising: one or more therapeutic agents; and a transcutaneous absorption enhancing amount of one or more tight junction agonists, wherein at least one therapeutic agent is selected from the group consisting of small molecules, peptides, proteins, lipids, carbohydrates, and combinations thereof.

A transcutaneous dosage composition, comprising: one or more therapeutic agents; and a transcutaneous absorption enhancing amount of one or more tight junction agonists, wherein the composition is in aqueous solution.

A transcutaneous dosage composition, comprising: one or more therapeutic agents; and a transcutaneous absorption enhancing amount of one or more tight junction agonists, wherein the composition is in a saline solution.

A transcutaneous dosage composition, comprising: one or more therapeutic agents; and a transcutaneous absorption enhancing amount of one or more tight junction agonists, wherein the composition further comprises one or more pharmaceutically acceptable excipients.

A transcutaneous dosage composition, comprising: one or more therapeutic agents; and a transcutaneous absorption enhancing amount of one or more tight junction agonists, wherein the tight junction agonist is a peptide comprising the sequence FCIGRL (SEQ ID NO: 1) and the composition is in aqueous solution and the composition comprises one or more therapeutic agents selected from the group consisting of small molecules, peptides, proteins, lipids, and carbohydrates and combinations thereof.

A method of treating an animal, comprising: administering to the animal's skin a composition comprising one or more therapeutic agents and a transcutaneous absorption enhancing amount of a tight junction agonist.

A method of treating an animal, comprising: administering to the animal's skin a composition comprising one or more therapeutic agents and a transcutaneous absorption enhancing amount of a tight junction agonist, wherein the animal is a mammal.

A method of treating an animal, comprising: administering to the animal's skin a composition comprising one or more therapeutic agents and a transcutaneous absorption enhancing amount of a tight junction agonist, wherein the animal is a human.

A method of treating an animal, comprising: administering to the animal's skin a composition comprising one or more therapeutic agents and a transcutaneous absorption enhancing amount of a tight junction agonist, wherein at least one agonist comprises a peptide.

A method of treating an animal, comprising: administering to the animal's skin a composition comprising one or more therapeutic agents and a transcutaneous absorption enhancing amount of a tight junction agonist, wherein at least one agonist comprises a peptide comprising the sequence FCIGRL.

A method of treating an animal, comprising: administering to the animal's skin a composition comprising one or more therapeutic agents and a transcutaneous absorption enhancing amount of a tight junction agonist, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of treating an animal, comprising: administering to the animal's skin a composition comprising one or more therapeutic agents and a transcutaneous absorption enhancing amount of a tight junction agonist, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO: 19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of treating an animal, comprising: administering to the animal's skin a composition comprising one or more therapeutic agents and a transcutaneous absorption enhancing amount of a tight junction agonist, wherein at least one agonist comprises a peptide comprising from about 6 to about 10 amino acids.

A method of treating an animal, comprising: administering to the animal's skin a composition comprising one or more therapeutic agents and a transcutaneous absorption enhancing amount of a tight junction agonist, wherein at least one therapeutic agent is selected from the group consisting of antibiotics, anti-inflammatories, analgesics, insulin and vaccines.

A method of treating an animal, comprising: administering to the animal's skin a composition comprising one or more therapeutic agents and a transcutaneous absorption enhancing amount of a tight junction agonist, wherein at least one therapeutic agent is selected from the group consisting of small molecules, peptides, proteins, lipids, carbohydrates, and combinations thereof.

A method of treating an animal, comprising: administering to the animal's skin a composition comprising one or more therapeutic agents and a transcutaneous absorption enhancing amount of a tight junction agonist, wherein the composition is in aqueous solution.

A method of treating an animal, comprising: administering to the animal's skin a composition comprising one or more therapeutic agents and a transcutaneous absorption enhancing amount of a tight junction agonist, wherein the composition is in a saline solution.

A method of treating an animal, comprising: administering to the animal's skin a composition comprising one or more therapeutic agents and a transcutaneous absorption enhancing amount of a tight junction agonist, wherein the composition further comprises one or more pharmaceutically acceptable excipients.

A method of treating an animal, comprising: administering to the animal's skin a composition comprising one or more therapeutic agents and a transcutaneous absorption enhancing amount of a tight junction agonist, wherein the tight junction agonist is a peptide comprising the sequence FCIGRL (SEQ ID NO: 1) and the composition is in aqueous solution and the composition comprises one or more therapeutic agents selected from the group consisting of small molecules, peptides, proteins, lipids, carbohydrates, and combinations thereof.

A method of treating diabetes in an animal in need thereof, comprising: administering to the animal's skin a composition comprising insulin and/or a derivative thereof and a transcutaneous absorption enhancing amount of a tight junction agonist.

A method of treating diabetes in an animal in need thereof, comprising: administering to the animal's skin a composition comprising insulin and/or a derivative thereof and a transcutaneous absorption enhancing amount of a tight junction agonist, wherein the animal is a mammal.

A method of treating diabetes in an animal in need thereof, comprising: administering to the animal's skin a composition comprising insulin and/or a derivative thereof and a transcutaneous absorption enhancing amount of a tight junction agonist, wherein the animal is a human.

A method of treating diabetes in an animal in need thereof, comprising: administering to the animal's skin a composition comprising insulin and/or a derivative thereof and a transcutaneous absorption enhancing amount of a tight junction agonist, wherein at least one agonist comprises a peptide.

A method of treating diabetes in an animal in need thereof, comprising: administering to the animal's skin a composition comprising insulin and/or a derivative thereof and a transcutaneous absorption enhancing amount of a tight junction agonist, wherein at least one agonist comprises a peptide comprising the sequence FCIGRL (SEQ ID NO: 1).

A method of treating diabetes in an animal in need thereof, comprising: administering to the animal's skin a composition comprising insulin and/or a derivative thereof and a transcutaneous absorption enhancing amount of a tight junction agonist, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met;

Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of treating diabetes in an animal in need thereof, comprising: administering to the animal's skin a composition comprising insulin and/or a derivative thereof and a transcutaneous absorption enhancing amount of a tight junction agonist, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO: 19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of treating diabetes in an animal in need thereof, comprising: administering to the animal's skin a composition comprising insulin and/or a derivative thereof and a transcutaneous absorption enhancing amount of a tight junction agonist, wherein at least one agonist comprises a peptide comprising from about 6 to about 10 amino acids.

A method of treating diabetes in an animal in need thereof, comprising: administering to the animal's skin a composition comprising insulin and/or a derivative thereof and a transcutaneous absorption enhancing amount of a tight junction agonist, wherein the composition is in aqueous solution.

A method of treating diabetes in an animal in need thereof, comprising: administering to the animal's skin a composition comprising insulin and/or a derivative thereof and a transcutaneous absorption enhancing amount of a tight junction agonist, wherein the composition is in a saline solution.

A method of treating diabetes in an animal in need thereof, comprising: administering to the animal's skin a composition comprising insulin and/or a derivative thereof and a transcutaneous absorption enhancing amount of a tight junction agonist, wherein the composition further comprises one or more pharmaceutically acceptable excipients.

A method of treating diabetes in an animal in need thereof, comprising: administering to the animal's skin a composition comprising insulin and/or a derivative thereof and a transcutaneous absorption enhancing amount of a tight junction agonist, wherein the tight junction agonist is a peptide comprising the sequence FCIGRL (SEQ ID NO: 1) and the composition is in aqueous solution and the composition comprises human insulin and/or a pharmaceutically acceptable derivative thereof.

A method of inducing an immune response in an animal, comprising: administering to the animal's skin a composition comprising one or more antigens and a transcutaneous absorption enhancing amount of a tight junction agonist.

A method of inducing an immune response in an animal, comprising: administering to the animal's skin a composition comprising one or more antigens and a transcutaneous absorption enhancing amount of a tight junction agonist, further comprising administering an adjuvant.

A method of inducing an immune response in an animal, comprising: administering to the animal's skin a composition comprising one or more antigens and a transcutaneous absorption enhancing amount of a tight junction agonist, wherein the composition further comprises an adjuvant.

A method of inducing an immune response in an animal, comprising: administering to the animal's skin a composition comprising one or more antigens and a transcutaneous absorption enhancing amount of a tight junction agonist, wherein the animal is a mammal.

A method of inducing an immune response in an animal, comprising: administering to the animal's skin a composition comprising one or more antigens and a transcutaneous absorption enhancing amount of a tight junction agonist, wherein the animal is a human.

A method of inducing an immune response in an animal, comprising: administering to the animal's skin a composition comprising one or more antigens and a transcutaneous absorption enhancing amount of a tight junction agonist, wherein at least one agonist comprises a peptide.

A method of inducing an immune response in an animal, comprising: administering to the animal's skin a composition comprising one or more antigens and a transcutaneous absorption enhancing amount of a tight junction agonist, wherein at least one agonist comprises a peptide comprising the sequence FCIGRL (SEQ ID NO: 1).

A method of inducing an immune response in an animal, comprising: administering to the animal's skin a composition comprising one or more antigens and a transcutaneous absorption enhancing amount of a tight junction agonist, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of inducing an immune response in an animal, comprising: administering to the animal's skin a composition comprising one or more antigens and a transcutaneous absorption enhancing amount of a tight junction agonist, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO:

19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A method of inducing an immune response in an animal, comprising: administering to the animal's skin a composition comprising one or more antigens and a transcutaneous absorption enhancing amount of a tight junction agonist, wherein at least one agonist comprises a peptide comprising from about 6 to about 10 amino acids.

A method of inducing an immune response in an animal, comprising: administering to the animal's skin a composition comprising one or more antigens and a transcutaneous absorption enhancing amount of a tight junction agonist, wherein at least one antigen is selected from the group consisting of measles virus antigens; mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

A method of inducing an immune response in an animal, comprising: administering to the animal's skin a composition comprising one or more antigens and a transcutaneous absorption enhancing amount of a tight junction agonist, wherein the composition is in aqueous solution.

A method of inducing an immune response in an animal, comprising: administering to the animal's skin a composition comprising one or more antigens and a transcutaneous absorption enhancing amount of a tight junction agonist, wherein the composition is in a saline solution.

A method of inducing an immune response in an animal, comprising: administering to the animal's skin a composition comprising one or more antigens and a transcutaneous absorption enhancing amount of a tight junction agonist, wherein the composition further comprises one or more pharmaceutically acceptable excipients.

A method of inducing an immune response in an animal, comprising: administering to the animal's skin a composition comprising one or more antigens and a transcutaneous absorption enhancing amount of a tight junction agonist, wherein the tight junction agonist is a peptide comprising the sequence FCIGRL (SEQ ID NO: 1) and the composition is in aqueous solution and the composition comprises one or more antigens selected from the group consisting of measles virus antigens, mumps virus antigens, rubella virus antigens, *Corynebacteriun diphtheriae* antigens, *Bordetella pertussis* antigens, *Clostridium tetani* antigens. *Bacillus anthracis* antigens, *Haemophilus influenzae* antigens, smallpox virus antigens, and influenza virus antigens.

An immunogenic composition comprising one or more antigens and a transcutaneous absorption enhancing amount of a tight junction agonist.

An immunogenic composition comprising one or more antigens and a transcutaneous absorption enhancing amount of a tight junction agonist, wherein at least one antigen is selected from the group consisting of measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

An immunogenic composition comprising one or more antigens and a transcutaneous absorption enhancing amount of a tight junction agonist, wherein at least one agonist comprises a peptide.

An immunogenic composition comprising one or more antigens and a transcutaneous absorption enhancing amount of a tight junction agonist, wherein at least one agonist comprises a peptide comprising the sequence FCIGRL.

An immunogenic composition comprising one or more antigens and a transcutaneous absorption enhancing amount of a tight junction agonist, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5). Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro. Trp, and Met.

An immunogenic composition comprising one or more antigens and a transcutaneous absorption enhancing amount of a tight junction agonist, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO: 19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln: Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

An immunogenic composition comprising one or more antigens and a transcutaneous absorption enhancing amount of a tight junction agonist, wherein at least one agonist comprises a peptide comprising from about 6 to about 10 amino acids.

An immunogenic composition comprising one or more antigens and a transcutaneous absorption enhancing amount of a tight junction agonist, wherein the composition is in aqueous solution.

An immunogenic composition comprising one or more antigens and a transcutaneous absorption enhancing amount of a tight junction agonist, wherein the composition is in a saline solution.

An immunogenic composition comprising one or more antigens and a transcutaneous absorption enhancing amount of a tight junction agonist, wherein the composition further comprises one or more pharmaceutically acceptable excipients.

An immunogenic composition comprising one or more antigens and a transcutaneous absorption enhancing amount of a tight junction agonist, wherein the tight junction agonist is a peptide comprising the sequence FCIGRL (SEQ ID NO: 1) and the composition is in aqueous solution and the composition comprises at least one antigen selected from the group consisting of measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

A vaccine comprising one or more antigens and a transcutaneous absorption enhancing amount of a tight junction agonist.

A vaccine comprising one or more antigens and a transcutaneous absorption enhancing amount of a tight junction agonist, wherein at least one antigen is selected from the group consisting of measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

A vaccine comprising one or more antigens and a transcutaneous absorption enhancing amount of a tight junction agonist, wherein at least one agonist comprises a peptide.

A vaccine comprising one or more antigens and a transcutaneous absorption enhancing amount of a tight junction agonist, wherein at least one agonist comprises a peptide comprising the sequence FCIGRL (SEQ ID NO: 1).

A vaccine comprising one or more antigens and a transcutaneous absorption enhancing amount of a tight junction agonist, wherein at least one agonist comprises a peptide comprising a sequence selected from the group consisting of Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A vaccine comprising one or more antigens and a transcutaneous absorption enhancing amount of a tight junction agonist, wherein at least one agonist comprises a peptide comprising a sequence selected from the group consisting of Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys Ile Gly Arg Xaa6 (SEQ ID NO: 12), Phe Xaa2 Xaa3 Gly Arg Leu (SEQ ID NO: 13), Phe Xaa2 Ile Xaa4 Arg Leu (SEQ ID NO: 14), Phe Xaa2 Ile Gly Xaa5 Leu (SEQ ID NO: 15), Phe Xaa2 Ile Gly Arg Xaa6 (SEQ ID NO: 16), Phe Cys Xaa3 Xaa4 Arg Leu (SEQ ID NO: 17), Phe Cys Xaa3 Gly Xaa5 Leu (SEQ ID NO: 18), Phe Cys Xaa3 Gly Arg Xaa6 (SEQ ID NO: 19), Phe Cys Ile Xaa4 Xaa5 Leu (SEQ ID NO: 20), Phe Cys Ile Xaa4 Arg Xaa6 (SEQ ID NO: 21), and Phe Cys Ile Gly Xaa5 Xaa6 (SEQ ID NO: 22), wherein Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met.

A vaccine comprising one or more antigens and a transcutaneous absorption enhancing amount of a tight junction agonist, wherein at least one agonist comprises a peptide comprising from about 6 to about 15 amino acids.

A vaccine comprising one or more antigens and a transcutaneous absorption enhancing amount of a tight junction agonist, wherein the vaccine is an aqueous solution.

A vaccine comprising one or more antigens and a transcutaneous absorption enhancing amount of a tight junction agonist, wherein the vaccine is a saline solution.

A vaccine comprising one or more antigens and a transcutaneous absorption enhancing amount of a tight junction agonist, wherein the vaccine further comprises one or more pharmaceutically acceptable excipients.

A vaccine comprising one or more antigens and a transcutaneous absorption enhancing amount of a tight junction agonist, wherein the tight junction agonist is a peptide comprising the sequence FCIGRL (SEQ ID NO: 1) and the vaccine is an aqueous solution and the vaccine comprises at least one antigen selected from the group consisting of measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

BRIEF DESCRIPTION OF THE DRAWINGS

FIG. 1 describes the immunization protocol used in experiments 1 and 2. Animals were immunized with tetanus toxoid 02/126 (TT; 25 μg), cholera toxin (CT; 25 μg); and/or AT-1002 (25 μg or 75 μg). The ten week schedule that included a primary immunization, a first and second boost after 4 and 8 weeks respectively, and a test bleed at 6 weeks. Terminal bleed and spleen harvesting was carried out at ten weeks, and samples were processed as indicated.

FIG. 2 provides a summary of the characteristics of the AT1002 peptide (Phe-Cys-Ile-Gly-Arg-Leu, SEQ ID NO: 1) used in experiment 1.

FIG. 3 shows the immunization procedure as described in Example 1.

FIG. 4A shows experiment 1 tetanus IgG titers measured by ELISA in test bleeds taken from individual animal at week 6.

FIG. 4B shows experiment 1 tetanus IgG titers measured by ELISA in terminal bleeds taken from individual animal at week 10.

FIG. 5 shows a summary of the experiment 1 tetanus IgG titer measurements in different treatment groups 6 and 10 weeks after the primary immunization. Data represent the mean±s.e.m. (n=5 for each group). *$p<0.05$ vesus TT at the same time point. Peptide AT1002 significantly enhances the anti-tetanus response compared to tetanus toxoid alone. Higher dose of AT1002 peptide does not increaser the anti-tetanus response.

FIG. 6 shows the experiment 1 anti-tetanus IgG subclass titer measurements in treatment groups 10 weeks after the primary immunization. Data represent the mean±s.e.m. (n=5 for each group). No indication of a shift toward a Th1 response using AT1002 as an adjuvant. Serum IgA was also measured in the same samples, and no measurable level was observed in any of the groups in this experiment.

FIG. 7 shows the summarized proliferation of spleen cells isolated from immunized mice after restimulation with tetanus toxoid 02/126 (0-100 µg*ml) in experiment 1. Data represent the mean±s.e.m. (n=3 for each group), and they are expressed as a Stimulation Index relative to proliferation of cells grown in RPMI medium without restimulation. Results show a lack of proliferation in TT restimulated spleen cells from mice immunized with TT+AT1002 (25 µg) indicating a potential technical problem with this assay.

FIG. 8A shows the summarized production of Interleukin-6 (IL-6) by spleen cells isolated from immunized mice after restimulation with tetanus toxoid 02/126 (0-100 µg/ml) in experiment 1. Data represent the mean±s.e.m. (n=3 for each group). AT1002 does increase IL-6 production compared to groups immunized with toxoid (TT) alone.

FIG. 8B shows the summarized production of Interferon-gamma (IFN-γ) by spleen cells isolated from immunized mice after restimulation with tetanus toxoid 02/126 (0-100 µg/ml) in experiment 1. Data represent the mean±s.e.m. (n=3 for each group). AT1002 does not increase IFN-γ production compared to groups immunized with toxoid (TT) alone. Levels of IL-5 and IL-10 were also measured following restimulation, and AT1002 does not increase production of either one compared to groups immunized with toxoid (TT) alone.

FIG. 9 summarizes the conclusions from Experiment 1.

FIG. 10 provides a summary of the characteristics of the AT1002 peptide (FCIGRL, SEQ ID NO: 1) used in experiment 2.

Figure 12:
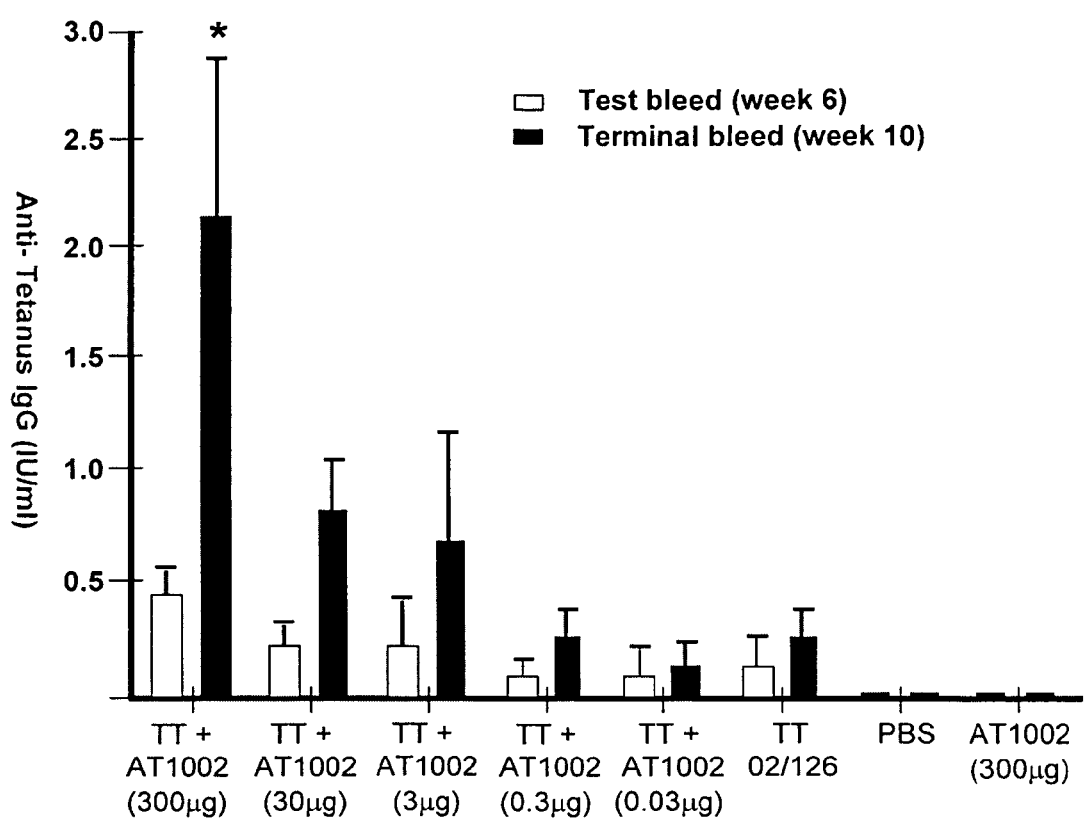

FIG. 12 shows a summary of the experiment 2 tetanus IgG titer measurements in different treatment groups 6 and 10 weeks after the primary immunization. Data represent the mean±s.e.m. (n=5 for each group). *p<0.05 vesus TT at the same time point. Peptide AT1002 significantly enhances the anti-tetanus response in a dose-dependent manner compared to tetanus toxoid alone. There was high variability within each group.

Figure 13:
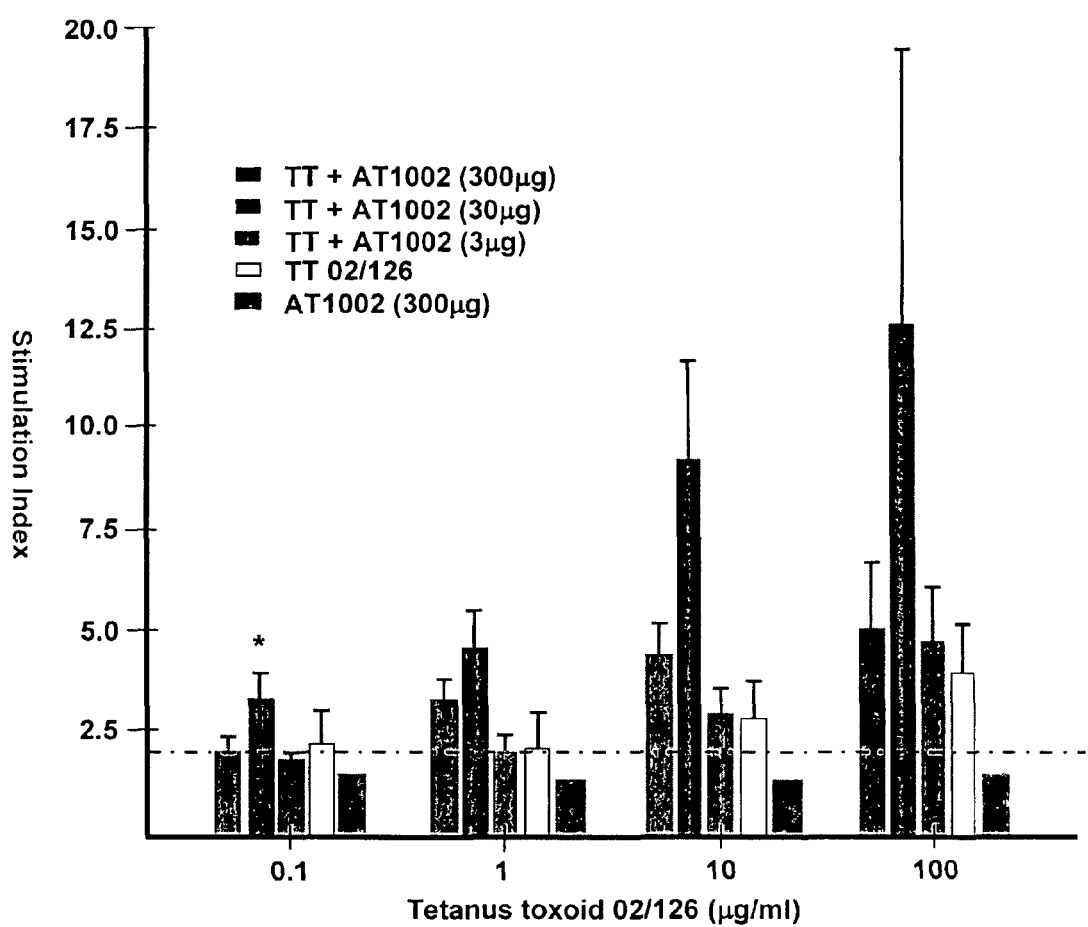

FIG. 13 shows the summarized proliferation of spleen cells isolated from immunized mice after restimulation with tetanus toxoid 02/126 (0-100 µg/ml) in experiment 2. Data represent the mean±s.e.m. (n=3 for each group), and they are expressed as a Stimulation Index relative to proliferation of cells grown in RPMI medium without restimulation. *p<0.05 versus AT 1002 3 µg and AT1002 300 µg at the same tetanus toxin dosage. Results show that AT1002 (30 µg) induces the strongest cell proliferation response on restimulation with immunizing antigen.

Figure 14A:
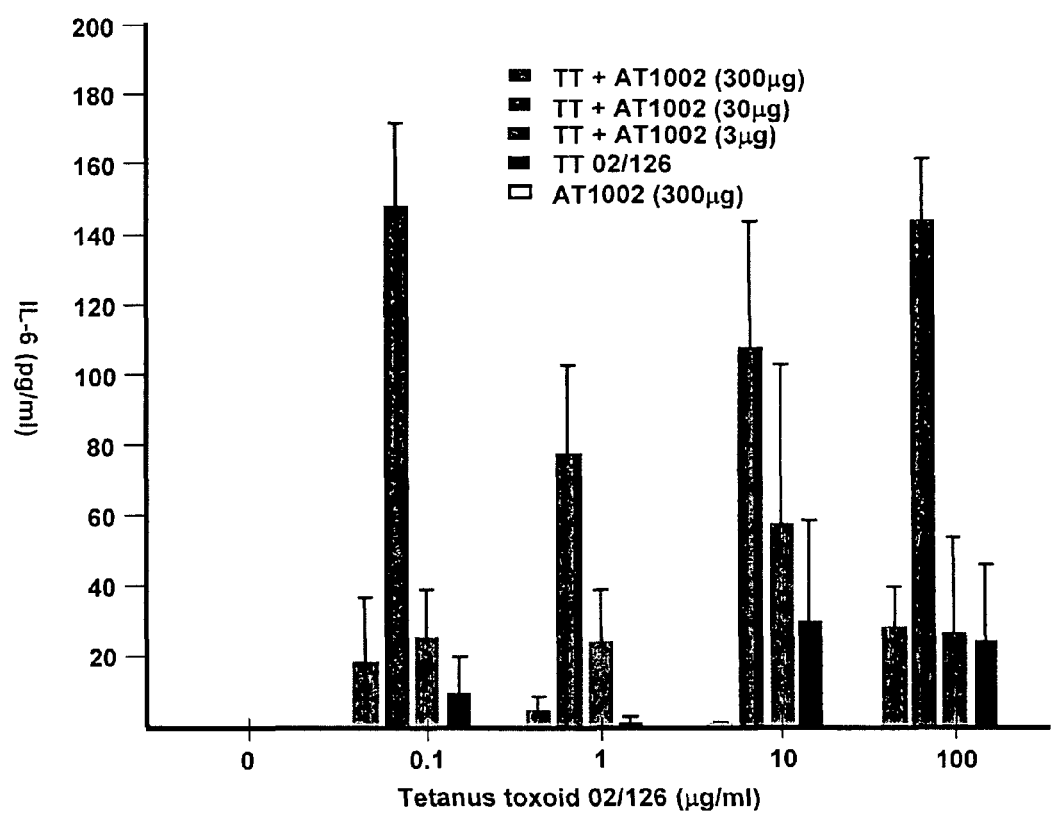

FIG. 14A shows the summarized production of Interleukin-6 (IL-6) by spleen cells isolated from immunized mice after restimulation with tetanus toxoid 02/126 (0-100 µg/ml) in experiment 2. Data represent the mean±s.e.m. (n=3 for each group). AT1002 does increase IL-6 production compared to groups immunized with toxoid (TT) alone.

Figure 14B:
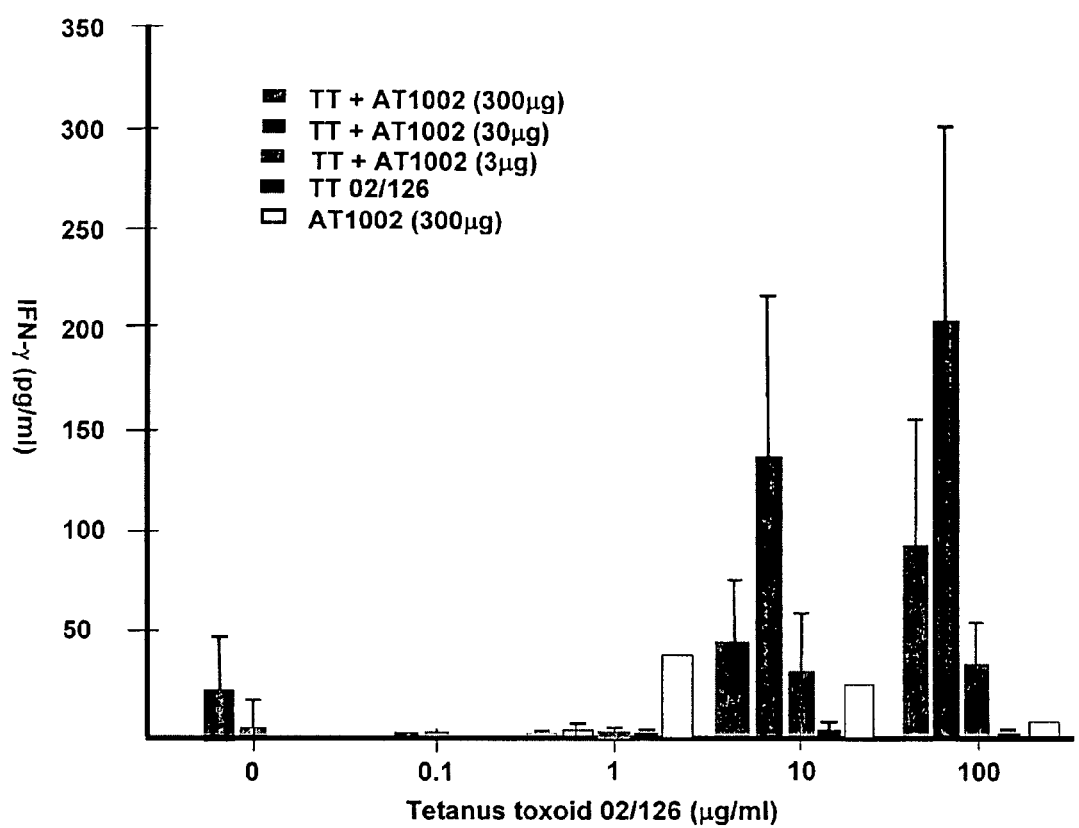

FIG. 14B shows the summarized production of Interferon-gamma (IFN-γ) by spleen cells isolated from immunized mice after restimulation with tetanus toxoid 02/126 (0-100 µg/ml) in experiment 2. Data represent the mean±s.e.m. (n=3 for each group).

FIG. 15 summarizes the conclusions derived from Experiment 2.

Figure 16:
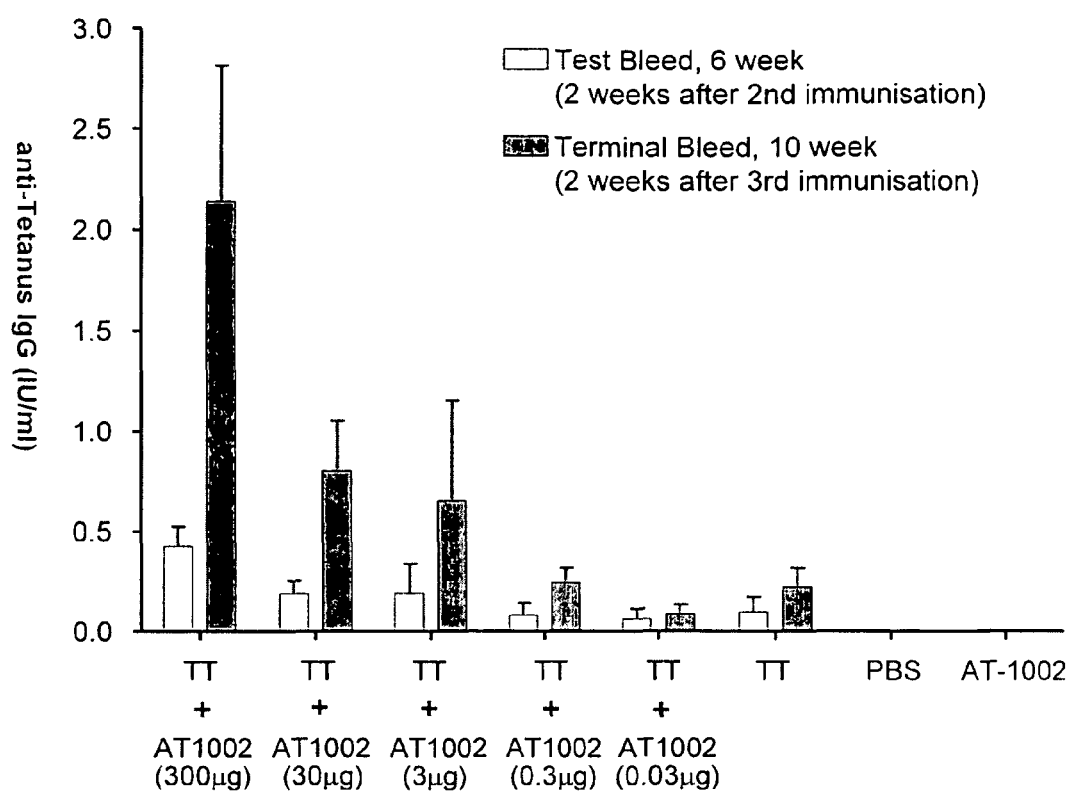

FIG. 16 shows anti-tetanus IgG titers after 6 and 10 weeks. Data represent the mean±SEM (n=5 per group).

Figure 17:
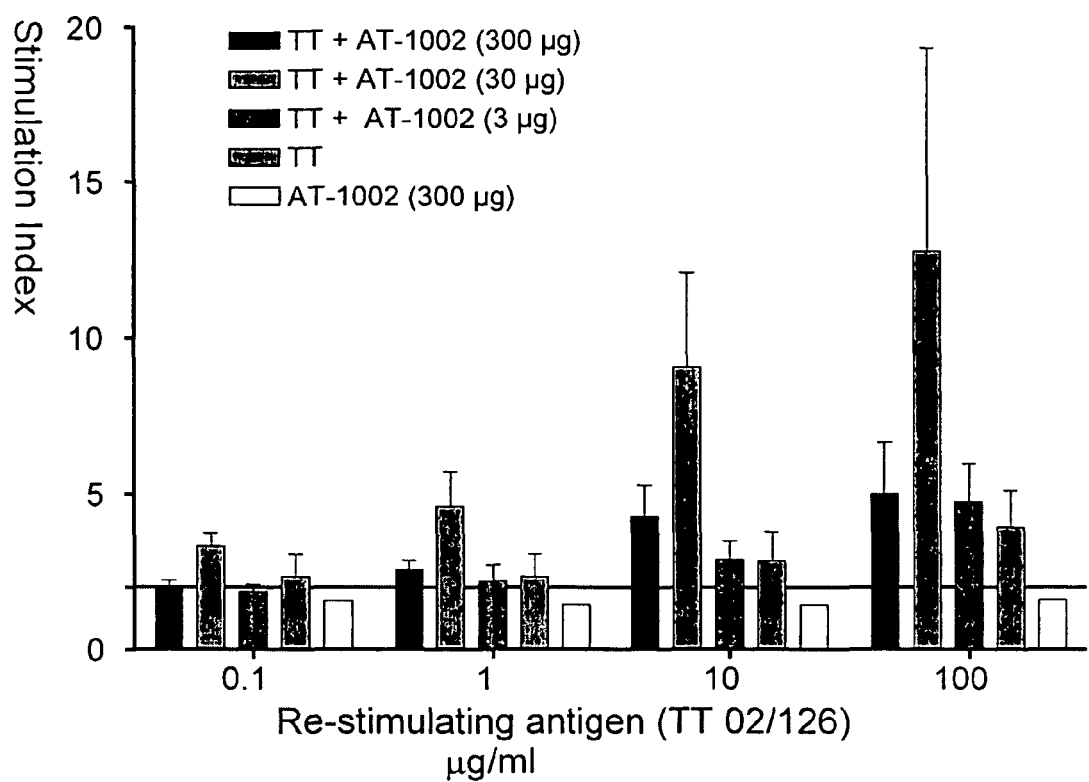

FIG. 17 shows spleen cell proliferation following re-stimulation with TT (0-100 µg/ml). Data represent the mean±SEM from three spleen cell cultures per group.

Figure 18A:
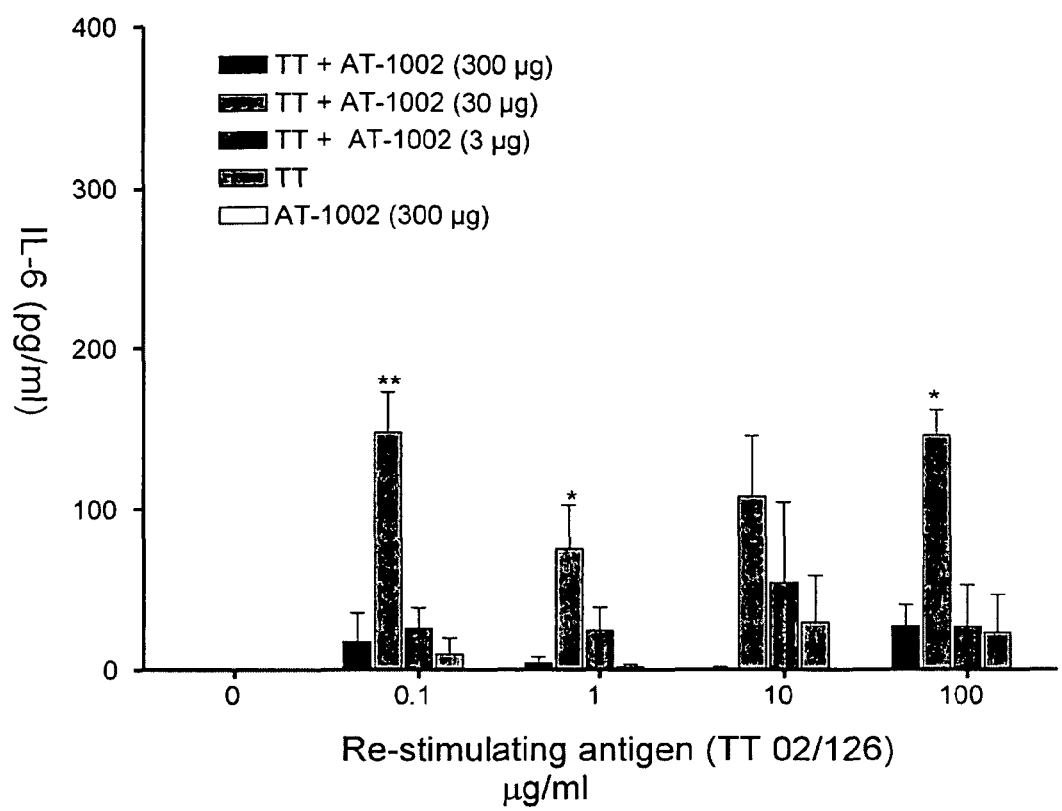

FIG. 18A shows production of IL-6 in splenocytes following re-stimulation with TT (0-100 µg/ml). Data represent the mean±SEM from three spleen cell cultures per group. *p<0.05, **p<0.01 vs TT alone.

Figure 18B:
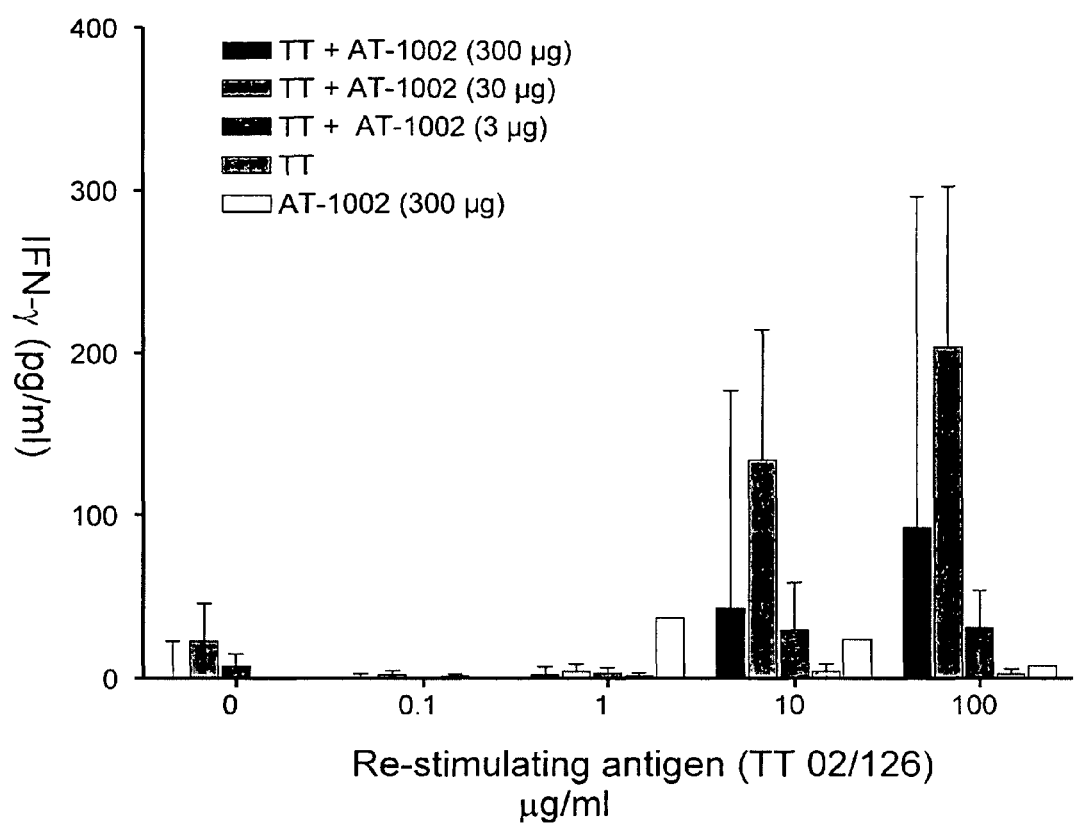

FIG. 18B shows production of IFN-γ in splenocytes following re-stimulation with TT (0-100 µg/ml). Data represent the mean±SEM from three spleen cell cultures per group.

Figure 19A:
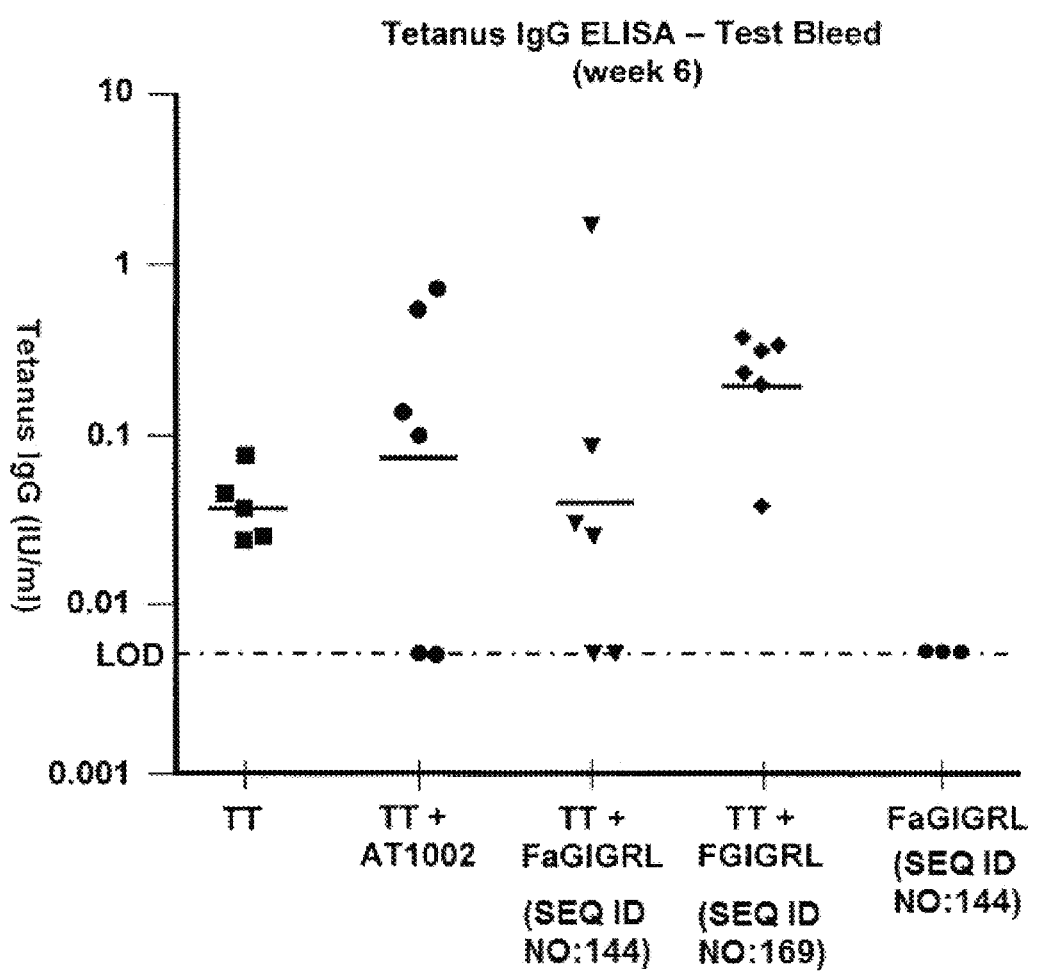

FIG. 19A shows experiment 3 tetanus IgG titers measured by ELISA in test bleeds taken from individual animals at week 6. Animals were immunized transcutaneously with tetanus toxoid 02/126 (25 µg) alone or in combination with peptide AT1002 (30 µg): Phe-Allyl(Gly)-Ile,Gly-Arg-Leu (FaGIGRL (SEQ ID NO: 144); 30 µg) or Phe-Gly-Ile-Gly-Arg-Leu (FGIGRL (SEQ ID NO:169); 30 µg). Mice received 3 doses of antigen τ. adjuvant at weeks 0, 4 and 8, animals were bled at weeks 6 and 10, and spleens were harvested at week 10 to measure proliferative responses on restimulatin with immunizing antigen (tetanus toxoid). Anti-tetanus IgG responses were measured by ELISA as described. n=6 for all immunization groups except: Tl' group n=5 (one animal excluded due to cut on abdomen after shaving); and FaGI-GRL (SEQ ID NO: 144) group n=3 (three animals excluded due to non-response to anesthesia).

FIG. 19B shows experiment 3 tetanus IgG titers measured by ELISA in terminal bleeds taken from individual animal at week 10. Animals were immunized and samples were gathered as described above (FIG. 21). Anti-tetanus IgG responses were measured by ELISA as described. n=6 for all immunization groups except: TT group n=5 (one animal excluded due to cut on abdomen after shaving); and FaGI-GRL (SEQ ID NO: 144) group n=3 (three animals excluded due to non-response to anesthesia).

Figure 20:
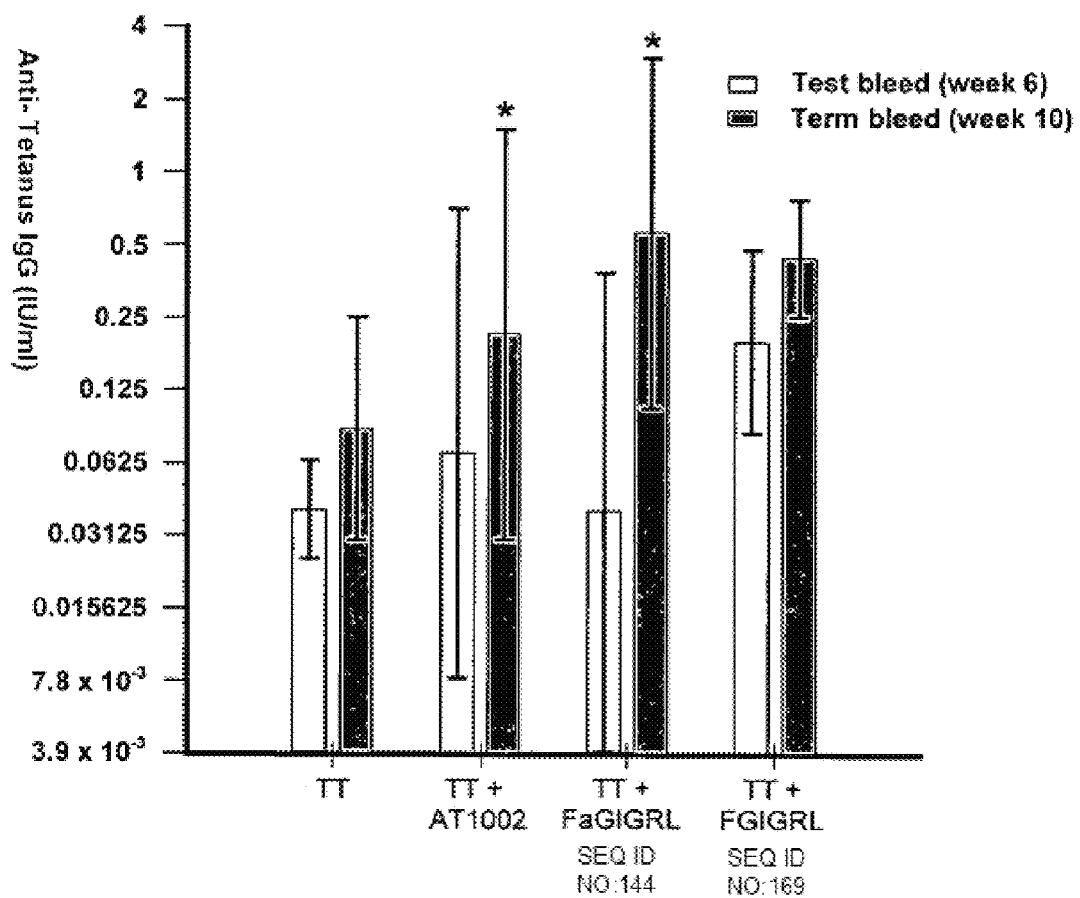

FIG. 20 shows a summary of the experiment 3 tetanus IgG titer measurements in different treatment groups 6 and 10 weeks after the primary immunization. Data represent the mean±s.e.m. (n=6 for each group except as noted in FIG. 21). *p<0.05 vesus test bleed titerin the same group (paired T-test). ANOVA analysis did not reveal any significant differences between immunization groups at either time point.

Figure 21:
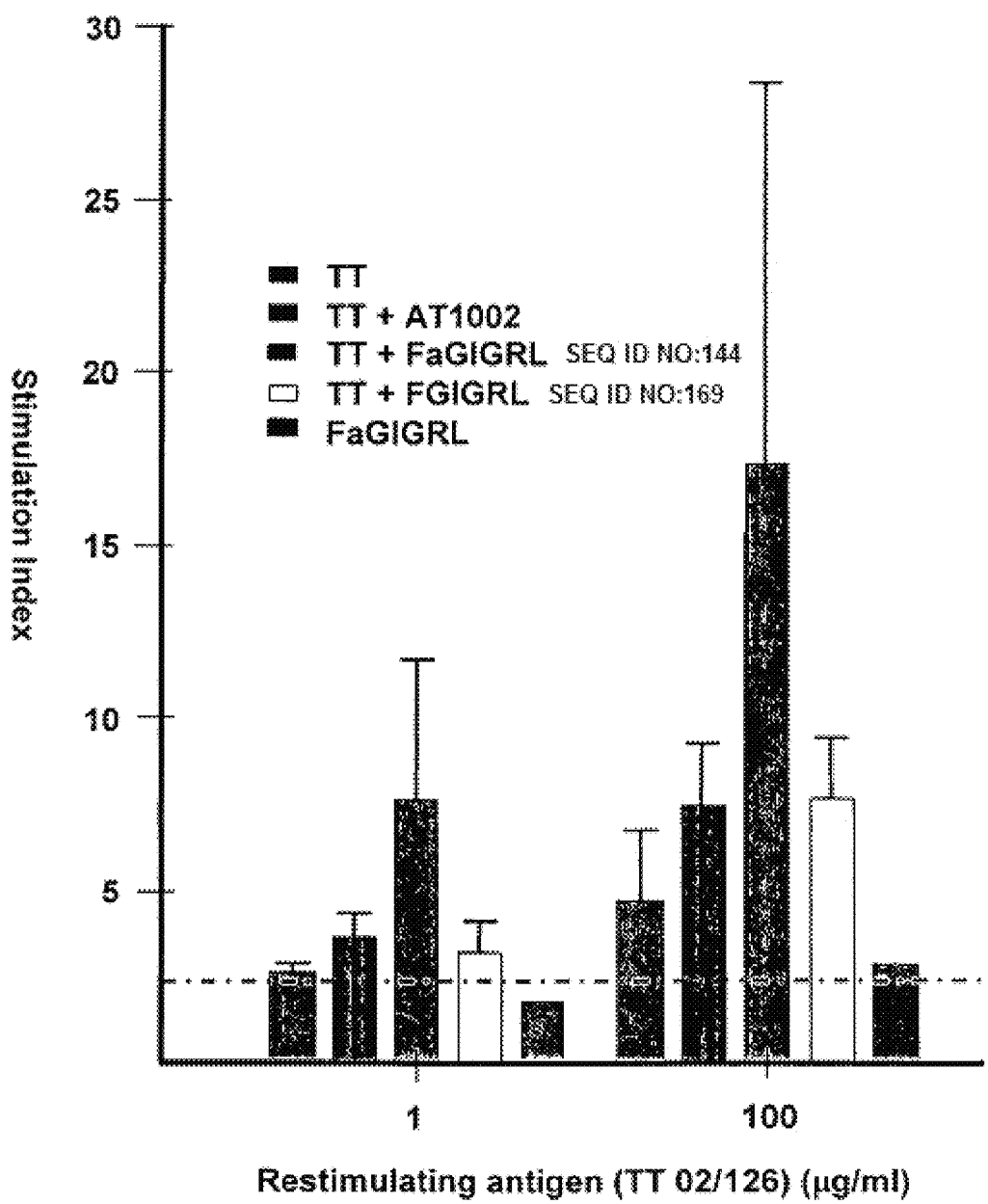

FIG. 21 shows the summarized proliferation of spleen cells isolated from immunized mice after restimulation with tetanus toxoid 02/126 (1 or 100 µg/ml) in experiment 3. Data represent the mean±s.e.m. (n=3 for each group), and they are expressed as a Stimulation Index relative to proliferation of cells grown in RPMI medium without restimulation.

DETAILED DESCRIPTION OF THE INVENTION

Definitions

As used herein, "a" or "an" may mean one or more. As used herein in the claim(s), when used in conjunction with the word "comprising", the words "a" or "an" may mean one or more than one. As used herein "another" may mean at least a second or more.

As used herein, "adjuvant" refers to a compound that induces, enhances, and/or augments an immune response to an antigen.

As used herein, "antigen" refers to any compound that can elicit an immune response, for example, which can elicit production of an antibody that specifically binds to the antigen.

As used herein, "immunogenic composition" refers to any composition comprising an antigen.

As used herein, "vaccine" refers to an immunogenic composition capable of eliciting a protective immune response when administered to a subject. A protective immune response is one that reduces the severity of disease when a vaccinated subject is contacted with the disease causing agent (e.g., virus, bacterium. etc). Examples of a reduction in severity of a disease include, prevention of disease, delay in onset of disease, decreased severity of symptoms, decreased morbidity, and delayed mortality.

As used herein, a "tight junction agonist" is a compound that mediates or facilitates or augments the physiological, transient opening of tight junctions. Tight junctions are structures that form a barrier between adjacent epithelial cells (Johnson and Quay, *Expert Opin Drug Deliv.* 2005 March; 2(2):281-98). An example of a tight junction agonist is zonula occludens toxin (ZOT), which is produced by *Vibrio cholerae*. A ZOT receptor agonist is a tight junction agonist which is believed to mediate tight junction opening through the same receptor utilized by ZOT. Tight junction agonists also include zonulin.

Tight Junction Agonists

Compositions of the invention typically comprise one or more tight junction agonists. A tight junction agonist facilitates absorption of a therapeutic agent. Further, the absorption occurs through the skin. Thus, a tight junction agonist as used herein is a compound that mediates the physiological, transient opening of tight junctions. In some embodiments, a tight junction agonist may operate by binding to the ZOT receptor, i.e., may be a ZOT receptor agonist.

In some embodiments, a tight junction agonist may comprise a peptide comprising the amino acid sequence FCIGRL (SEQ ID NO: 1) and/or functional derivatives of this sequence. Functional derivatives of peptide FCIGRL (SEQ ID NO: 1) include, for example, Xaa1 Cys Ile Gly Arg Leu (SEQ ID NO: 2), Phe Xaa2 Ile Gly Arg Leu (SEQ ID NO: 3), Phe Cys Xaa3 Gly Arg Leu (SEQ ID NO: 4), Phe Cys Ile Xaa4 Arg Leu (SEQ ID NO: 5), Phe Cys Ile Gly Xaa5 Leu (SEQ ID NO: 6), and Phe Cys Ile Gly Arg Xaa6 (SEQ ID NO: 7). Xaa1 is selected from the group consisting of Ala, Val, Leu, Ile, Pro, Trp, Tyr, and Met; Xaa2 is selected from the group consisting of Gly, Ser, Thr, Tyr, Asn, and Gln; Xaa3 is selected from the group consisting of Ala, Val, Leu, Ile, Pro, Trp, and Met; Xaa4 is selected from the group consisting of Gly, Ser, Thr, Tyr, Asn, Ala, and Gln; Xaa5 is selected from the group consisting of Lys and His; Xaa6 is selected from the group consisting of Ala, Val, Leu, Ile, Pro, Trp, and Met. In some embodiments, a tight junction agonist may consist of a peptide having the sequence FCIGRL (SEQ ID NO: 1) and/or functional derivatives of this sequence as described herein.

Further, functional derivatives of peptide FCIGRL (SEQ ID NO: 1) include: Xaa1 Xaa2 Ile Gly Arg Leu (SEQ ID NO: 8), Xaa1 Cys Xaa3 Gly Arg Leu (SEQ ID NO: 9), Xaa1 Cys Ile Xaa4 Arg Leu (SEQ ID NO: 10), Xaa1 Cys Ile Gly Xaa5 Leu (SEQ ID NO: 11), Xaa1 Cys He GIy Arg Xaa6 (SEQ ID NO: 12), Phe Xaa2 Xaa3 GIy Arg Leu (SEQ ID NO: 13), Phe Xaa2 He Xaa4 Arg Leu (SEQ ID NO: 14), Phe Xaa2 He GIy Xaa5 Leu (SEQ ID NO: 15). Phe Xaa2 He GIy Arg Xaa6 (SEQ ID NO: 16), Phe Cys Xaa3 Xaa4 Arg Leu (SEQ ID NO: 17), Phe Cys Xaa3 GIy Xaa5 Leu (SEQ ID NO: 18), Phe Cys Xaa3 GIy Arg Xaa6 (SEQ ID NO: 19), Phe Cys He Xaa4 Xaa5 Leu (SEQ ID NO: 20), Phe Cys He Xaa4 Arg Xaa6 (SEQ ID NO: 21), and Phe Cys He GIy Xaa5 Xaaó (SEQ ID NO: 22). Xaa1 is selected from the group consisting of Ala, VaI, Leu, He, Pro, Trp, Tyr, and Met; Xaa2 is selected from the group consisting of GIy, Ser. Thr, Tyr, Asn, and GIn; Xaa3 is selected from the group consisting of Ala, VaI, Leu. lie. Pro. Trp. and Met; Xaa4 is selected from the group consisting of GIy, Ser, Thr, Tyr, Asn, Ala, and GIn; Xaa5 is selected from the group consisting of Lys and His; Xaaó is selected from the group consisting of Ala, VaI, Leu, He, Pro, Trp, and Met.

In further specific embodiments, a tight junction agonist may comprise a peptide comprising an amino acid sequence selected from the group consisting of Cys Ile Gly Arg Leu (SEQ ID NO:23); Ile Gly Arg Leu (SEQ ID NO:24); Phe Cys Ile Gly Arg (SEQ ID NO:25); Phe Cys Ile Gly (SEQ ID NO:26): Ala Cys Ile Gly Arg Leu (SEQ ID NO:27); Phe Ala Ile Gly Arg Leu (SEQ ID NO:28); Phe Cys Ala Gly Arg Leu (SEQ ID NO:29); Phe Cys Ile Ala Arg Leu (SEQ ID NO:30); Phe Cys Ile Gly Ala Leu (SEQ ID NO:31); Phe Cys Ile Gly Arg Ala (SEQ ID NO:32); Phe Cys Ile Gly Arg Leu (SEQ ID NO:33); Pro Cys Ile Gly Arg Leu (SEQ ID NO:34); Gln Cys Ile Gly Arg Leu (SEQ ID NO:35); Gly Cys Ile Gly Arg Leu (SEQ ID NO:36); Thr Cys Ile Gly Arg Leu (SEQ ID NO:37); Ser Cys Ile Gly Arg Leu (SEQ ID NO:38); Sar Cys Ile Gly Arg Leu (SEQ ID NO:39); Asn Cys Ile Gly Arg Leu (SEQ ID NO:40); Arg Cys Ile Gly Arg Leu (SEQ ID NO:41); Cha Cys Ile Gly Arg Leu (SEQ ID NO:42); Aib Cys Ile Gly Arg Leu (SEQ ID NO:43); (t-Bu)Gly Cys Ile Gly Arg Leu (SEQ ID NO:44); Phe Thi Ile Gly Arg Leu (SEQ ID NO:45); Phe Hse Ile Gly Arg Leu (SEQ ID NO:46); Phe Thr Ile Gly Arg Leu (SEQ ID NO:47); Phe Abu Ile Gly Arg Leu (SEQ ID NO:48); Phe Ser Ile Gly Arg Leu (SEQ ID NO:49); Phe Met(O) Ile Gly Arg Leu (SEQ ID NO:50); Phe Met(O)2 Ile Gly Arg Leu (SEQ ID NO:51); Phe (d)Cys Ile Gly Arg Leu (SEQ ID NO:52): Phe Met Ile Gly Arg Leu (SEQ ID NO:53); Nva Cys Ile Gly Arg Leu (SEQ ID NO:54); Val Cys Ile Gly Arg Leu (SEQ ID NO:55); Hse Cys Ile Gly Arg Leu (SEQ ID NO:56); Phe Cys Ile Gly Arg Gly (SEQ ID NO:57); (d)Ala Cys Ile Gly Arg Gly (SEQ ID NO:58); Ala Cys Ile Gly Arg Gly (SEQ ID NO:59); Phe Cys Ile Gly Arg Gly (SEQ ID NO:60): (d)Phe Cys Ile Gly Arg Gly (SEQ ID NO:61); Phe Cys Ile Gly Arg Ser (SEQ ID NO:62); Phe Cys Ile Gly Arg Gln (SEQ ID NO:63); Phe Cys Ile Gly Arg (d)Leu (SEQ ID NO:64); Phe Cys Ile Gly Arg Lys (SEQ ID NO:65); Phe Cys Ile Gly Arg (d)Ala (SEQ ID NO:66); Phe Cys Ile Gly Arg Ile (SEQ ID NO:67); Phe Cys Ile Gly Are Gly (SEQ ID NO:68); Phe Cys Ile Gly Arg Nva (SEQ ID NO:69); Phe Cys Ile Gly Arg betaAla (SEQ ID NO:70); Phe Cys Ile Gly Arg Tle (SEQ ID NO:71); Phe Cys Ile Gly Arg Asp (SEQ ID NO:72); Phe Cys Ile Gly Arg MeAla (SEQ ID NO:73); Phe Cys Ile Gly Arg Abu (SEQ ID NO:74); Phe Cys Ile Gly Arg Glu (SEQ ID NO:75); Phe Cys Ile Gly Arg Aib (SEQ ID NO:76); Phe Cys Ile Gly Arg Phe (SEQ ID NO:77); Phe Cys Ile Gly Arg Asn (SEQ ID NO:78); Phe Cys Ile Gly Arg Pro (SEQ ID NO:79); Glu Cys Ile Gly Arg Leu (SEQ ID NO:80); Asp Cys Ile Gly Arg Leu (SEQ ID NO:81); Phe Cys Ile Gly Arg Cha (SEQ ID NO:82); Abu Cys Ile Gly Arg Leu (SEQ ID NO:83); Lys Cys Ile Gly Arg Leu (SEQ ID NO:84); Orn Cys Ile Gly Arg Leu (SEQ ID NO:85); Phe Cys Ile Gly Arg Leu Cys (SEQ ID NO:86); Leu Gly Gln Gln Gln Pro Phe Pro Pro Gin Gln Pro Tyr (SEQ ID NO:87); Phe Nva Ile Gly Arg Leu (SEQ ID NO:88); Phe Nle Ile Gly Arg Leu (SEQ ID NO:89); Pro Gly Pro Gly Arg Leu (SEQ ID NO:90); Phe Cys Ile Pro Gly Pro (SEQ ID NO:91); Phe Cys Leu Gly Arg Leu (SEQ ID NO:92); Phe Cys Ile Gly Gly Val Leu Val Gln Pro Gly (SEQ ID NO:93); Gly Cys Ile Gly Arg Gly (SEQ ID NO:94); Tyr Cys Ile Gly Arg Leu (SEQ ID NO:95); Phe Cys Ile Gly Cit Leu (SEQ ID NO:96); Ac Ala Cys Ile Gly Arg Leu (SEQ ID NO:97); Trp Cys Ile Gly Arg Leu (SEQ ID NO:98); Ac Ala Cys Ile Gly Arg Ser (SEQ ID NO:99); Ac Ala Cys Ile Gly Arg Ala (SEQ ID NO:100); Phe(4-NO2) Cys Ile Gly Arg Leu (SEQ ID NO:101); Phe(4-Cl) Cys Ile Gly Arg Leu (SEQ ID NO:102); Phe Cys Ile Gly Arg Phe(4-Cl) (SEQ ID NO:103); Phe Cys Ile Gly Arg Phe (4-NO2) (SEQ ID NO:104); Ac Phe Cys Ile Gly Arg Phe (SEQ ID NO:105); Tic Cys Ile Gly Arg Leu (SEQ ID NO:106); Ser Leu Ile Gly Arg Leu (SEQ ID NO:107); Leu Arg Gly Ile Cys Phe (SEQ ID NO:108); Leu Arg Gly Ile (d)Cys Phe (SEQ ID NO:109); (d)Leu Arg Gly Ile Cys Phe (SEQ ID NO:110); Leu (d)Arg Gly Ile Cys Phe (SEQ ID NO:111); Phe Cys Ile Gly (d)Arg Leu (SEQ ID NO:112); Phe Cys Ile(nMe) Gly Arg Leu (SEQ ID NO:113); Phe Cys Ile Gly Arg Thi (SEQ ID NO:114); Thi Cys Ile Gly Arg Leu (SEQ ID NO:115); (d)Leu (d)Arg Gly (d)Ile (d)Cys (d)Phe (SEQ ID NO:116); (d)Phe (d)Cys Ile Gly (d)Arg (d)Leu (SEQ ID NO:117); (d)Phe (d)Cys (d)Ile Gly Arg (d)Leu (SEQ ID NO:118); Phe Cys (d)Ile Gly Arg Leu (SEQ ID NO:119); Phe (d)Cys (d)Ile Gly (d)Arg (d)Leu (SEQ ID NO:120); (d)Phe Cys (d)Ile Gly (d)Arg (d)Leu (SEQ ID NO:121); Leu Arg Gly Ile Cys (d)Phe (SEQ ID NO:122); (d)Leu (d)Arg Gly (d)Ile Cys (d)Phe (SEQ ID NO:123); Leu (d)Arg Gly (d)Ile (d)Cys (d)Phe (SEQ ID NO:124); Leu Arg Gly (d)Ile Cys Phe (SEQ ID NO:125); (d)Phe (d)Cys (d)Ile Gly (d)Arg Leu (SEQ ID NO:126); (d)Leu (d)Arg Gly Ile (d)Cys (d)Phe (SEQ ID NO:127); (d)Leu Arg Gly (d)Ile (d)Cys (d)Phe (SEQ ID NO:128); (d)Leu (d)Arg Gly (d)Ile (d)Cys Phe (SEQ ID NO:129); Ac Phe Hse Ile Gly Arg Ala (SEQ ID NO:130); Ac Phe Hse Ile Gly Arg Ser (SEQ ID NO:131); Ac Phe Hse Ile Gly Arg Phe (SEQ ID NO:132); Phe Cys Ile Gly Arg Tic (SEQ ID NO:133); Phe Hse Ile Gly Arg Phe (SEQ ID NO:134); Phe Cys(S-benzyl) Ile Gly Arg Leu (SEQ ID NO:135); Phe Cys (t-buthiol) Ile Gly Arg Leu (SEQ ID NO:136); Phe Leu Ile Gly Arg Leu (SEQ ID NO:137); Phe Phe Leu Ile Gly Arg Leu (SEQ ID NO:138); Phe Phe Ile Gly Arg Leu (SEQ ID NO:139); Phe Phg Ile Gly Arg Leu (SEQ ID NO:140); Phe Pro Ile Gly Arg Leu (SEQ ID NO:141); Phe (d)Val Ile Gly Arg Leu (SEQ ID NO:142); Phe Cha Ile Gly Arg Leu (SEQ ID NO:143); Phe Allyl(Gly) Ile Gly Are Leu (SEQ ID NO:144); Phe tBu(Gly) Ile Gly Arg Leu (SEQ ID NO:145); Phe Cys Ala Gly (SEQ ID NO:146); Phe Cys Gly Gly (SEQ ID NO:147); Phe Trp Ile Gly Arg Leu (SEQ ID NO:148); Phe His Ile Gly Arg Leu (SEQ ID NO:149); Phe Pro Ile Gly Arg Leu (SEQ ID NO:150); Phe Asp Ile Gly Arg Leu (SEQ ID NO:151); Phe Dab Ile Gly Arg Leu (SEQ ID NO:152); Phe (d)Cys Ile Gly (d)Arg Leu (SEQ ID NO:153); (d)Leu Arg Gly Ile Cys Phe (SEQ ID NO:154); (d)Leu (d)Arg Gly Ile Cys Phe (SEQ ID NO:155); (d)Leu (d)Arg Gly Ile Cys (d)Phe (SEQ ID NO:156); (d)Leu (d)Arg Gly Ile (d)Cys Phe (SEQ ID NO:157); Gly Phe Cys Ile Gly Arg Leu (SEQ ID NO:158); Phe Leu Ile Gly Arg Leu (SEQ ID NO:159); Ac Phe Cys Ile Gly Arg Leu (SEQ ID NO:160); Phe Phe Ile Gly Arg Leu (SEQ ID NO:161); Phe (cyclopropane)Pro Ile Gly Arg Leu (SEQ ID NO162:); Phe Dpr Ile Gly Arg Leu (SEQ ID NO:163); Phe Pen(Acm) Ile Gly Arg Leu (SEQ ID NO:164); Leu Arg Gly Gly Arg Leu (SEQ ID NO:165); (d)Phe Cys Ile Gly Arg Leu (SEQ ID NO:166); (d)Phe (d)Cys (d)Ile Gly (d)Arg (d)Leu (SEQ ID NO:167); Phe Arg Ile Gly Arg Leu (SEQ ID NO:168); Phe Gly Ile Gly Arg Leu (SEQ ID NO:169); Phe Gln Ile Gly Arg Leu (SEQ ID NO:170); Phe Glu Ile Gly Arg Eeu (SEQ ID NO:171); Phe Lys Ile Gly Arg Leu (SEQ ID NO:172); Phe Asn Ile Gly Arg Leu (SEQ ID NO:173); Phe Tyr Ile Gly Arg Leu (SEQ ID NO:174); Phe Leu Ile Gly Arg Leu (SEQ ID NO:175); Phe Val Ile Gly Arg Leu (SEQ ID NO:176); Phe Ile Ile Gly Arg Leu (SEQ ID NO:177); Phe Hcy Ile Gly Arg Leu (SEQ ID NO:178); Ser Leu Ile Gly Arg Leu (SEQ ID NO:179); Phe Cys Ala Gly Met Ser (SEQ ID NO:180); Phe Cys Val Gly Met Ser (SEQ ID NO:181); Phe (2-pyridiyl)Ala Ile Gly Arg Leu (SEQ ID NO:182); Phe Leu (d)Ile Gly Arg Leu (SEQ ID NO:183); Ac Phe Leu Ile Gly Arg Leu (SEQ ID NO:184); Phe (d)Leu Ile Gly Arg Leu (SEQ ID NO:185); Leu Arg Gly (d)Ile Leu Phe (SEQ ID NO:186); Phe Abu(dimer) Ile Gly Arg Leu (SEQ ID NO:187); Phe (Dehydro)Leu Ile Gly Arg Leu (SEQ ID NO:188); Leu Arg Gly Ile Leu Phe (SEQ ID NO:189); Ac Phe Hse Ile Gly Arg (SEQ ID NO:190); Phe Hse (d)Ile Gly Arg (SEQ ID NO:191); Ac Phe Hse Ile Gly Arg Leu (SEQ ID NO:192); Phe Leu Ile Gly Arg (SEQ ID NO:193); Phe Hse (d)Ile Gly Arg Leu (SEQ ID NO:194); Phe (4-CN) Phe Ile Gly Arg Leu (SEQ ID NO:195); Phe (3-Me) Phe Ile Gly Arg Leu (SEQ ID NO:196); Phe Cyclopropyl(Ala) Ile Gly Arg Leu (SEQ ID NO:197); Phe Allyl(Gly) Ile Gly Arg (SEQ ID NO:198); Phe (d)Allyl(Gly) Ile Gly Arg (SEQ ID NO:199); Phe Pra Ile Gly Arg (SEQ ID NO:200); Phe Allyl(Gly) Ile Thr Arg Leu (SEQ ID NO:201); Phe Allyl(Gly) Ile Leu Arg Leu (SEQ ID NO:202); Phe Allyl(Gly) Ile Ile Arg Leu (SEQ ID NO:203); Phe Allyl(Gly) Ile Ala Arg Leu (SEQ ID NO:204); Phe Allyl(Gly) Ile Pro Arg Leu (SEQ ID NO:205); Phe Allyl (Gly) Pro Gly Arg Leu (SEQ ID NO:206); Phe Allyl(Gly) Phe Gly Arg Leu (SEQ ID NO:207); Phe Allyl(Gly) Thr Gly Arg Leu (SEQ ID NO:208); Phe Allyl(Gly) Leu Gly Arg Leu (SEQ ID NO:209); Phe Allyl(Gly) Ser Gly Arg Leu (SEQ ID NO:210); Phe Allyl(Gly) Phe Gly Arg Leu (SEQ ID NO:211); Phe Allyl(Gly) Val Gly Arg Eeu (SEQ ID NO:212); Phe Allyl(Gly) Gly Gly Arg Leu (SEQ ID NO:213); Phe Allyl (Gly) Ala Gly Arg Leu (SEQ ID NO:214); Met Allyl(Gly) Ile Gly Arg Leu (SEQ ID NO:215); Gln Allyl(Gly) Ile Gly Arg Leu (SEQ ID NO:216); Leu Allyl(Gly) Ile Gly Arg Eeu (SEQ ID NO:217); Ser Allyl(Gly) Ile Gly Arg Leu (SEQ ID NO:218); Thr Allyl(Gly) Ile Gly Arg Leu (SEQ ID NO:219); Glu Allyl(Gly) Ile Gly Arg Leu (SEQ ID NO:220); Val Allyl (Gly) Ile Gly Arg Leu (SEQ ID NO:221); Tyr Allyl(Gly) Ile Gly Arg Leu (SEQ ID NO:222); Gly Allyl(Gly) Ile Gly Arg Leu (SEQ ID NO:223); Asp Allyl(Gly) Ile Gly Arg Leu (SEQ ID NO:224); Trp Allyl(Gly) Ile Gly Arg Leu (SEQ ID NO:225); Lys Allyl(Gly) Ile Gly Arg Leu (SEQ ID NO:226); Ala Allyl(Gly) Ile Gly Arg Leu (SEQ ID NO:227); His Allyl (Gly) Ile Gly Arg Leu (SEQ ID NO:228); Pro Allyl(Gly) Ile Gly Arg Eeu (SEQ ID NO:229); Arg Allyl(Gly) Ile Gly Arg Leu (SEQ ID NO:230); Ile Allyl(Gly) Ile Gly Arg Leu (SEQ ID NO:231); Met Allyl(Gly) Ile Gly Arg Leu (SEQ ID NO:232); Tyr Ile Gly Ser Arg (SEQ ID NO:233); Phe (2-furyl)Ala Ile Gly Arg (SEQ ID NO:234); Phe Thr Ile Gly Arg (SEQ ID NO:235); Phe StyrylGly Ile Gly Arg Leu (SEQ ID NO:236); Phe HOCit Ile Gly Arg Leu (SEQ ID NO:237); Phe Thr Ile Gly Arg Leu (SEQ ID NO:238); Phe (2-furyl)Ala Ile Gly Arg Leu (SEQ ID NO:239); Phe Ile Gly Arg Leu (SEQ ID NO:240); Phe Allyl(Gly) Ile Gly Arg Leu (SEQ ID NO:241); Arg Gly Ile Leu Phe (SEQ ID NO:242); Gly Ile Leu Phe (SEQ ID NO:243); Leu Arg Gly Ile Leu (SEQ ID NO:244); Leu Arg Gly (d)Ile Leu Phe (SEQ ID NO:245); Leu Arg Gly Phe Leu Phe (SEQ ID NO:246); Leu Arg Gly Leu Leu Phe (SEQ ID NO:247); Leu Arg Gly Ile Leu (d)Phe (SEQ ID NO:248); Leu Arg Gly Ile (d)Leu Phe (SEQ ID NO:249); Eeu (d)Arg Gly Ile Leu Phe (SEQ ID NO:250); (d)Leu Arg Gly Ile Leu Phe (SEQ ID NO:251); Phe Arg Gly Ile Leu Phe (SEQ ID NO:252); Leu Arg Gly Ile AllyGly Phe (SEQ ID NO:253); Phe Allyl(Gly) Ile Gly Arg His (SEQ ID NO:254); Phe Allyl(Gly) Ile Gly Arg Asp (SEQ ID NO:255); Phe Allyl(Gly) Ile Gly Arg Arg (SEQ ID NO:256); Phe Allyl(Gly) Ile Gly Arg Phe (SEQ ID NO:257); Phe Allyl(Gly) Ile Gly Arg Ala (SEQ ID NO:258); Phe Allyl(Gly) Ile Gly Arg Gly (SEQ ID NO:259); Phe Allyl (Gly) Ile Gly Arg Gln (SEQ ID NO:260); Phe Allyl(Gly) Ile Gly Arg Glu (SEQ ID NO:261); Phe Allyl(Gly) Ile Gly Arg Thr (SEQ ID NO:262); Phe Allyl(Gly) Ile Gly Arg Tyr (SEQ ID NO:263); Phe Allyl(Gly) Ile Gly Arg Ser (SEQ ID NO:264); Phe Allyl(Gly) Ile Gly Arg Asn (SEQ ID NO:265); Phe Allyl(Gly) Ile Gly Arg Met (SEQ ID NO:266); Phe Allyl (Gly) Ile Gly Arg Lys (SEQ ID NO:267); Phe Allyl(Gly) Ile Gly Arg Ile (SEQ ID NO:268); Phe Allyl(Gly) Ile Gly Arg Trp (SEQ ID NO:269); Phe Allyl(Gly) Ile Gly Arg Pro (SEQ ID NO:270); Phe Allyl(Gly) Ile Gly Arg Val (SEQ ID NO:271); Phe Allyl(Gly) Ile Gly His Leu (SEQ ID NO:272); Phe Allyl (Gly) Ile Gly Asp Leu (SEQ ID NO:273); Phe Allyl(Gly) Ile Gly Glu Leu (SEQ ID NO:274); Phe Allyl(Gly) Ile Gly Gln Leu (SEQ ID NO:275); Phe Allyl(Gly) Ile Gly Gly Leu (SEQ ID NO:276); Phe Allyl(Gly) Ile Gly Ala Leu (SEQ ID NO:277); Phe Allyl(Gly) Ile Gly Phe Leu (SEQ ID NO:278); Phe Allyl(Gly) Ile Gly Lys Leu (SEQ ID NO:279); Phe Allyl (Gly) Ile Gly Leu Leu (SEQ ID NO:280); Phe Allyl(Gly) Ile Gly Met Leu (SEQ ID NO:281); Phe Allyl(Gly) Ile Gly Asn Leu (SEQ ID NO:282); Phe Allyl(Gly) Ile Gly Ser Leu (SEQ ID NO:283); Phe Allyl(Gly) Ile Gly Tyr Leu (SEQ ID NO:284); Phe Allyl(Gly) Ile Gly Thr Leu (SEQ ID NO:285); Phe Allyl(Gly) Ile Gly Ile Leu (SEQ ID NO:286); Phe Allyl (Gly) Ile Gly Trp Leu (SEQ ID NO:287); Phe Allyl(Gly) He Gly Pro Leu (SEQ ID NO:288); Phe Allyl(Gly) Ile Gly Val Leu (SEQ ID NO:289); Phe N-Allyl(Gly) Ile Gly Arg Leu (SEQ ID NO:290); Phe Allyl(Gly) Tyr Gly Arg Leu (SEQ ID NO:291); Phe Allyl(Gly) His Gly Arg Leu (SEQ ID NO:292); Phe Allyl(Gly) Asn Gly Arg Leu (SEQ ID NO:293); Phe Allyl(Gly) Asp Gly Arg Leu (SEQ ID NO:294); Phe Allyl (Gly) Gln Gly Arg Leu (SEQ ID NO:295); Phe Allyl(Gly) Glu Gly Arg Leu (SEQ ID NO:296); Phe Allyl(Gly) Lys Gly Arg Leu (SEQ ID NO:297); Phe Allyl(Gly) Arg Gly Arg Leu (SEQ ID NO:298); Phe Allyl(Gly) Ile Arg Arg Leu (SEQ ID NO:299); Phe Allyl(Gly) Ile Asn Arg Leu (SEQ ID NO:300); Phe Allyl(Gly) Ile His Arg Leu (SEQ ID NO:301); Phe Allyl (Gly) Ile Lys Arg Leu (SEQ ID NO:302); Phe Allyl(Gly) Ile Gln Arg Leu (SEQ ID NO:303); Phe Allyl(Gly) Ile Phe Arg Leu (SEQ ID NO:304); Phe Allyl(Gly) Ile Ser Arg Leu (SEQ ID NO:305); Phe Allyl(Gly) Ile Val Arg Leu (SEQ ID NO:306); Phe Allyl(Gly) Ile Asp Arg Leu (SEQ ID NO:307); Phe Allyl(Gly) Ile Glu Arg Leu (SEQ ID NO:308); Phe N-Allyl(Gly) Ile Gly Arg (SEQ ID NO:309); Phe N-Allyl(Gly) Ile Gly Arg Leu (SEQ ID NO:310); Benzyl Allyl(Gly) Ile Gly Arg Leu (SEQ ID NO:311); c(Phe Allyl(Gly) Ile Gly Arg Leu) (SEQ ID NO:312); Gly Phe Gly Ile Leu Arg (SEQ ID NO:313); and Ile Gly Phe Leu Arg Gly (SEQ ID NO:314).

In further particular embodiments, a tight junction agonist may consist of a peptide having an amino acid sequence selected from the group consisting of: Cys Ile Gly Arg Leu (SEQ ID NO:23); Ile Gly Arg Leu (SEQ ID NO:24); Phe Cys Ile Gly Arg (SEQ ID NO:25); Phe Cys Ile Gly (SEQ ID NO:26); Ala Cys Ile Gly Arg Leu (SEQ ID NO:27); Phe Ala Ile Gly Arg Leu (SEQ ID NO:28); Phe Cys Ala Gly Arg Leu (SEQ ID NO:29); Phe Cys Ile Ala Arg Leu (SEQ ID NO:30); Phe Cys Ile Gly Ala Leu (SEQ ID NO:31); Phe Cys Ile Gly Arg Ala (SEQ ID NO:32); Phe Cys Ile Gly Arg Leu (SEQ ID NO:33); Pro Cys Ile Gly Arg Leu (SEQ ID NO:34); Gln Cys Ile Gly Arg Leu (SEQ ID NO:35); Gly Cys Ile Gly Arg Leu (SEQ ID NO:36); Thr Cys Ile Gly Arg Leu (SEQ ID NO:37); Ser Cys Ile Gly Arg Leu (SEQ ID NO:38); Sar Cys Ile Gly Arg Leu (SEQ ID NO:39); Asn Cys Ile Gly Arg Leu (SEQ ID NO:40); Arg Cys Ile Gly Arg Leu (SEQ ID NO:41); Cha Cys Ile Gly Arg Leu (SEQ ID NO:42); Aib Cys Ile Gly Arg Leu (SEQ ID NO:43); (t-Bu)Gly Cys Ile Gly Arg Leu (SEQ ID NO:44); Phe Hse Ile Gly Arg Leu (SEQ ID NO:45); Phe Hse Ile Gly Arg Leu (SEQ ID NO:46); Phe Thr Ile Gly Arg Leu (SEQ ID NO:47); Phe Abu Ile Gly Arg Leu (SEQ ID NO:48); Phe Ser Ile Gly Arg Leu (SEQ ID NO:49); Phe Met(O) Ile Gly Arg Leu (SEQ ID NO:50); Phe Met(O)2 Ile Gly Arg Leu (SEQ ID NO:51); Phe (d)Cys Ile Gly Arg Leu (SEQ ID NO:52); Phe Met Ile Gly Arg Leu (SEQ ID NO:53); Nva Cys Ile Gly Arg Leu (SEQ ID NO:54); Val Cys Ile Gly Arg Leu (SEQ ID NO:55); Hse Cys Ile Gly Arg Leu (SEQ ID NO:56); Phe Cys Ile Gly Arg Gly (SEQ ID NO:57); (d)Ala Cys Ile Gly Arg Gly (SEQ ID NO:58); Ala Cys Ile Gly Arg Gly (SEQ ID NO:59); Phe Cys Ile Gly Arg Gly (SEQ ID NO:60); (d)Phe Cys Ile Gly Arg Gly (SEQ ID NO:61); Phe Cys Ile Gly Arg Ser (SEQ ID NO:62); Phe Cys Ile Gly Arg Gln (SEQ ID NO:63); Phe Cys Ile Gly Arg (d)Leu (SEQ ID NO:64); Phe Cys Ile Gly Arg Lys (SEQ ID NO:65); Phe Cys Ile Gly Arg (d)Ala (SEQ ID NO:66); Phe Cys Ile Gly Arg Ile (SEQ ID NO:67); Phe Cys Ile Gly Arg Gly (SEQ ID NO:68); Phe Cys Ile Gly Arg Nva (SEQ ID NO:69); Phe Cys Ile Gly Arg betaAla (SEQ ID NO:70); Phe Cys Ile Gly Arg (SEQ ID NO:71); Phe Cys Ile Gly Arg Asp (SEQ ID NO:72); Phe Cys Ile Gly Arg MeAla (SEQ ID NO:73); Phe Cys Ile Gly Arg Abu (SEQ ID NO:74); Phe Cys Ile Gly Arg Glu (SEQ ID NO:75); Phe Cys Ile Gly Arg Aib (SEQ ID NO:76); Phe Cys Ile Gly Arg Phe (SEQ ID NO:77); Phe Cys Ile Gly Arg Asn (SEQ ID NO:78); Phe Cys Ile Gly Arg Pro (SEQ ID NO:79); Glu Cys Ile Gly Arg Leu (SEQ ID NO:80); Asp Cys Ile Gly Arg Leu (SEQ ID NO:81); Phe Cys Ile Gly Arg Cha (SEQ ID NO:82); Abu Cys Ile Gly Arg Leu (SEQ ID NO:83); Lys Cys Ile Gly Arg Leu (SEQ ID NO:84); Orn Cys Ile Gly Arg Leu (SEQ ID NO:85); Phe Cys Ile Gly Arg Leu Cys (SEQ ID NO:86); Leu Gly Gln Gln Gln Pro Phe Pro Pro Gln Gln Pro Tyr (SEQ ID NO:87); Phe Nva Ile Gly Arg Leu (SEQ ID NO:88); Phe Nle Ile Gly Arg Leu (SEQ ID NO:89); Pro Gly Pro Gly Arg Leu (SEQ ID NO:90); Phe Cys Ile Pro Gly Pro (SEQ ID NO:91); Phe Cys Leu Gly Arg Leu (SEQ ID NO:92); Phe Cys Ile Gly Gly Val Leu Val Gln Pro Gly (SEQ ID NO:93); Gly Cys Ile Gly Arg Gly (SEQ ID NO:94); Tyr Cys Ile Gly Arg Leu (SEQ ID NO:95); Phe Cys Ile Gly Cit Leu (SEQ ID NO:96); Ac Ala Cys Ile Gly Arg Leu (SEQ ID NO:97); Trp Cys Ile Gly Arg Leu (SEQ ID NO:98); Ac Ala Cys Ile Gly Arg Ser (SEQ ID NO:99); Ac Ala Cys Ile Gly Arg Ala (SEQ ID NO:100); Phe(4-NO2) Cys Ile Gly Arg Leu (SEQ ID NO:101); Phe(4-Cl) Cys Ile Gly Arg Leu (SEQ ID NO:102); Phe Cys Ile Gly Arg Phe(4-Cl) (SEQ ID NO:103); Phe Cys Ile Gly Arg Phe (4-NO2) (SEQ ID NO:104); Ac Phe Cys Ile Gly Arg Phe (SEQ ID NO:105); Tic Cys Ile Gly Arg Leu (SEQ ID NO:106); Ser Leu Ile Gly Arg Leu (SEQ ID NO:107); Leu Arg Gly Ile Cys Phe (SEQ ID NO:108); Leu Arg Gly Ile (d)Cys Phe (SEQ ID NO:109); (d)Leu Arg Gly Ile Cys Phe (SEQ ID NO:110); Leu (d)Arg Gly Ile Cys Phe (SEQ ID NO:111); Phe Cys Ile Gly (d)Arg Leu (SEQ ID NO:112): Phe Cys Ile(nMe) Gly Arg Leu (SEQ ID NO:113); Phe Cys Ile Gly Arg Thi (SEQ ID NO:114); Thi Cys Ile Gly Arg Leu (SEQ ID NO:115); (d)Leu (d)Arg Gly (d)Ile (d)Cys (d)Phe (SEQ ID NO:116); (d)Phe (d)Cys Ile Gly (d)Arg (d)Leu (SEQ ID NO:117); (d)Phe (d)Cys (d)Ile Gly Arg (d)Leu (SEQ ID NO:118); Phe Cys (d)Ile Gly Arg Leu (SEQ ID NO:119); Phe (d)Cys (d)Ile Gly (d)Arg (d)Leu (SEQ ID NO:120); (d)Phe Cys (d)Ile Gly (d)Arg (d)Leu (SEQ ID NO:121); Leu Arg Gly Ile Cys (d)Phe (SEQ ID NO:122); (d)Leu (d)Arg Gly (d)Ile Cys (d)Phe (SEQ ID NO:123); Leu (d)Arg Gly (d)Ile (d)Cys (d)Phe (SEQ ID NO:124); Leu Arg Gly (d)Ile Cys Phe (SEQ ID NO:125); (d)Phe (d)Cys (d)Ile Gly (d)Arg Leu (SEQ ID NO:126); (d)Leu (d)Arg Gly Ile (d)Cys (d)Phe (SEQ ID NO:127); (d)Leu Arg Gly (d)Ile (d)Cys (d)Phe (SEQ ID NO:128); (d)Leu (d)Arg Gly (d)Ile (d)Cys Phe (SEQ ID NO:129); Ac Phe Hse Ile Gly Arg Ala (SEQ ID NO:130); Ac Phe Hse Ile Gly Arg Ser (SEQ ID NO:131); Ac Phe Use Ile Gly Arg Phe (SEQ ID NO:132); Phe Cys Ile Gly Arg Tic (SEQ ID NO:133); Phe Ile Gly Arg Phe (SEQ ID NO:134); Phe Cys(S-benzyl) Ile Gly Arg Leu (SEQ ID NO:135); Phe Cys (t-buthiol) Ile Gly Arg Leu (SEQ ID NO:136): Phe Leu Ile Gly Arg Leu (SEQ ID NO:137); Phe Phe Leu Ile Gly Arg Leu (SEQ ID NO:138); Phe Phe Ile Gly Arg Leu (SEQ ID NO:139); Phe Phg Ile Gly Arg Leu (SEQ ID NO:140); Phe Pro Ile Gly Arg Leu (SEQ ID NO:141); Phe (d)Val Ile Gly Arg Leu (SEQ ID NO:142); Phe Cha Ile Gly Arg Leu (SEQ ID NO:143); Phe Allyl(Gly) Ile Gly Arg Leu (SEQ ID NO:144); Phe tBu(Gly) Ile Gly Arg Leu (SEQ ID NO:145); Phe Cys Ala Gly (SEQ ID NO:146); Phe Cys Gly Gly (SEQ ID NO:147); Phe Trp Ile Gly Arg Leu (SEQ ID NO:148); Phe His Ile Gly Arg Leu (SEQ ID NO:149); Phe Pro Ile Gly Arg Leu (SEQ ID NO:150); Phe Asp Ile Gly Arg Leu (SEQ ID NO:151); Phe Dab Ile Gly Arg Leu (SEQ ID NO:152); Phe (d)Cys Ile Gly (d)Arg Leu (SEQ ID NO:153); (d)Leu Arg Gly Ile Cys Phe (SEQ ID NO:154); (d)Leu (d)Arg Gly Ile Cys Phe (SEQ ID NO:155); (d)Leu (d)Arg Gly Ile Cys (d)Phe (SEQ ID NO:156); (d)Leu (d)Arg Gly Ile (d)Cys Phe (SEQ ID NO:157); Gly Phe Cys Ile Gly Arg Leu (SEQ ID NO:158); Phe Leu Ile Gly Arg Leu (SEQ ID NO:159); Ac Phe Cys Ile Gly Arg Leu (SEQ ID NO:160); Phe Phe Ile Gly Arg Leu (SEQ ID NO:161); Phe (cyclopropane)Pro Ile Gly Arg Leu (SEQ ID NO162:); Phe Dpr Ile Gly Arg Leu (SEQ ID NO:163); Phe Pen(Acm) Ile Gly Arg Leu (SEQ ID NO:164); Leu Arg Gly Gly Arg Leu (SEQ ID NO:165); (d)Phe Cys Ile Gly Arg Leu (SEQ ID NO:166); (d)Phe (d)Cys (d)Ile Gly (d)Arg (d)Leu (SEQ ID NO:167); Phe Arg Ile Gly Arg Leu (SEQ ID NO:168); Phe Gly Ile Gly Arg Leu (SEQ ID NO:169); Phe Gln Ile Gly Arg Leu (SEQ ID NO:170); Phe Glu Ile Gly Arg Leu (SEQ ID NO:171); Phe Lys Ile Gly Arg Leu (SEQ ID NO:172); Phe Asn Ile Gly Arg Leu (SEQ ID NO:173); Phe Tyr Ile Gly Arg Leu (SEQ ID NO:174); Phe Leu Ile Gly Arg Leu (SEQ ID NO:175); Phe Val Ile Gly Arg Leu (SEQ ID NO:176); Phe Ile Ile Gly Arg Leu (SEQ ID NO:177); Phe Hcy Ile Gly Arg Leu (SEQ ID NO:178); Ser Leu Ile Gly Arg Leu (SEQ ID NO:179); Phe Cys Ala Gly Met Ser (SEQ ID NO:180): Phe Cys Val Gly Met Ser (SEQ ID NO:181); Phe (2-pyridiyl)Ala Ile Gly Arg Leu (SEQ ID NO:182): Phe Leu (d)Ile Gly Arg Leu (SEQ ID NO:183); Ac Phe Leu Ile Gly Arg Leu (SEQ ID NO:184); Phe (d)Leu Ile Gly Arg Leu (SEQ ID NO:185); Leu Arg Gly (d)Ile Leu Phe (SEQ ID NO:186); Phe Abu(dimer) Ile Gly Arg Leu (SEQ ID NO:187); Phe (Dehydro)Leu Ile Gly Arg Leu (SEQ ID NO:188); Leu Arg Gly Ile Leu Phe (SEQ ID NO:189); Ac Phe Hse Ile Gly Arg (SEQ ID NO:190); Phe Hse (d)Ile Gly Arg (SEQ ID NO:191); Ac Phe Hsc Ile Gly Arg Leu (SEQ ID NO:192); Phe Leu Ile Gly Arg (SEQ ID NO:193); Phe Hse (d)Ile Gly Arg Leu (SEQ ID NO:194); Phe (4-CN) Phe Ile Gly Arg Leu (SEQ ID NO:195); Phe (3-Me) Phe Ile Gly Arg Leu (SEQ ID NO:196); Phe Cyclopropyl(Ala) Ile Gly Arg Leu (SEQ ID NO:197); Phe Allyl(Gly) Ile Gly Arg (SEQ ID NO:198); Phe (d)Allyl(Gly) Ile Gly Arg (SEQ ID NO:199); Phe Pra Ile Gly Arg (SEQ ID NO:200); Phe Allyl(Gly) Ile Thr Arg Leu (SEQ ID NO:201); Phe Allyl(Gly) Ile Leu Arg Leu (SEQ ID NO:202); Phe Allyl(Gly) Ile Ile Arg Leu (SEQ ID NO:203); Phe Allyl(Gly) Ile Ala Arg Leu (SEQ ID NO:204); Phe Allyl(Gly) Ile Pro Arg Leu (SEQ ID NO:205); Phe Allyl(Gly) Pro Gly Arg Leu (SEQ ID NO:206); Phe Allyl(Gly) Phe Gly Arg Leu (SEQ ID NO:207); Phe Allyl(Gly) Thr Gly Arg Leu (SEQ ID NO:208); Phe Allyl(Gly) Leu Gly Arg Leu (SEQ ID NO:209); Phe Allyl(Gly) Ser Gly Arg Leu (SEQ ID NO:210); Phe Allyl(Gly) Phe Gly Arg Leu (SEQ ID NO:211); Phe Allyl(Gly) Val Gly Arg Leu (SEQ ID NO:212); Phe Allyl(Gly) Gly Gly Arg Leu (SEQ ID NO:213); Phe Allyl(Gly) Ala Gly Arg Leu (SEQ ID NO:214); Met Allyl(Gly) Ile Gly Arg Leu (SEQ ID NO:215); Gln Allyl(Gly) Ile Gly Arg Leu (SEQ ID NO:216); Leu Allyl(Gly) Ile Gly Arg Leu (SEQ ID NO:217); Ser Allyl(Gly) Ile Gly Arg Leu (SEQ ID NO:218); Thr Allyl(Gly) Ile Gly Arg Leu (SEQ ID NO:219); Glu Allyl(Gly) Ile Gly Arg Leu (SEQ ID NO:220); Val Allyl (Gly) Ile Gly Arg Leu (SEQ ID NO:221); Tyr Allyl(Gly) Ile Gly Arg Leu (SEQ ID NO:222); Gly Allyl(Gly) Ile Gly Arg Leu (SEQ ID NO:223); Asp Allyl(Gly) Ile Gly Arg Leu (SEQ ID NO:224); Trp Allyl(Gly) Ile Gly Arg Leu (SEQ ID NO:225); Lys Allyl(Gly) Ile Gly Arg Leu (SEQ ID NO:226); Ala Allyl(Gly) Ile Gly Arg Leu (SEQ ID NO:227); His Allyl (Gly) Ile Gly Arg Leu (SEQ ID NO:228): Pro Allyl(Gly) Ile Gly Arg Leu (SEQ ID NO:229); Arg Allyl(Gly) Ile Gly Arg Leu (SEQ ID NO:230); Ile Allyl(Gly) Ile Gly Arg Leu (SEQ ID NO:231); Met Allyl(Gly) Ile Gly Arg Leu (SEQ ID NO:232); Tyr Ile Gly Ser Arg (SEQ ID NO:233); Phe (2-furyl)Ala Ile Gly Arg (SEQ ID NO:234); Phe Thr Ile Gly Arg (SEQ ID NO:235); Phe StyrylGly Ile Gly Arg Leu (SEQ ID NO:236); Phe HOCit Ile Gly Arg Leu (SEQ ID NO:237); Phe Thr Ile Gly Arg Leu (SEQ ID NO:238); Phe (2-furyl)Ala Ile Gly Arg Leu (SEQ ID NO:239); Phe Ile Gly Arg Leu (SEQ ID NO:240); Phe Allyl(Gly) Ile Gly Arg Leu (SEQ ID NO:241); Arg Gly Ile Leu Phe (SEQ ID NO:242); Gly Ile Leu Phe (SEQ ID NO:243); Leu Arg Gly Ile Leu (SEQ ID NO:244); Leu Arg Gly (d)Ile Leu Phe (SEQ ID NO:245); Leu Arg Gly Phe Leu Phe (SEQ ID NO:246); Leu Arg Gly Leu Leu Phe (SEQ ID NO:247); Leu Arg Gly Ile Leu (d)Phe (SEQ ID NO:248); Leu Arg Gly Ile (d)Leu Phe (SEQ ID NO:249); Leu (d)Arg Gly Ile Leu Phe (SEQ ID NO:250); (d)Leu Arg Gly Ile Leu Phe (SEQ ID NO:251); Phe Arg Gly Ile Leu Phe (SEQ ID NO:252); Leu Arg Gly Ile AllyGly Phe (SEQ ID NO:253); Phe Allyl(Gly) Ile Gly Arg His (SEQ ID NO:254); Phe Allyl(Gly) Ile Gly Arg Asp (SEQ ID NO:255); Phe Allyl(Gly) Ile Gly Arg Arg (SEQ ID NO:256); Phe Allyl(Gly) Ile Gly Arg Phe (SEQ ID NO:257); Phe Allyl(Gly) Ile Gly Arg Ala (SEQ ID NO:258); Phe Allyl(Gly) Ile Gly Arg Gly (SEQ ID NO:259); Phe Allyl (Gly) Ile Gly Arg Gln (SEQ ID NO:260); Phe Allyl(Gly) Ile Gly Arg Glu (SEQ ID NO:261); Phe Allyl(Gly) Ile Gly Arg Thr (SEQ ID NO:262); Phe Allyl(Gly) Ile Gly Arg Tyr (SEQ ID NO:263); Phe Allyl(Gly) Ile Gly Arg Ser (SEQ ID NO:264); Phe Allyl(Gly) Ile Gly Arg Asn (SEQ ID NO:265); Phe Allyl(Gly) Ile Gly Arg Met (SEQ ID NO:266); Phe Allyl (Gly) Ile Gly Arg Lys (SEQ ID NO:267); Phe Allyl(Gly) Ile Gly Arg Ile (SEQ ID NO:268); Phe Allyl(Gly) Ile Gly Arg Trp (SEQ ID NO:269); Phe Allyl(Gly) Ile Gly Arg Pro (SEQ ID NO:270); Phe Allyl(Gly) Ile Gly Arg Val (SEQ ID NO:271); Phe Allyl(Gly) Ile Gly His Leu (SEQ ID NO:272); Phe Allyl (Gly) Ile Gly Asp Leu (SEQ ID NO:273); Phe Allyl(Gly) Ile Gly Glu Leu (SEQ ID NO:274); Phe Allyl(Gly) Ile Gly Gln Leu (SEQ ID NO:275); Phe Allyl(Gly) Ile Gly Gly Leu (SEQ ID NO:276); Phe Allyl(Gly) Ile Gly Ala Leu (SEQ ID NO:277); Phe Allyl(Gly) Ile Gly Phe Leu (SEQ ID NO:278); Phe Allyl(Gly) Ile Gly Lys Leu (SEQ ID NO:279); Phe Allyl (Gly) Ile Gly Leu Leu (SEQ ID NO:280); Phe Allyl(Gly) Ile Gly Met Leu (SEQ ID NO:281); Phe Allyl(Gly) Ile Gly Asn Leu (SEQ ID NO:282); Phe Allyl(Gly) Ile Gly Ser Leu (SEQ ID NO:283); Phe Allyl(Gly) Ile Gly Tyr Leu (SEQ ID NO:284); Phe Allyl(Gly) Ile Gly Thr Leu (SEQ ID NO:285); Phe Allyl(Gly) Ile Gly Ile Leu (SEQ ID NO:286); Phe Allyl (Gly) Ile Gly Trp Leu (SEQ ID NO:287); Phe Allyl(Gly) Ile Gly Pro Leu (SEQ ID NO:288); Phe Allyl(Gly) Ile Gly Val Leu (SEQ ID NO:289); Phe N-Allyl(Gly) Ile Gly Arg Leu (SEQ ID NO:290); Phe Allyl(Gly) Tyr Gly Arg Leu (SEQ ID NO:291); Phe Allyl(Gly) His Gly Arg Leu (SEQ ID NO:292); Phe Allyl(Gly) Asn Gly Arg Leu (SEQ ID NO:293); Phe Allyl(Gly) Asp Gly Arg Leu (SEQ ID NO:294); Phe Allyl (Gly) Gln Gly Arg Leu (SEQ ID NO:295); Phe Allyl(Gly) Glu Gly Arg Leu (SEQ ID NO:296); Phe Allyl(Gly) Lys Gly Arg Leu (SEQ ID NO:297); Phe Allyl(Gly) Arg Gly Arg Leu (SEQ ID NO:298); Phe Allyl(Gly) Ile Arg Arg Leu (SEQ ID NO:299); Phe Allyl(Gly) Ile Asn Arg Leu (SEQ ID NO:300); Phe Allyl(Gly) Ile His Arg Leu (SEQ ID NO:301); Phe Allyl (Gly) Ile Lys Arg Leu (SEQ ID NO:302); Phe Allyl(Gly) Ile Gln Arg Leu (SEQ ID NO:303); Phe Allyl(Gly) Ile Phe Arg Leu (SEQ ID NO:304); Phe Allyl(Gly) Ile Ser Arg Leu (SEQ ID NO:305); Phe Allyl(Gly) Ile Val Arg Leu (SEQ ID NO:306); Phe Allyl(Gly) Ile Asp Arg Leu (SEQ ID NO:307); Phe Allyl(Gly) Ile Glu Arg Leu (SEQ ID NO:308); Phe N-Allyl(Gly) Ile Gly Arg (SEQ ID NO:309); Phe N-Allyl(Gly) Ile Gly Arg Leu (SEQ ID NO:310); Benzyl Allyl(Gly) Ile Gly Arg Leu (SEQ ID NO:311); c(Phe Allyl(Gly) Ile Gly Arg Leu) (SEQ ID NO:312); Gly Phe Gly Ile Leu Arg (SEQ ID NO:313); and Ile Gly Phe Leu Arg Gly (SEQ ID NO:314).

When the tight junction agonist is a peptide, any length of peptide may be used. For example, an agonist may be about 3, about 4, about 5, about 6, about 7, about 8, about 9, about 10, about 11, about 12, about 13, about 14 or about 15 amino acids in length. In some embodiments, a peptide tight junction agonist may be from about 3 to about 12, from about 4 to about 12, from about 5 to about 12, from about 6 to about 12, from about 7 to about 12, from about 8 to about 12, from about 9 to about 12, from about 10 to about 12, from about 3 to about 10, from about 4 to about 10, from about 5 to about 10, from about 6 to about 10, from about 7 to about 10, from about 8 to about 10, from about 9 to about 10 amino acids in length. In some embodiments, a peptide tight junction agonist may be 9 amino acids or less in length. In some embodiments of the invention, peptides do not encompass full length ZOT or zonulin.

Peptide agonists can be chemically synthesized and purified using well-known techniques, such as described in *High Performance Liquid Chromatography of Peptides and Proteins: Separation Analysis and Conformation*, Eds. Mant et al., C.R.C. Press (1991), and a peptide synthesizer, such as Symphony (Protein Technologies, Inc.); or by using recombinant DNA techniques, i.e., where the nucleotide sequence encoding the peptide is inserted in an appropriate expression vector, e.g., an *E. coli* or yeast expression vector, expressed in the respective host cell, and purified from the cells using well-known techniques.

Therapeutic Agents

Compositions of the invention typically comprise one or more therapeutic agents and/or immunogenic agents. Therapeutic agents that can be used in the compositions include agents that act on any organ of the body, such as heart, brain, intestine, or kidneys. Examples of suitable therapeutic agents include, but are not limited to, glucose metabolism agents (e.g., insulin), antibiotics, antineoplastics, antihypertensives, antiepileptics, central nervous system agents, and immune system suppressants.

The particular therapeutic and/or immunogenic agent used in the compositions of the invention can be any small molecule compound, biologically active peptide, vaccine, or any other moiety. In some embodiments, therapeutic agents for use in the invention may be those that, in the absence of a tight junction agonist, are not adequately absorbed into the bloodstream through the skin.

Examples of drug compounds which can be employed as therapeutic agents in the present invention include, but are not limited to, drugs which act on the cardiovascular system, drugs which act on the central nervous system, antineoplastic drugs and antibiotics. Examples of drugs which act on the cardiovascular system include, but are not limited to, antihypertensives, statins, adenosine, dobutamine, dopamine, epinephrine, norepinephrine, and phentolamine. Others as are known in the art can also be used.

Examples of drugs which act on the central nervous system include, but are not limited to, doxapram, alfentanil. dezocin, nalbuphine, buprenorphine, naloxone, ketorolac, midazolam, and propofol. Other examples include, but are not limited to, antipsychotics, antidepressents, antiepileptics, and drugs used to treat Alzheimers disease. Others as are known in the art can also be used.

Examples of antineopiastic drugs include, but are not limited to, cytarabine, mitomycin, doxorubicin, vincristine and vinblastine, carboplatin, cisplatin, oxaloplatin, vinorelbine, docetaxel, paclitaxel, taxane, 5-fluorouridine related drugs, xeloda, germcitabine, and anthracline. Additional examples include, but are not limited to, Erbitux, Herceptin®, Avastin™, and estrogen receptor antagonists and agonists. Others as are known in the art can also be used.

Examples of antibiotics include, but are not limited to, methicillin, mezlocillin, piperacillin, cetoxitin, cefonicid, cefinetazole and aztreonam. Others as are known in the art can also be used.

Any type of therapeutic and/or immunogenic agent can be used in the practice of the invention. Examples of specific types of agents include, but are not limited to, RNAi, treatment aptamers. antivirals (e.g., amantadine, rimantadine, zanamavir and oseltamivir), immune suppressants (e.g., cyclosporine A), HIV fusion inhibitors (e.g., enfuvirtide), and HIV protease inhibitors, (e.g., ritonavir, saquinavir, indinavir, amprenavir, nelfinavir, lopinavir, atazanavir, entricitabine, and fosamprenavir calcium).

Examples of biologically active peptides that may be used as therapeutic agents in the practice of the present invention include, but are not limited to. hormones, lymphokines, globulins, and albumins. Examples of hormones which can be employed in the present invention include: testosterone, nandrolene, menotropins, insulin and urofolltropin. Other examples of biologically active peptides include: insulin modified by chemical or enzymatic means (including mutations introduced using recombinant DNA technology), parathyroid hormone, parathyroid hormone antagonist, calcitonin, vasopressin, renin, prolactin, growth hormone, thyroid stimulating hormone, corticotropin, corticotropin-releasing factor, follicle stimulating hormone, luteinizing hormone, chorionic gonadotropin, atrial peptides, interferon, tissue plasminogen activator, gammaglobulins, Factor VII, Factor VIII, growth hormone releasing hormone, luteinizing hormone releasing hormone, somatostatin and cholecystokinins. Others as are known in the art can also be used. If the biologically active ingredient is insulin and/or an insulin derivative, the transcutaneous dosage composition is useful for the treatment of diabetes.

Examples of lymphokines which can be employed in the present invention include interferon-α, interferon-β, interferon-γ, interleukin-1, interleukin-2, interleukin-4 and interleukin-8.

Examples of globulins include α-globulins, β-globulins and γ-globulins (immunoglobulin). Examples of immunoglobulins which can be employed in the present invention include polyvalent IgG or specific IgG, IgA and IgM, e.g., anti-tetanus antibodies. An example of albumin which can be used is human serum albumin. Others as are known in the art can also be used.

Examples of antigens that can be used in the compositions of the invention (e.g., immunogenic and/or vaccine compositions) include peptides, proteins, microorganisms (e.g., attenuated and/or recombinant microorganisms), cells (e.g., cancer cells and/or recombinant cells) and viruses (e.g., attenuated and/or recombinant viruses). Examples of peptide antigens include the B subunit of the heat labile enterotoxin of enterotoxigenic *E. coli*, the B subunit of cholera toxin, capsular antigens of enteric pathogens, fimbriae or pili of enteric pathogens, HIV surface antigens, cancer antigens (e.g., cancer cells comprising antigens, isolated antigens, etc.), dust allergens, and acari allergens. Other immunogenic compounds as are known in the art can also be used.

Examples of attenuated microorganisms and viruses that can be used in the compositions of the invention (e.g., vaccine compositions) include those of enterotoxigenic *Escherichia coli*, enteropathogenic *Escherichia coli, Vibrio cholerae, Shigella flexneri, Salmonella typhi* and rotavirus (Fasano et al, In: Le Vaccinazioni in Pediatria, Eds. Vierucci et al, CSH, Milan, pages 109-121 (1991); Guandalini et al, In: Management of Digestive and Liver Disorders in Infants and Children, Elsevior, Eds. Butz et al, Amsterdam, Chapter 25 (1993): Levine et al, Sem. Ned. Infect. Dis., 5.243-250 (1994); and Kaper et al, Clin. Micrbiol. Rev., 8:48-86 (1995), each of which is incorporated by reference herein in its entirety).

Any antigen capable of inducing a protective immune response may be used in the vaccines of the invention. Examples of suitable antigens include, but are not limited to, measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

Formulations

Compositions of the invention may formulated for transcutaneous delivery (e.g., may be transcutaneous dosage forms). Typically such compositions may be provided as topical solutions and/or gels. Those of skill in the art are aware of many different methods and devices for the formation of topical medications, for example, those disclosed by Block, *Medicated Topicals*, in *Remington: The Science and Practice of Pharmacy*, 20th Ed., Chapter 44, Gennaro et al. Eds., Lippincott, Williams and Wilkins Publishing Co., (2000).

Typically, compositions comprising a tight junction agonist (e.g., peptide agonist) comprise a pharmaceutically effective amount of the agonist. The pharmaceutically effective amount of agonist (e.g., peptide agonist) employed may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

Compositions of the invention may comprise one or tight junction agonist at a level of from about 0.000001 wt % to about 50 wt %, from about 0.000001 wt % to about 45 wt %, from about 0.000001 wt % to about 40 wt %, from about 0.000001 wt % to about 35 wt %, from about 0.000001 wt % to about 30 wt %, from about 0.000001 wt % to about 25 wt %, from about 0.000001 wt % to about 20 wt %, from about 0.000001 wt % to about 15 wt %, from about 0.000001 wt % to about 10 wt %, from about 0.000001 wt % to about 5 wt %, from about 0.000001 wt % to about 2.5 wt %, from about 0.000001 wt % to about 1 wt %, from about 0.000001 wt % to about 0.1 wt %, from about 0.000001 wt % to about 0.01 wt %, from about 0.000001 wt % to about 0.001 wt %, from about 0.000001 wt % to about 0.0001 wt %, from about 0.000001 wt % to about 0.00005 wt %, from about 0.0001 wt % to about 50 wt %, from about 0.0001 wt % to about 45 wt %, from about 0.0001 wt % to about 40 wt %, from about 0.0001 wt % to about 35 wt %, from about 0.0001 wt % to about 30 wt %, from about 0.0001 wt % to about 25 wt %, from about 0.0001 wt % to about 20 wt %, from about 0.0001 wt % to about 15 wt %, from about 0.0001 wt % to about 10 wt %, from about 0.0001 wt % to about 5 wt %, from about 0.0001 wt % to about 2.5 wt %, from about 0.0001 wt % to about 1 wt %, from about 0.0001 wt % to about 0.1 wt %, from about 0.0001 wt % to about 0.01 wt %, from about 0.0001 wt % to about 0.001 wt %, from about 0.0001 wt % to about 0.0005 wt %, from about 0.1 wt % to about 50 wt %, from about 0.1 wt % to about 45 wt %, from about 0.1 wt % to about 40 wt %, from about 0.1 wt % to about 35 wt %, from about 0.1 wt % to about 30 wt %, from about 0.1 wt % to about 25 wt %, from about 0.1 wt % to about 20 wt %, from about 0.1 wt % to about 15 wt %, from about 0.1 wt % to about 10 wt %, from about 0.1 wt % to about 5 wt %, from about 0.1 wt % to about 2.5 wt %, from about 0.1 wt % to about 1 wt %, from about 0.1 wt % to about 0.5 wt %, from about 0.1 wt % to about 0.2 wt %, from about 1 wt % to about 50 wt %, from about 1 wt % to about 45 wt %, from about 1 wt % to about 40 wt %, from about 1 wt % to about 35 wt %, from about 1 wt % to about 30 wt %, from about 1 wt % to about 25 wt %, from about 1 wt % to about 20 wt %, from about 1 wt % to about 15 wt %, from about 1 wt % to about 10 wt %, from about 1 wt % to about 5 wt %, from about 1 wt % to about 2.5 wt %, from about 5 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 5 wt % to about 9 wt %, from about 5 wt % to about 8 wt %, from about 5 wt % to about 7 wt %, or from about 5 wt % to about 6 wt % of the total weight of the composition. Compositions of the invention may comprise one or more tight junction agonists at a level of about 0.00001 wt %, about 0.00005 wt %, about 0.0001 wt %, about 0.0005 wt %, about 0.001 wt %, about 0.005 wt %, about 0.01 wt %, about 0.05 wt %, about 0.1 wt %, about 0.5 wt %, about 1 wt %, about 5 wt %, about 10 wt %, about 15 wt %, about 20 wt %, about 25 wt %, about 30 wt %, about 35 wt %, about 40 wt %, about 45 wt %, or about 50 wt % based on the total weight of the composition.

Compositions of the invention may comprise one or more therapeutic agents and/or immunogenic agents at a concentration sufficient to cause the desired biological response (e.g., at a pharmaceutically effective concentration). Compositions of the invention may comprise one or therapeutic and/or immunogenic agents at a level of from about 0.1 wt % to about 50 wt %, from about 0.1 wt % to about 45 wt %, from about 0.1 wt % to about 40 wt %, from about wt % to about 35 wt %, from about 0.1 wt % to about 30 wt %, from about 0.1 wt % to about 25 wt %, from about 0.1 wt % to about 20 wt %, from about 0.1 wt % to about 15 wt %, from about 0.1 wt % to about 10 wt %, from about 0.1 wt % to about 5 wt %, from about 0.1 wt % to about 2.5 wt %, from about 0.1 wt % to about 1 wt %, from about 0.1 wt % to about 0.5 wt %, from about 0.1 wt % to about 0.2 wt %, from about 1 wt % to about 50 wt %, from about 1 wt % to about 45 wt %, from about 1 wt % to about 40 wt %, from about 1 wt % to about 35 wt %, from about 1 wt % to about 30 wt %, from about 1 wt % to about 25 wt %, from about 1 wt % to about 20 wt %, from about 1 wt % to about 15 wt %, from about 1 wt % to about 10 wt %, from about 1 wt % to about 5 wt %, from about 1 wt % to about 2.5 wt %, from about 5 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 5 wt % to about 9 wt %, from about 5 wt % to about 8 wt %, from about 5 wt % to about 7 wt %, or from about 5 wt % to about 6 wt % of the total weight of the composition. Compositions of the invention may comprise one or more therapeutic and/or immunogenic agents at a level of about 0.1 wt %, about 1 wt %, about 5 wt %, about 10 wt %, about 15 wt %, about 20 wt %, about 25 wt %, about 30 wt %, about 35 wt %, about 40 wt %, about 45 wt %, or about 50 wt % based on the total weight of the composition.

Compositions of the invention may comprise one or pharmaceutically acceptable excipients at a level of from about 0.1 wt % to about 50 wt %, from about 0.1 wt % to about 45 wt %, from about 0.1 wt % to about 40 wt %, from about wt % to about 35 wt %, from about 0.1 wt % to about 30 wt %, from about 0.1 wt % to about 25 wt %, from about 0.1 wt % to about 20 wt %, from about 0.1 wt % to about 15 wt %, from about 0.1 wt % to about 10 wt %, from about 0.1 wt % to about 5 wt %, from about 0.1 wt % to about 2.5 wt %, from about 0.1 wt % to about 1 wt %, from about 0.1 wt % to about 0.5 wt %, from about 0.1 wt % to about 0.2 wt %, from about 1 wt % to about 50 wt %, from about 1 wt % to about 45 wt %, from about 1 wt % to about 40 wt %, from about 1 wt % to about 35 wt %, from about 1 wt % to about 30 wt %, from about 1 wt % to about 25 wt %, from about 1 wt % to about 20 wt %, from about 1 wt % to about 15 wt %, from about 1 wt % to about 10 wt %, from about 1 wt % to about 5 wt %, from about 1 wt % to about 2.5 wt %, from about 5 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 5 wt % to about 9 wt %, from about 5 wt % to about 8 wt %, from about 5 wt % to about 7 wt %, or from about 5 wt % to about 6 wt % of the total weight of the composition. Compositions of the invention may comprise one or more pharmaceutically acceptable excipients at a level of about 0.1 wt %, about 1 wt %, about 5 wt %, about 10 wt %, about 15 wt %, about 20 wt %, about 25 wt %, about 30 wt %, about 35 wt %, about 40 wt %, about 45 wt %, or about 50 wt % based on the total weight of the composition.

Methods of Use

The pharmaceutical compositions of the invention can be used for treating, ameliorating, and/or preventing a disease. Any disease may be treated using the compositions of the invention by selection of an appropriate therapeutic and/or immunogenic agent. In one embodiment, the present invention provides a method of treating diabetes by administering a composition comprising one or more tight junction agonist and one or more insulin and/or derivative thereof to the skin of a subject in need of the treatment.

Examples of diseases that can be treated using the compositions of the invention include, but are not limited to, cancer, autoimmune diseases, vascular disease, bacterial infections, gastritis, gastric cancer, collagnenous colitis, inflammatory bowel disease, osteoporosis, systemic lupus erythematosus, food allergy, asthma, and irritable bowel syndrome. For example, to treat cancer of the colon or rectal area, a composition comprising a therapeutically effective amount of Erbitux (Cetuximab) and an absorption enhancing amount of one or more tight junction agonists may be administered to the skin of a patient in need thereof, to treat breast cancer, a composition comprising a therapeutically effective amount of Herceptin (Trastuzumab) and an absorption enhancing amount of one or more tight junction agonists may be administered to the skin of a patient in need thereof, and to treat various types of cancer, a composition comprising a therapeutically effective amount of Avastin (Bevacizumab) and an absorption enhancing amount of one or more tight junction agonist may be administered to the skin of a patient in need thereof. Further examples include treatment of osteoporosis using a composition comprising one or more tight junction agonists and a therapeutically effective amount of Fosamax (Alendronate) administered to the skin of a subject in need thereof, treatment of transplant rejection using a composition comprising one or more tight junction agonists and a therapeutically effective amount of Cyclosporin A administered to the skin of a subject in need thereof, treatment of anemia using a composition comprising one or more tight junction agonists and a therapeutically effective amount of erythropoietin administered to the skin of a subject in need thereof, and treatment of hemophilia using a composition comprising one or more tight junction agonists and a therapeutically effective amount of Factor VIII administered to the skin of a subject in need thereof.

The following examples are provided for illustrative purposes only, and are in no way intended to limit the scope of the present invention.

EXAMPLES

The experiments described in the attached figures were performed with tight junction agonist peptide FCIGRL also known as AT1002.

Example 1

Transcutaneous Immunization (TCI)

Groups of 5 female Balb/c mice (8-10 weeks) were immunized transcutaneously at 0, 4 and 8 weeks with TT alone (25 µg/dose) or together with AT-1002 (0.03-300 µg/dose). For TCI, mice were anesthetized intraperitoneally, for approximately 1 hour, with a ketamine-xylazine mixture to prevent self grooming. A small surface area of the abdomen was shaved and the hair was then completely removed by application of a depilatory cream (Nair) for 2 minutes. The cream was removed with cotton wool soaked in warm water and the prepared skin surface was hydrated with PBS for 5 minutes. 50-100 µl of immunizing solution was applied evenly over the exposed skin and left for up to 1 hr to absorb through the skin. The mice were then washed thoroughly with lukewarm water and patted dry.

Example 2

Antibody Assay

Figure 1:
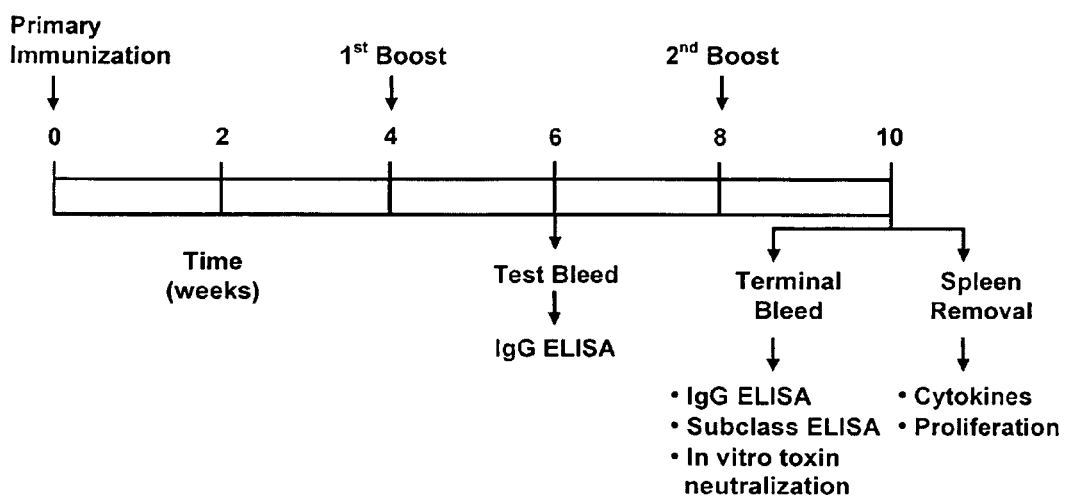
Figure 3:
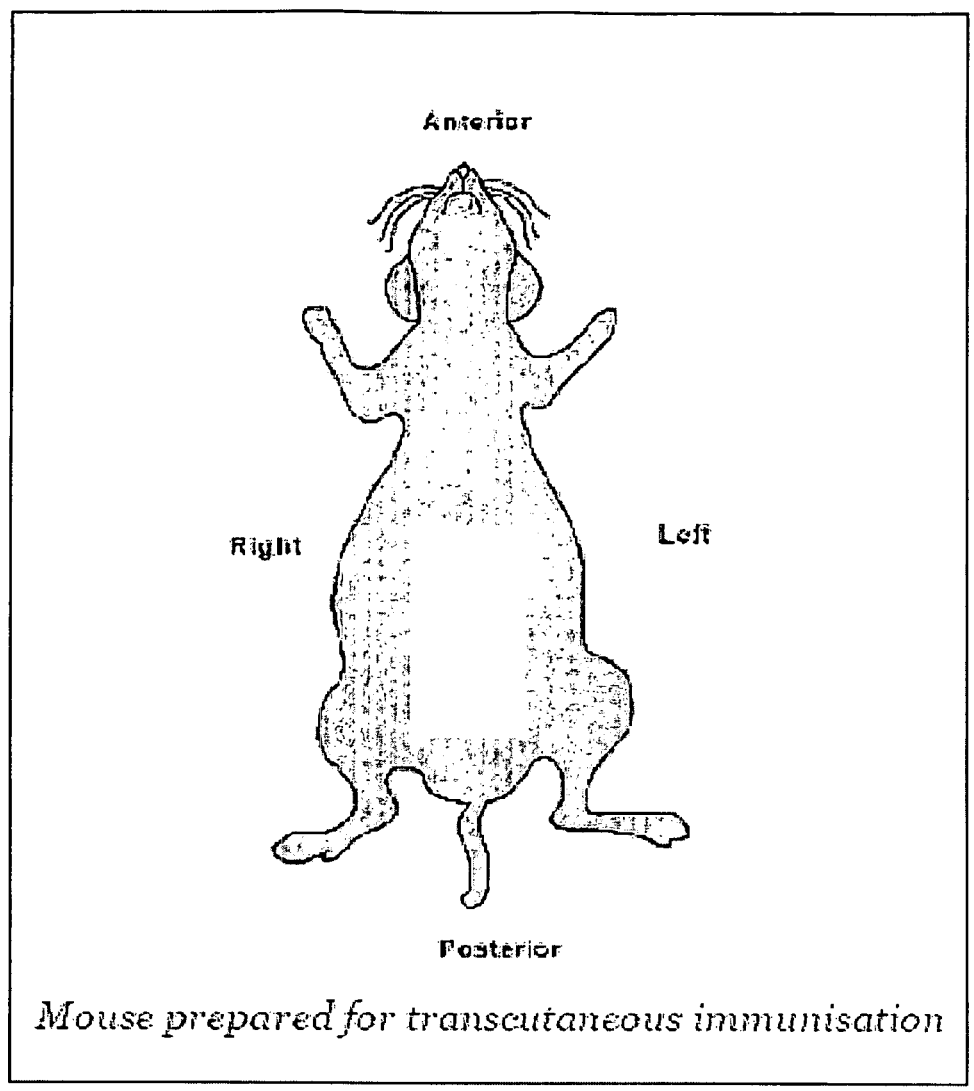
Figure 4A:
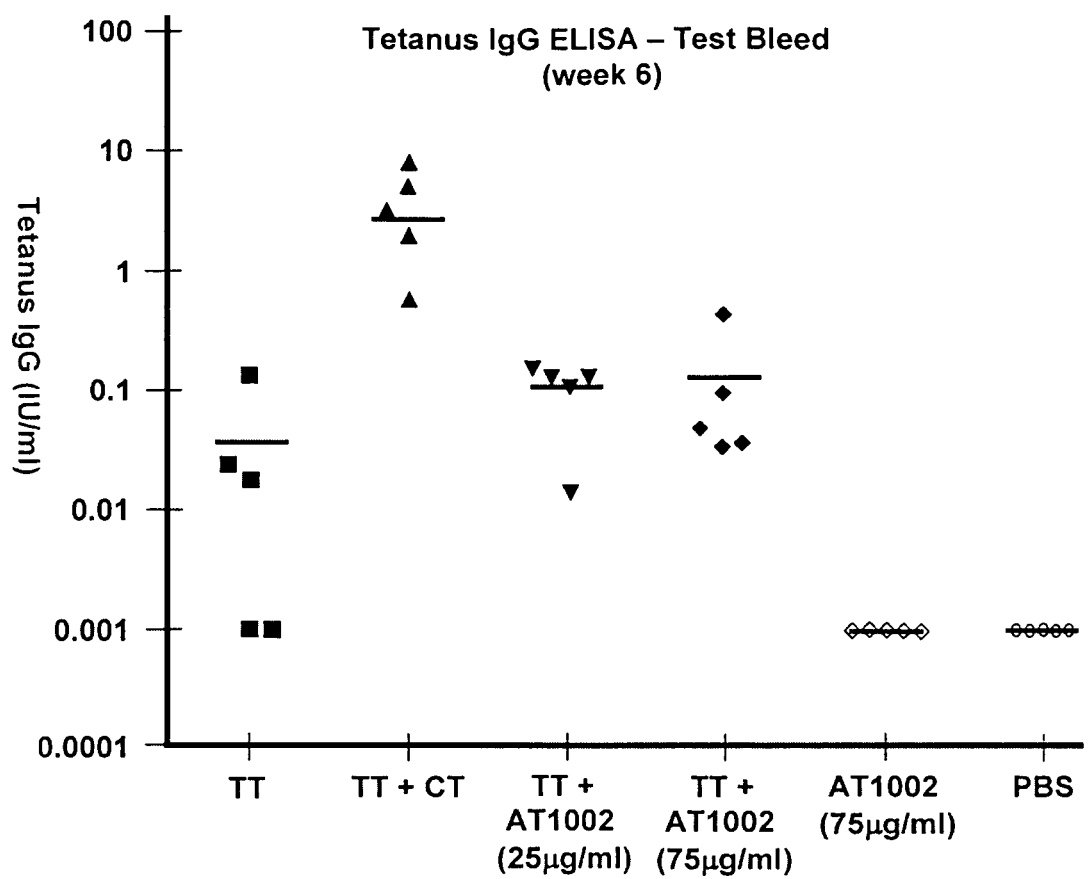
Figure 4B:
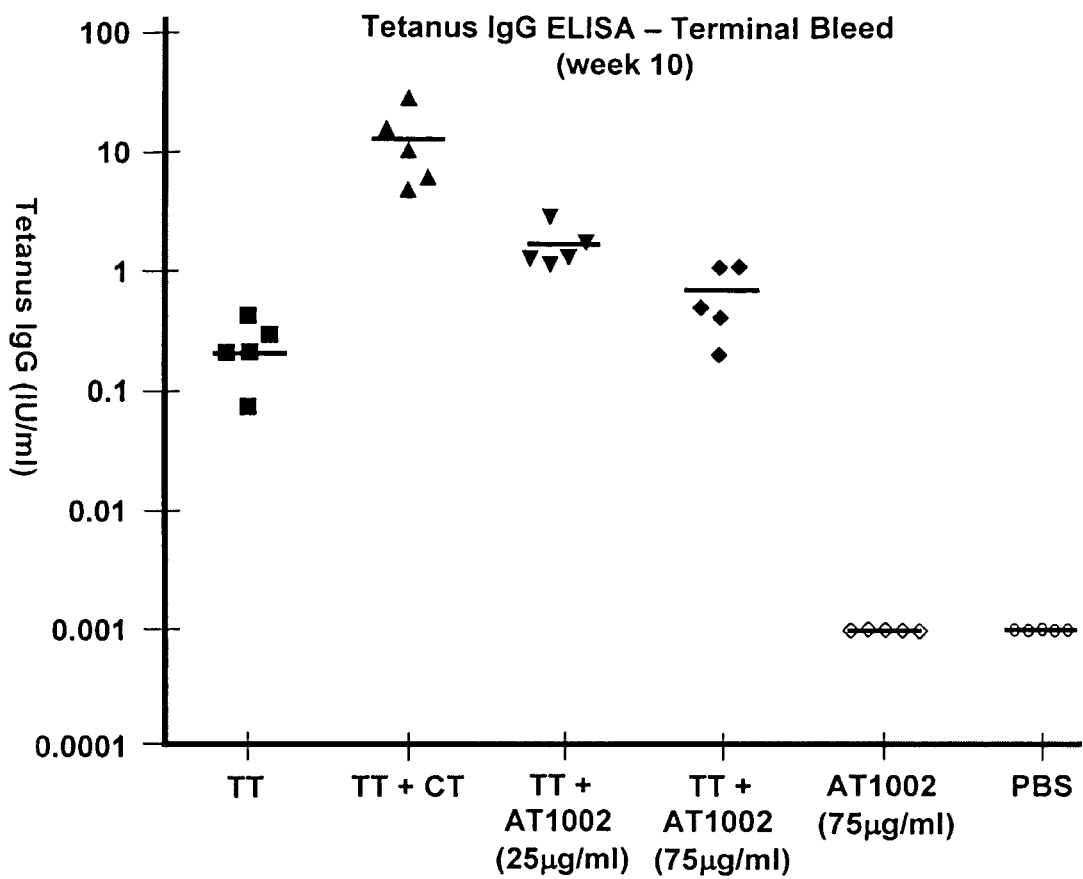
Figure 5:
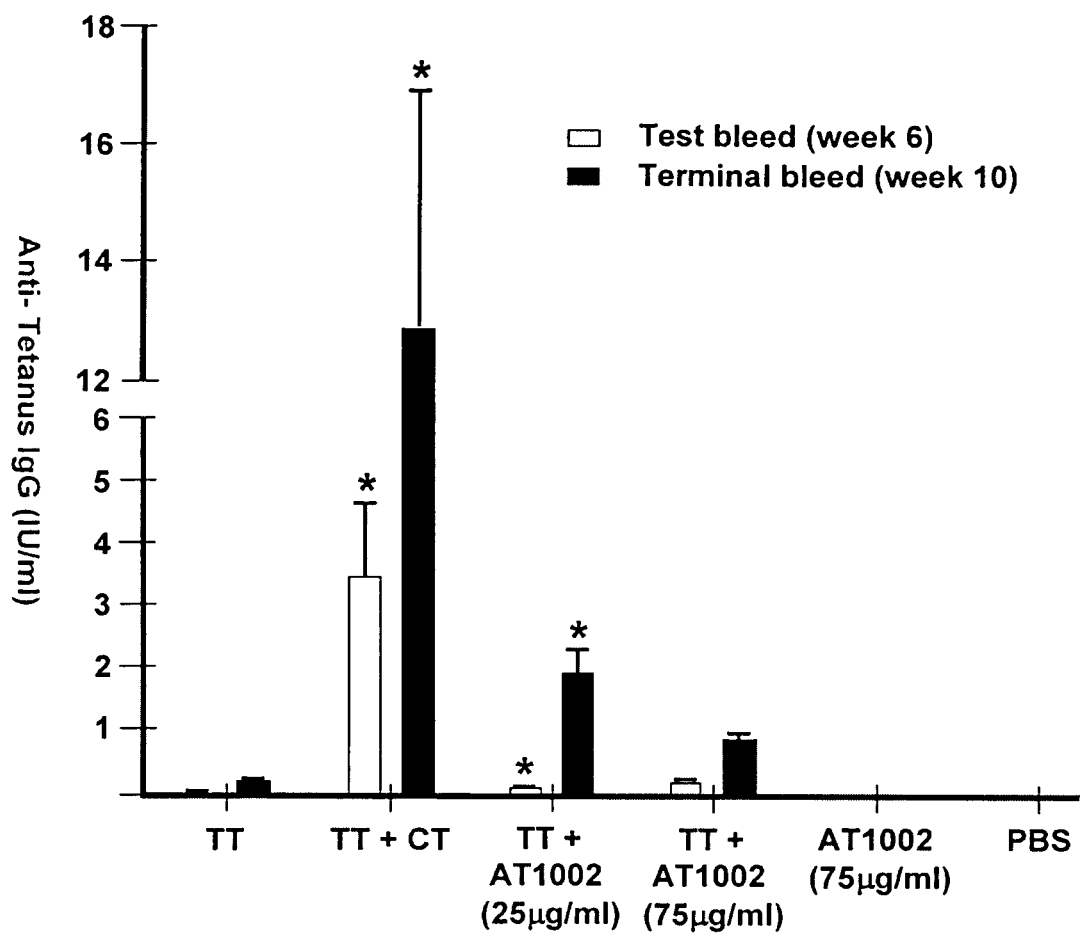
Figure 6:
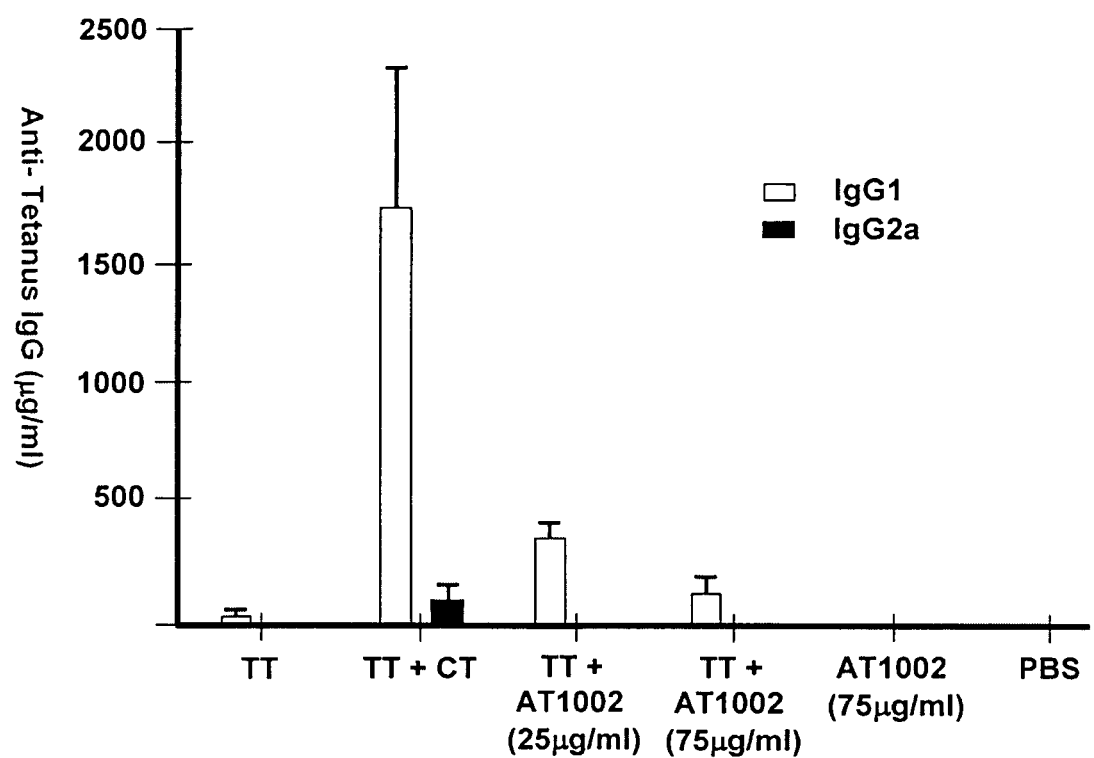
Figure 7:
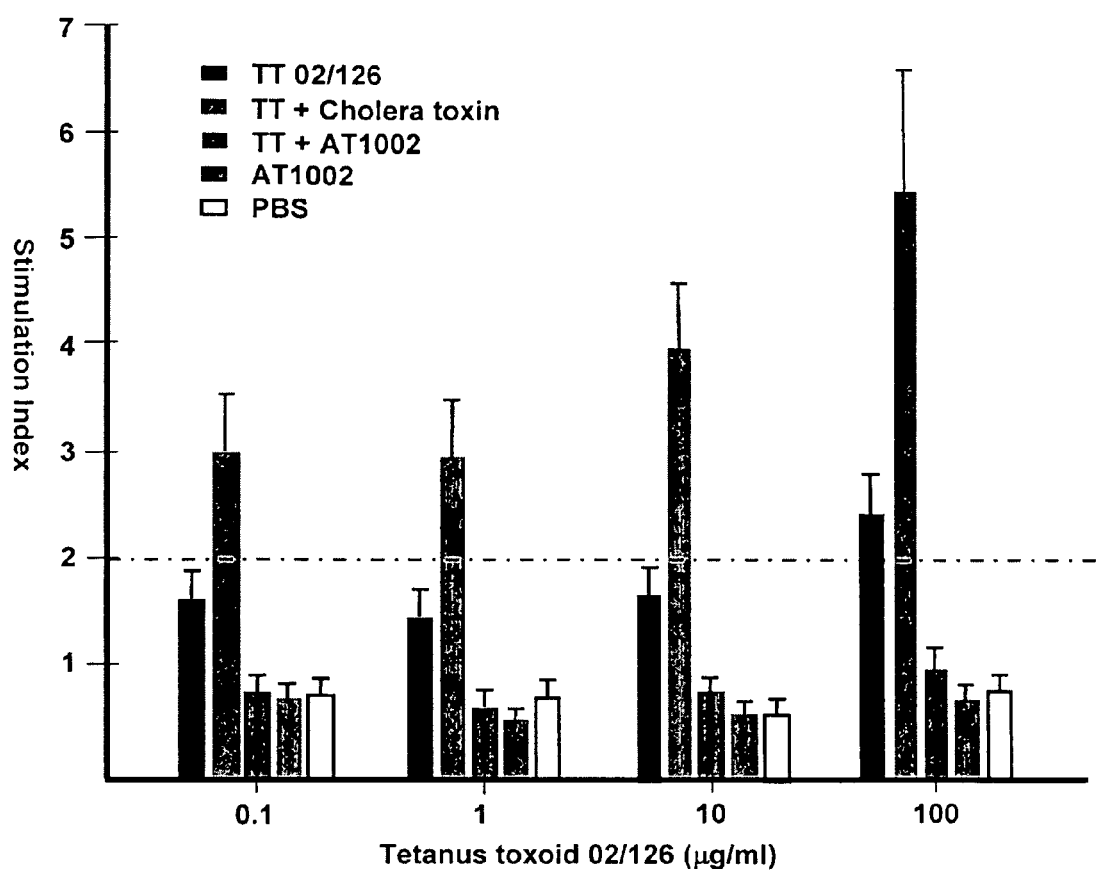
Figure 11A:
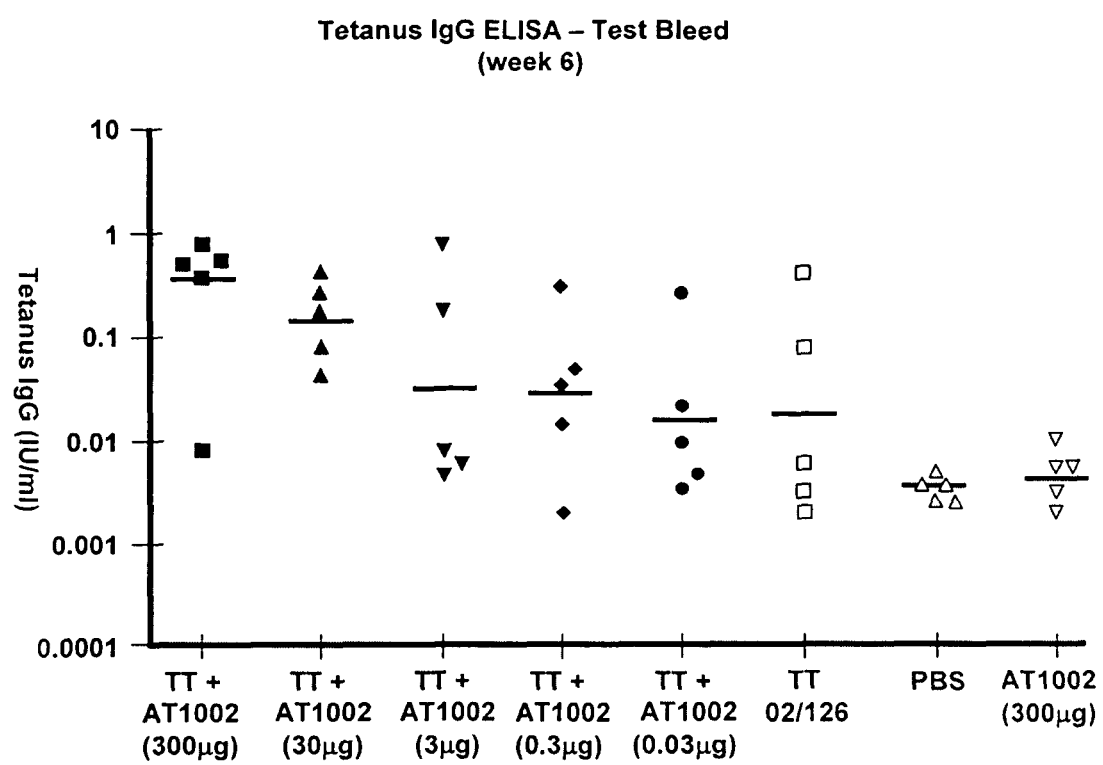
FIG. 11A shows experiment 2 tetanus IgG titers measured by ELISA in test bleeds taken from individual animal at week 6.
Figure 11B:
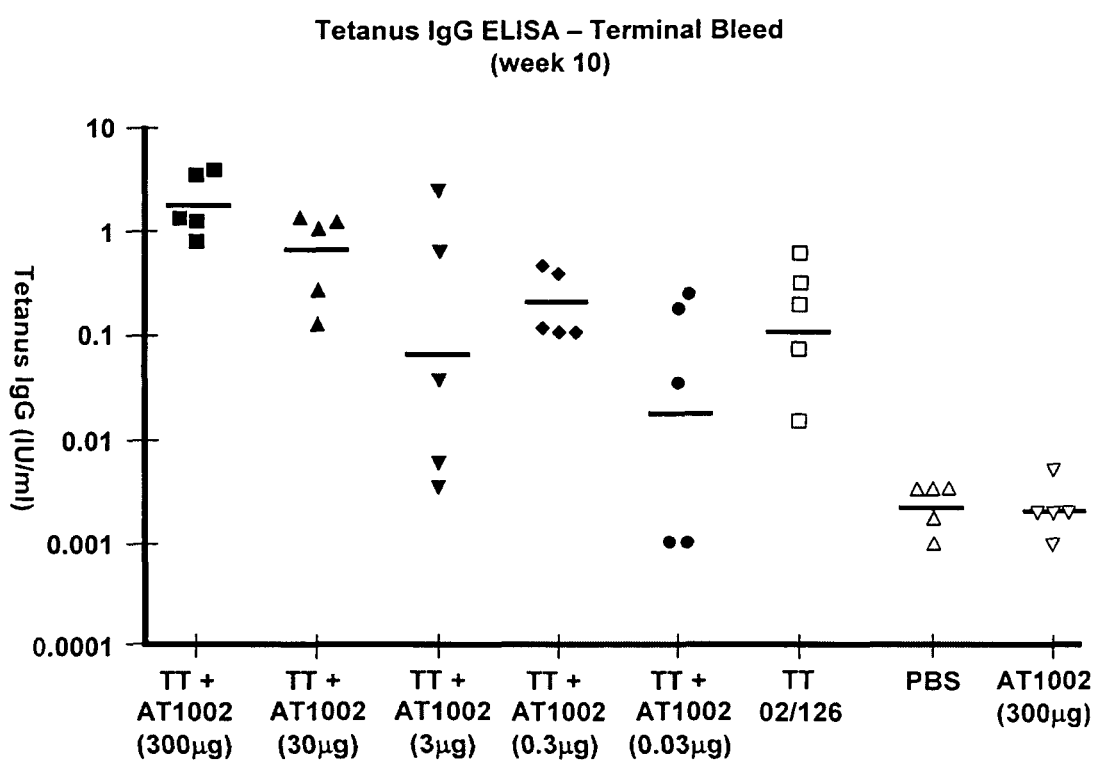
FIG. 11B shows experiment 2 tetanus IgG titers measured by ELISA in test bleeds taken from individual animal at week 10.

Total IgG antibody levels against TT were determined using an in-house Enzyme-Linked Immunosorbent assay. Results were analyzed using parallel-line analysis and antibody levels were expressed in IU/ml against in-house standard 98/572 (Tetanus potency 3.5 IU/ml). FIGS. 4A and 4B show anti-tetanus IgG titers in individual animals in experiment 1 after 6 and 10 weeks respectively. FIG. 5 shows anti-tetanus IgG titers of pooled sera for each immunization group after 6 and 10 weeks in experiment 1. Data represent the mean±SEM (n=5 per group). IgG1 and IgG2a subclasses were measured in a similar manner by comparison with appropriate purified mouse immunoglobulins, and their levels were expressed as µg/ml. FIG. 6 shows anti-tetanus IgG1 and IgG2a titers of pooled sera for each immunization group after 6 and 10 weeks in experiment 1. FIGS. 11A and 11B show anti-tetanus IgG titers in individual animals in experiment 2 after 6 and 10 weeks respectively. FIG. 12 shows anti-tetanus IgG titres of pooled sera for each immunization group after 6 and 10 weeks in experiment 2. Data represent the mean±SEM (n=5 per group).

FIGS. 19A and 19B shows anti-tetanus IgG titers in individual animals in experiment 1 after 6 and 10 weeks respectively. FIG. 20 shows anti-tetanus IgG titres of pooled sera for each immunization group after 6 and 10 weeks in experiment 3. Data represent the mean±SEM (n=6 per group except for TT group (n=5)).

Example 3

In Vivo Toxin Neutralization (TNT) Assay

The neutralizing capacity of anti-TT antibodies in pooled sera was measured in mice, using onset of paralysis as an endpoint. The neutralizing potency of the serum samples was expressed in IU/ml, measured against the WHO International Standard TE-3 antitoxin. The results from experiments 1 and 2 are shown in Tables 1 and 2 respectively.

TABLE 1

In vivo toxin neutralization assay - Experiment 1

| Group | Immunization Details | Tetanus Neutralizing Ab (IU/ml) | Tetanus IgG (ELISA, IU/ml) Pooled sera |
|---|---|---|---|
| A | TT 02/126 | 0.31 | 0.31 |
| B | TT + CT | 15.7 | 13.81 |
| C | TT + AT1002 (25 µg) | 1.85 | 2.08 |
| D | TT + AT1002 (75 µg) | ND | 0.80 |
| I | AT1002 (75 µg) | <0.07 | <0.01 |
| J | PBS | <0.07 | <0.01 |

Neutralizing antibody titers were determined by challenge with tetanus toxin in vivo as described above. Each data point represents the measurement for the pooled sera from the terminal bleed samples (week 10) obtained for each immunization treatment group. Mouse model of paralysis was used with International Standards of IU.

Immunization with TT in combination with AT1002 (25 µg) increased the protective antibody levels six-fold compared to TT treatment alone. This response was approximately 200-fold higher than the minimal protective level (0.01 IU/ml is considered protective).

TABLE 2

In vivo toxin neutralization assay - Experiment 2

| Group | Immunization Details | Tetanus Neutralizing Ab (IU/ml) | Tetanus IgG (ELISA, IU/ml) Pooled sera |
|---|---|---|---|
| A | TT + AT1002 (300 µg) | 1.10 | 2.38 |
| B | TT + AT1002 (30 µg) | <0.55 | 0.96 |
| C | TT + AT1002 (3 µg) | 0.25 | 0.61 |
| D | TT + AT1002 (0.3 µg) | <0.13* | 0.26 |
| E | TT + AT1002 (0.03 µg) | 0.07 | 0.10 |
| F | TT 02/126 | <0.18 | 0.23 |
| G | PBS | <0.02 | 0.003 |
| H | AT1002 (300 µg) | <0.02 | 0.003 |

*End point not established.

AT-1002 (top dose) increased protective antibody levels compared to immunization with TT alone. Response to immunization with TT+AT1002 (300 µg) ~100 fold higher than minimum protctive level (0.01 IU/ml considered protective).

Example 4

Spleen Cell Proliferation Assay

Single cell suspensions were prepared from spleens of individual mice and viable splenocytes ($2 \times 10^5$ per well, 96 well plate) were re-stimulated with TT (0.1-100 µg/ml). After 4 days, cells were pulsed with 0.5 mCi/well [$^3$H]-thymidine and harvested onto glass fibre filter mats. Antigen-specific proliferation was determined by measuring the radioactivity incorporated into cellular DNA. Results were expressed as stimulation indices (SI) of the mean cpm obtained from triplicate cultures in the presence of specific antigen divided by the mean cpm of triplicate cultures incubated in medium only. A SI>2 is considered positive. FIGS. 7, 13, 17 and 21 shows spleen cell proliferation following re-stimulation with TT in experiments 1, 2 and 3. Data represent the mean±SEM from three spleen cell cultures per group.

Example 5

Cytokine Assay

Figure 8A:
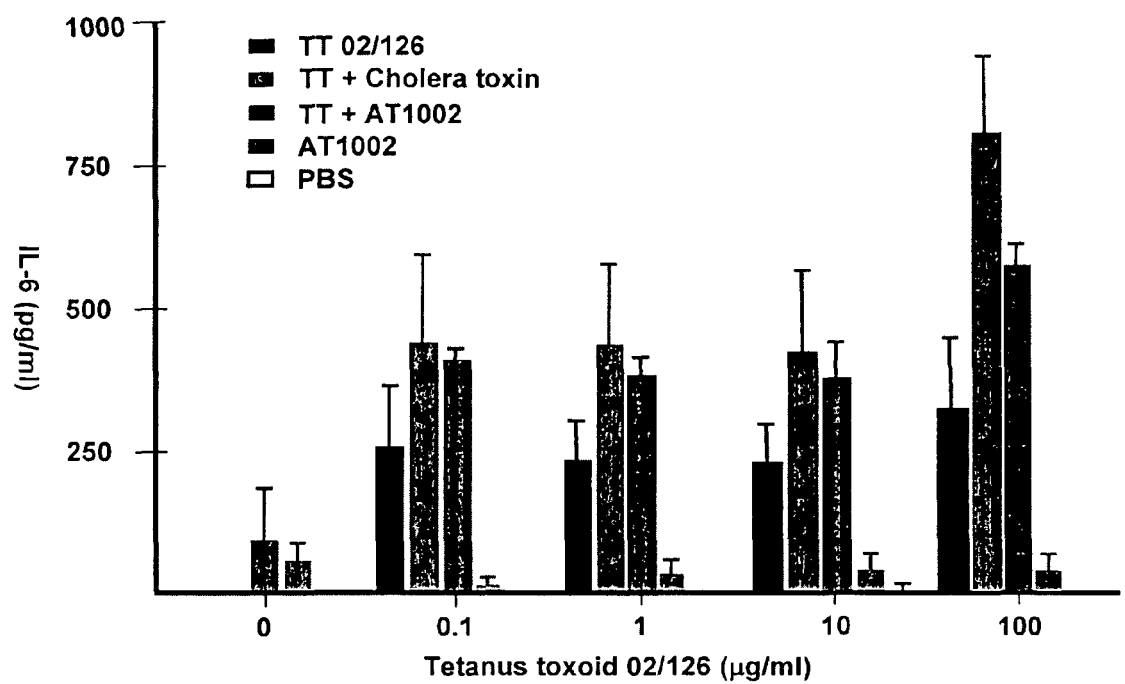
Figure 8B:
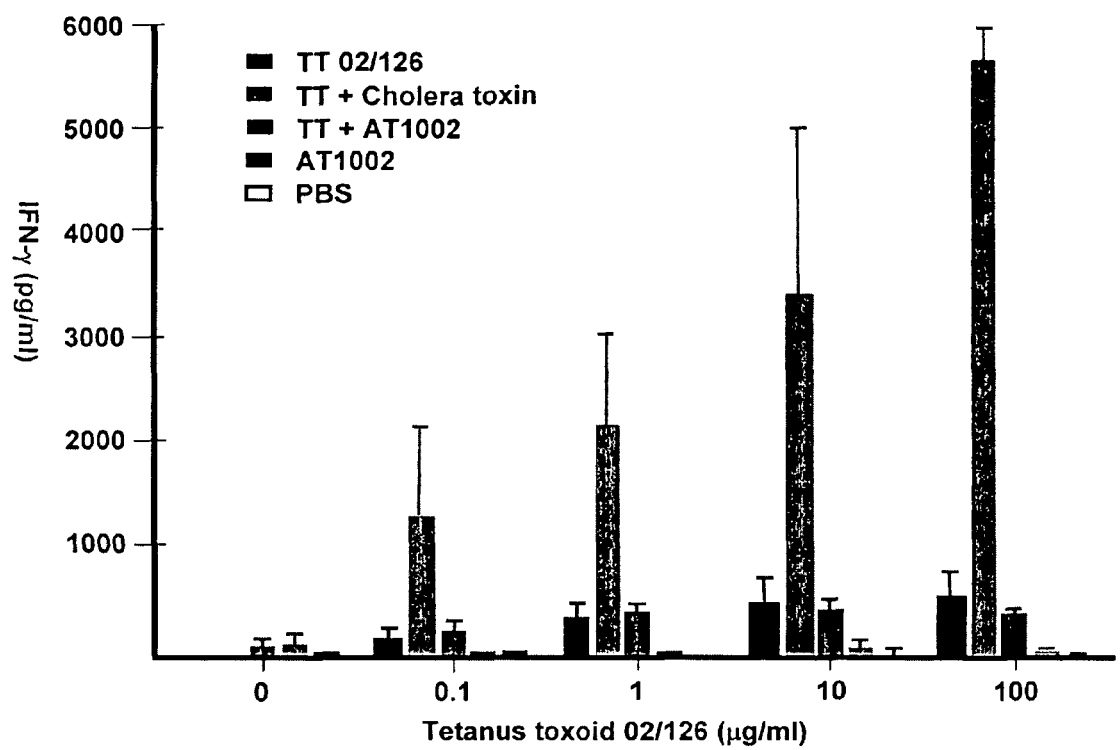

Spleen cells ($2 \times 10^6$ per well, 24 well plate) were cultured overnight prior to re-stimulation with TT for further 72 hrs. Concentrations of IFN-γ and IL-6 in culture supernatants were measured using ELISA kits (BD Biosciences), as per the manufactures instructions. Cytokine levels were expressed as µg/ml as measured against relevant cytokine standards. FIGS. 8A, 14A and 18A show production of IL-6 in splenocytes following re-stimulation with TT (0-100 µg/ml). Data represent the mean±SEM from three spleen cell cultures per group. *p<0.05, **p<0.01 vs TT alone. FIGS. 8B, 14B and 18B show production of IFN-γ in splenocytes following restimulation with TT (0-100 µg/ml) after immunization of mice with TT in the presence and absence of adjuvant. Data represent the mean±SEM from three spleen cell cultures per group.

While the invention has been described in detail, and with reference to specific embodiments thereof, it will be apparent to one of ordinary skill in the art that various changes and modifications can be made therein without departing from the spirit and scope thereof and such changes and modifications may be practiced within the scope of the appended claims. All patents and publications herein are incorporated by reference to the same extent as if each individual publication was specifically and individually indicated to be incorporated by reference in their entirety.

What is claimed is:

1. A transcutaneous dosage composition comprising a therapeutic agent and a transcutaneous absorption enhancing amount of a tight junction agonist, wherein the tight junction agonist comprises the amino acid sequence of SEQ ID NO: 198.

2. The dosage composition of claim 1, wherein the peptide comprises from about 6 to about 10 amino acid residues.

3. The dosage composition of claim 1, wherein the therapeutic agent is selected from an antibiotic, an anti-inflammatory, an analgesic, insulin, a vaccine, small molecule, peptide, protein, lipid, carbohydrate, and combinations thereof.

4. The dosage composition of claim 1, wherein the composition is an aqueous solution.

5. The dosage composition of claim 4, wherein the composition is in a saline solution.

6. The dosage composition of claim 1, wherein the composition further comprises one or more pharmaceutically acceptable excipients.

7. The dosage composition of claim 1, wherein the therapeutic agent is an antigen.

8. The dosage composition of claim 7, wherein the antigen is selected from measles virus antigens, mumps virus antigens, rubella virus antigens, *Corynebacterium diphtheriae* antigens, *Bordetella pertussis* antigens, *Clostridium telani* antigens, *Bacillus anthracis* antigens, *Haemophilus influenzae* antigens, smallpox virus antigens, and influenza virus antigens.

9. The dosage composition of claim 7 further comprising an adjuvant.

10. A method of treating an animal, comprising: administering to the animal's skin the dosage composition of claim 1.

11. The method of claim 10, wherein the animal is human.

* * * * *

SEQUENCE LISTING

<160> NUMBER OF SEQ ID NOS: 314

<210> SEQ ID NO 1
<211> LENGTH: 6
<212> TYPE: PRT
<213> ORGANISM: Unknown
<220> FEATURE:
<223> OTHER INFORMATION: Tight junction agonist peptide

<400> SEQUENCE: 1

Phe Cys Ile Gly Arg Leu
1               5

<210> SEQ ID NO 2
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met

<400> SEQUENCE: 2

Xaa Cys Ile Gly Arg Leu
1               5

<210> SEQ ID NO 3
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be Gly, Ser, Thr, Tyr, Asn or Gln

<400> SEQUENCE: 3

Phe Xaa Ile Gly Arg Leu
1               5

<210> SEQ ID NO 4
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met

<400> SEQUENCE: 4

Phe Cys Xaa Gly Arg Leu
1               5

<210> SEQ ID NO 5
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln -continued

```
<400> SEQUENCE: 5

Phe Cys Ile Xaa Arg Leu
1               5

<210> SEQ ID NO 6
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Xaa may be Lys or His

<400> SEQUENCE: 6

Phe Cys Ile Gly Xaa Leu
1               5

<210> SEQ ID NO 7
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 7

Phe Cys Ile Gly Arg Xaa
1               5

<210> SEQ ID NO 8
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met
<220> FEATURE:
<221> NAME/KEY: misc_feature
<222> LOCATION: (2)..(2)
<223> OTHER INFORMATION: Xaa may be Gly, Ser, Thr, Tyr, Asn or Gln

<400> SEQUENCE: 8

Xaa Xaa Ile Gly Arg Leu
1               5

<210> SEQ ID NO 9
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met

<400> SEQUENCE: 9
```

```
Xaa Cys Xaa Gly Arg Leu
1               5

<210> SEQ ID NO 10
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln

<400> SEQUENCE: 10

Xaa Cys Ile Xaa Arg Leu
1               5

<210> SEQ ID NO 11
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met
<220> FEATURE:
<221> NAME/KEY: misc_feature
<222> LOCATION: (5)..(5)
<223> OTHER INFORMATION: Xaa may be Lys or His

<400> SEQUENCE: 11

Xaa Cys Ile Gly Xaa Leu
1               5

<210> SEQ ID NO 12
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be Ala, Val, Leu, Ile, Pro, Trp, Tyr or
      Met
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 12

Xaa Cys Ile Gly Arg Xaa
1               5

<210> SEQ ID NO 13
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
```

```
<223> OTHER INFORMATION: Xaa may be Gly, Ser, Thr, Tyr, Asn or Gln
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met

<400> SEQUENCE: 13

Phe Xaa Xaa Gly Arg Leu
1               5

<210> SEQ ID NO 14
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be Gly, Ser, Thr, Tyr, Asn or Gln
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln

<400> SEQUENCE: 14

Phe Xaa Ile Xaa Arg Leu
1               5

<210> SEQ ID NO 15
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be Gly, Ser, Thr, Tyr, Asn or Gln
<220> FEATURE:
<221> NAME/KEY: misc_feature
<222> LOCATION: (5)..(5)
<223> OTHER INFORMATION: Xaa may be Lys or His

<400> SEQUENCE: 15

Phe Xaa Ile Gly Xaa Leu
1               5

<210> SEQ ID NO 16
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be Gly, Ser, Thr, Tyr, Asn or Gln
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 16

Phe Xaa Ile Gly Arg Xaa
1               5

<210> SEQ ID NO 17
<211> LENGTH: 6
<212> TYPE: PRT
<213> ORGANISM: Unknown
<220> FEATURE:
```

```
<223> OTHER INFORMATION: Tight junction agonist peptide
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln

<400> SEQUENCE: 17

Phe Cys Xaa Xaa Arg Leu
1               5

<210> SEQ ID NO 18
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met
<220> FEATURE:
<221> NAME/KEY: misc_feature
<222> LOCATION: (5)..(5)
<223> OTHER INFORMATION: Xaa may be Lys or His

<400> SEQUENCE: 18

Phe Cys Xaa Gly Xaa Leu
1               5

<210> SEQ ID NO 19
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Xaa may be Ala, Val, Leu, Ile, Pro, Trp or Met
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 19

Phe Cys Xaa Gly Arg Xaa
1               5

<210> SEQ ID NO 20
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln
<220> FEATURE:
<221> NAME/KEY: misc_feature
<222> LOCATION: (5)..(5)
<223> OTHER INFORMATION: Xaa may be Lys or His

<400> SEQUENCE: 20

Phe Cys Ile Xaa Xaa Leu
1               5

<210> SEQ ID NO 21
```

```
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Xaa may be Gly, Ser, Thr, Tyr, Asn, Ala or Gln
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 21

Phe Cys Ile Xaa Arg Xaa
1               5

<210> SEQ ID NO 22
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Xaa may be Lys or His
<220> FEATURE:
<221> NAME/KEY: misc_feature
<222> LOCATION: (6)..(6)
<223> OTHER INFORMATION: Xaa may be Ala, Val, Leu, Ile, Pro, Trp or Met

<400> SEQUENCE: 22

Phe Cys Ile Gly Xaa Xaa
1               5

<210> SEQ ID NO 23
<211> LENGTH: 5
<212> TYPE: PRT
<213> ORGANISM: Unknown
<220> FEATURE:
<223> OTHER INFORMATION: Tight junction agonist peptide

<400> SEQUENCE: 23

Cys Ile Gly Arg Leu
1               5

<210> SEQ ID NO 24
<211> LENGTH: 4
<212> TYPE: PRT
<213> ORGANISM: Unknown
<220> FEATURE:
<223> OTHER INFORMATION: Tight junction agonist peptide

<400> SEQUENCE: 24

Ile Gly Arg Leu
1

<210> SEQ ID NO 25
<211> LENGTH: 5
<212> TYPE: PRT
<213> ORGANISM: Unknown
<220> FEATURE:
<223> OTHER INFORMATION: Tight junction agonist peptide

<400> SEQUENCE: 25

Phe Cys Ile Gly Arg
1               5
```

```
<210> SEQ ID NO 26
<211> LENGTH: 4
<212> TYPE: PRT
<213> ORGANISM: Unknown
<220> FEATURE:
<223> OTHER INFORMATION: Tight junction agonist peptide

<400> SEQUENCE: 26

Phe Cys Ile Gly
1

<210> SEQ ID NO 27
<211> LENGTH: 6
<212> TYPE: PRT
<213> ORGANISM: Unknown
<220> FEATURE:
<223> OTHER INFORMATION: Tight junction agonist peptide

<400> SEQUENCE: 27

Ala Cys Ile Gly Arg Leu
1               5

<210> SEQ ID NO 28
<211> LENGTH: 6
<212> TYPE: PRT
<213> ORGANISM: Unknown
<220> FEATURE:
<223> OTHER INFORMATION: Tight junction agonist peptide

<400> SEQUENCE: 28

Phe Ala Ile Gly Arg Leu
1               5

<210> SEQ ID NO 29
<211> LENGTH: 6
<212> TYPE: PRT
<213> ORGANISM: Unknown
<220> FEATURE:
<223> OTHER INFORMATION: Tight junction agonist peptide

<400> SEQUENCE: 29

Phe Cys Ala Gly Arg Leu
1               5

<210> SEQ ID NO 30
<211> LENGTH: 6
<212> TYPE: PRT
<213> ORGANISM: Unknown
<220> FEATURE:
<223> OTHER INFORMATION: Tight junction agonist peptide

<400> SEQUENCE: 30

Phe Cys Ile Ala Arg Leu
1               5

<210> SEQ ID NO 31
<211> LENGTH: 6
<212> TYPE: PRT
<213> ORGANISM: Unknown
<220> FEATURE:
<223> OTHER INFORMATION: Tight junction agonist peptide

<400> SEQUENCE: 31

Phe Cys Ile Gly Ala Leu
1               5

<210> SEQ ID NO 32
<211> LENGTH: 6
```

```
<212> TYPE: PRT
<213> ORGANISM: Unknown
<220> FEATURE:
<223> OTHER INFORMATION: Tight junction agonist peptide

<400> SEQUENCE: 32

Phe Cys Ile Gly Arg Ala
1               5

<210> SEQ ID NO 33
<211> LENGTH: 6
<212> TYPE: PRT
<213> ORGANISM: Unknown
<220> FEATURE:
<223> OTHER INFORMATION: Tight junction agonist peptide

<400> SEQUENCE: 33

Phe Cys Ile Gly Arg Leu
1               5

<210> SEQ ID NO 34
<211> LENGTH: 6
<212> TYPE: PRT
<213> ORGANISM: Unknown
<220> FEATURE:
<223> OTHER INFORMATION: Tight junction agonist peptide

<400> SEQUENCE: 34

Pro Cys Ile Gly Arg Leu
1               5

<210> SEQ ID NO 35
<211> LENGTH: 6
<212> TYPE: PRT
<213> ORGANISM: Unknown
<220> FEATURE:
<223> OTHER INFORMATION: Tight junction agonist peptide

<400> SEQUENCE: 35

Gln Cys Ile Gly Arg Leu
1               5

<210> SEQ ID NO 36
<211> LENGTH: 6
<212> TYPE: PRT
<213> ORGANISM: Unknown
<220> FEATURE:
<223> OTHER INFORMATION: Tight junction agonist peptide

<400> SEQUENCE: 36

Gly Cys Ile Gly Arg Leu
1               5

<210> SEQ ID NO 37
<211> LENGTH: 6
<212> TYPE: PRT
<213> ORGANISM: Unknown
<220> FEATURE:
<223> OTHER INFORMATION: Tight junction agonist peptide

<400> SEQUENCE: 37

Thr Cys Ile Gly Arg Leu
1               5

<210> SEQ ID NO 38
<211> LENGTH: 6
<212> TYPE: PRT
<213> ORGANISM: Unknown
```

```
<220> FEATURE:
<223> OTHER INFORMATION: Tight junction agonist peptide

<400> SEQUENCE: 38

Ser Cys Ile Gly Arg Leu
1               5

<210> SEQ ID NO 39
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be sarcosine

<400> SEQUENCE: 39

Xaa Cys Ile Gly Arg Leu
1               5

<210> SEQ ID NO 40
<211> LENGTH: 6
<212> TYPE: PRT
<213> ORGANISM: Unknown
<220> FEATURE:
<223> OTHER INFORMATION: Tight junction agonist peptide

<400> SEQUENCE: 40

Asn Cys Ile Gly Arg Leu
1               5

<210> SEQ ID NO 41
<211> LENGTH: 6
<212> TYPE: PRT
<213> ORGANISM: Unknown
<220> FEATURE:
<223> OTHER INFORMATION: Tight junction agonist peptide

<400> SEQUENCE: 41

Arg Cys Ile Gly Arg Leu
1               5

<210> SEQ ID NO 42
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-beta-cyclohexyl-alanine

<400> SEQUENCE: 42

Xaa Cys Ile Gly Arg Leu
1               5

<210> SEQ ID NO 43
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be alpha-aminoisobutyric acid
```

```
<400> SEQUENCE: 43

Xaa Cys Ile Gly Arg Leu
1               5

<210> SEQ ID NO 44
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-tert-butylglycine

<400> SEQUENCE: 44

Xaa Cys Ile Gly Arg Leu
1               5

<210> SEQ ID NO 45
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-(2-thienyl)-alanine

<400> SEQUENCE: 45

Phe Xaa Ile Gly Arg Leu
1               5

<210> SEQ ID NO 46
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homoserine

<400> SEQUENCE: 46

Phe Xaa Ile Gly Arg Leu
1               5

<210> SEQ ID NO 47
<211> LENGTH: 6
<212> TYPE: PRT
<213> ORGANISM: Unknown
<220> FEATURE:
<223> OTHER INFORMATION: Tight junction agonist peptide

<400> SEQUENCE: 47

Phe Thr Ile Gly Arg Leu
1               5

<210> SEQ ID NO 48
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be 2-aminobutyric acid
```

```
<400> SEQUENCE: 48

Phe Xaa Ile Gly Arg Leu
1               5

<210> SEQ ID NO 49
<211> LENGTH: 6
<212> TYPE: PRT
<213> ORGANISM: Unknown
<220> FEATURE:
<223> OTHER INFORMATION: Tight junction agonist peptide

<400> SEQUENCE: 49

Phe Ser Ile Gly Arg Leu
1               5

<210> SEQ ID NO 50
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-methionine-sulfoxide

<400> SEQUENCE: 50

Phe Xaa Ile Gly Arg Leu
1               5

<210> SEQ ID NO 51
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-methionine-sulfone

<400> SEQUENCE: 51

Phe Xaa Ile Gly Arg Leu
1               5

<210> SEQ ID NO 52
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Cys may be d-Cys

<400> SEQUENCE: 52

Phe Cys Ile Gly Arg Leu
1               5

<210> SEQ ID NO 53
<211> LENGTH: 6
<212> TYPE: PRT
<213> ORGANISM: Unknown
<220> FEATURE:
<223> OTHER INFORMATION: Tight junction agonist peptide

<400> SEQUENCE: 53
```

```
Phe Met Ile Gly Arg Leu
1               5

<210> SEQ ID NO 54
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be norvaline

<400> SEQUENCE: 54

Xaa Cys Ile Gly Arg Leu
1               5

<210> SEQ ID NO 55
<211> LENGTH: 6
<212> TYPE: PRT
<213> ORGANISM: Unknown
<220> FEATURE:
<223> OTHER INFORMATION: Tight junction agonist peptide

<400> SEQUENCE: 55

Val Cys Ile Gly Arg Leu
1               5

<210> SEQ ID NO 56
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be homoserine

<400> SEQUENCE: 56

Xaa Cys Ile Gly Arg Leu
1               5

<210> SEQ ID NO 57
<211> LENGTH: 6
<212> TYPE: PRT
<213> ORGANISM: Unknown
<220> FEATURE:
<223> OTHER INFORMATION: Tight junction agonist peptide

<400> SEQUENCE: 57

Phe Cys Ile Gly Arg Gly
1               5

<210> SEQ ID NO 58
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Ala may be d-Ala

<400> SEQUENCE: 58

Ala Cys Ile Gly Arg Gly
1               5
```

```
<210> SEQ ID NO 59
<211> LENGTH: 6
<212> TYPE: PRT
<213> ORGANISM: Unknown
<220> FEATURE:
<223> OTHER INFORMATION: Tight junction agonist peptide

<400> SEQUENCE: 59

Ala Cys Ile Gly Arg Gly
1               5

<210> SEQ ID NO 60
<211> LENGTH: 6
<212> TYPE: PRT
<213> ORGANISM: Unknown
<220> FEATURE:
<223> OTHER INFORMATION: Tight junction agonist peptide

<400> SEQUENCE: 60

Phe Cys Ile Gly Arg Gly
1               5

<210> SEQ ID NO 61
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe

<400> SEQUENCE: 61

Phe Cys Ile Gly Arg Gly
1               5

<210> SEQ ID NO 62
<211> LENGTH: 6
<212> TYPE: PRT
<213> ORGANISM: Unknown
<220> FEATURE:
<223> OTHER INFORMATION: Tight junction agonist peptide

<400> SEQUENCE: 62

Phe Cys Ile Gly Arg Ser
1               5

<210> SEQ ID NO 63
<211> LENGTH: 6
<212> TYPE: PRT
<213> ORGANISM: Unknown
<220> FEATURE:
<223> OTHER INFORMATION: Tight junction agonist peptide

<400> SEQUENCE: 63

Phe Cys Ile Gly Arg Gln
1               5

<210> SEQ ID NO 64
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Leu may be d-Leu
```

```
<400> SEQUENCE: 64

Phe Cys Ile Gly Arg Leu
1               5

<210> SEQ ID NO 65
<211> LENGTH: 6
<212> TYPE: PRT
<213> ORGANISM: Unknown
<220> FEATURE:
<223> OTHER INFORMATION: Tight junction agonist peptide

<400> SEQUENCE: 65

Phe Cys Ile Gly Arg Lys
1               5

<210> SEQ ID NO 66
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Ala may be d-Ala

<400> SEQUENCE: 66

Phe Cys Ile Gly Arg Ala
1               5

<210> SEQ ID NO 67
<211> LENGTH: 6
<212> TYPE: PRT
<213> ORGANISM: Unknown
<220> FEATURE:
<223> OTHER INFORMATION: Tight junction agonist peptide

<400> SEQUENCE: 67

Phe Cys Ile Gly Arg Ile
1               5

<210> SEQ ID NO 68
<211> LENGTH: 6
<212> TYPE: PRT
<213> ORGANISM: Unknown
<220> FEATURE:
<223> OTHER INFORMATION: Tight junction agonist peptide

<400> SEQUENCE: 68

Phe Cys Ile Gly Arg Gly
1               5

<210> SEQ ID NO 69
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be norvaline

<400> SEQUENCE: 69

Phe Cys Ile Gly Arg Xaa
1               5
```

```
<210> SEQ ID NO 70
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be beta-alanine

<400> SEQUENCE: 70

Phe Cys Ile Gly Arg Xaa
1               5

<210> SEQ ID NO 71
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-tert-Leucine

<400> SEQUENCE: 71

Phe Cys Ile Gly Arg Xaa
1               5

<210> SEQ ID NO 72
<211> LENGTH: 6
<212> TYPE: PRT
<213> ORGANISM: Unknown
<220> FEATURE:
<223> OTHER INFORMATION: Tight junction agonist peptide

<400> SEQUENCE: 72

Phe Cys Ile Gly Arg Asp
1               5

<210> SEQ ID NO 73
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-N-methyl alanine

<400> SEQUENCE: 73

Phe Cys Ile Gly Arg Xaa
1               5

<210> SEQ ID NO 74
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-alpha-aminobutyric acid

<400> SEQUENCE: 74

Phe Cys Ile Gly Arg Xaa
1               5
```

```
<210> SEQ ID NO 75
<211> LENGTH: 6
<212> TYPE: PRT
<213> ORGANISM: Unknown
<220> FEATURE:
<223> OTHER INFORMATION: Tight junction agonist peptide

<400> SEQUENCE: 75

Phe Cys Ile Gly Arg Glu
1               5

<210> SEQ ID NO 76
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be alpha-aminoisobutyric acid

<400> SEQUENCE: 76

Phe Cys Ile Gly Arg Xaa
1               5

<210> SEQ ID NO 77
<211> LENGTH: 6
<212> TYPE: PRT
<213> ORGANISM: Unknown
<220> FEATURE:
<223> OTHER INFORMATION: Tight junction agonist peptide

<400> SEQUENCE: 77

Phe Cys Ile Gly Arg Phe
1               5

<210> SEQ ID NO 78
<211> LENGTH: 6
<212> TYPE: PRT
<213> ORGANISM: Unknown
<220> FEATURE:
<223> OTHER INFORMATION: Tight junction agonist peptide

<400> SEQUENCE: 78

Phe Cys Ile Gly Arg Asn
1               5

<210> SEQ ID NO 79
<211> LENGTH: 6
<212> TYPE: PRT
<213> ORGANISM: Unknown
<220> FEATURE:
<223> OTHER INFORMATION: Tight junction agonist peptide

<400> SEQUENCE: 79

Phe Cys Ile Gly Arg Pro
1               5

<210> SEQ ID NO 80
<211> LENGTH: 6
<212> TYPE: PRT
<213> ORGANISM: Unknown
<220> FEATURE:
<223> OTHER INFORMATION: Tight junction agonist peptide

<400> SEQUENCE: 80

Glu Cys Ile Gly Arg Leu
```

```
1               5

<210> SEQ ID NO 81
<211> LENGTH: 6
<212> TYPE: PRT
<213> ORGANISM: Unknown
<220> FEATURE:
<223> OTHER INFORMATION: Tight junction agonist peptide

<400> SEQUENCE: 81

Asp Cys Ile Gly Arg Leu
1               5

<210> SEQ ID NO 82
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-beta-cyclohexyl-alanine

<400> SEQUENCE: 82

Phe Cys Ile Gly Arg Xaa
1               5

<210> SEQ ID NO 83
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-alpha-aminobutyric acid

<400> SEQUENCE: 83

Xaa Cys Ile Gly Arg Leu
1               5

<210> SEQ ID NO 84
<211> LENGTH: 6
<212> TYPE: PRT
<213> ORGANISM: Unknown
<220> FEATURE:
<223> OTHER INFORMATION: Tight junction agonist peptide

<400> SEQUENCE: 84

Lys Cys Ile Gly Arg Leu
1               5

<210> SEQ ID NO 85
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be ornithine

<400> SEQUENCE: 85

Xaa Cys Ile Gly Arg Leu
1               5
```

```
<210> SEQ ID NO 86
<211> LENGTH: 7
<212> TYPE: PRT
<213> ORGANISM: Unknown
<220> FEATURE:
<223> OTHER INFORMATION: Tight junction agonist peptide

<400> SEQUENCE: 86

Phe Cys Ile Gly Arg Leu Cys
1               5

<210> SEQ ID NO 87
<211> LENGTH: 13
<212> TYPE: PRT
<213> ORGANISM: Unknown
<220> FEATURE:
<223> OTHER INFORMATION: Tight junction agonist peptide

<400> SEQUENCE: 87

Leu Gly Gln Gln Gln Pro Phe Pro Pro Gln Gln Pro Tyr
1               5                   10

<210> SEQ ID NO 88
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be norvaline

<400> SEQUENCE: 88

Phe Xaa Ile Gly Arg Leu
1               5

<210> SEQ ID NO 89
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-norleucine

<400> SEQUENCE: 89

Phe Xaa Ile Gly Arg Leu
1               5

<210> SEQ ID NO 90
<211> LENGTH: 6
<212> TYPE: PRT
<213> ORGANISM: Unknown
<220> FEATURE:
<223> OTHER INFORMATION: Tight junction agonist peptide

<400> SEQUENCE: 90

Pro Gly Pro Gly Arg Leu
1               5

<210> SEQ ID NO 91
<211> LENGTH: 6
<212> TYPE: PRT
<213> ORGANISM: Unknown
<220> FEATURE:
<223> OTHER INFORMATION: Tight junction agonist peptide
```

```
<400> SEQUENCE: 91

Phe Cys Ile Pro Gly Pro
1               5

<210> SEQ ID NO 92
<211> LENGTH: 6
<212> TYPE: PRT
<213> ORGANISM: Unknown
<220> FEATURE:
<223> OTHER INFORMATION: Tight junction agonist peptide

<400> SEQUENCE: 92

Phe Cys Leu Gly Arg Leu
1               5

<210> SEQ ID NO 93
<211> LENGTH: 11
<212> TYPE: PRT
<213> ORGANISM: Unknown
<220> FEATURE:
<223> OTHER INFORMATION: Tight junction agonist peptide

<400> SEQUENCE: 93

Phe Cys Ile Gly Gly Val Leu Val Gln Pro Gly
1               5                   10

<210> SEQ ID NO 94
<211> LENGTH: 6
<212> TYPE: PRT
<213> ORGANISM: Unknown
<220> FEATURE:
<223> OTHER INFORMATION: Tight junction agonist peptide

<400> SEQUENCE: 94

Gly Cys Ile Gly Arg Gly
1               5

<210> SEQ ID NO 95
<211> LENGTH: 6
<212> TYPE: PRT
<213> ORGANISM: Unknown
<220> FEATURE:
<223> OTHER INFORMATION: Tight junction agonist peptide

<400> SEQUENCE: 95

Tyr Cys Ile Gly Arg Leu
1               5

<210> SEQ ID NO 96
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Xaa may be citrulline

<400> SEQUENCE: 96

Phe Cys Ile Gly Xaa Leu
1               5

<210> SEQ ID NO 97
<211> LENGTH: 6
<212> TYPE: PRT
<213> ORGANISM: Unknown
<220> FEATURE:
```

```
<223> OTHER INFORMATION: Tight junction agonist peptide
<220> FEATURE:
<221> NAME/KEY: misc_feature
<222> LOCATION: (1)..(1)
<223> OTHER INFORMATION: Ala may be acetylated

<400> SEQUENCE: 97

Ala Cys Ile Gly Arg Leu
1               5

<210> SEQ ID NO 98
<211> LENGTH: 6
<212> TYPE: PRT
<213> ORGANISM: Unknown
<220> FEATURE:
<223> OTHER INFORMATION: Tight junction agonist peptide

<400> SEQUENCE: 98

Trp Cys Ile Gly Arg Leu
1               5

<210> SEQ ID NO 99
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Ala may be acetylated

<400> SEQUENCE: 99

Ala Cys Ile Gly Arg Ser
1               5

<210> SEQ ID NO 100
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Ala may be acetylated

<400> SEQUENCE: 100

Ala Cys Ile Gly Arg Ala
1               5

<210> SEQ ID NO 101
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-4-nitro-phenylalanine

<400> SEQUENCE: 101

Xaa Cys Ile Gly Arg Leu
1               5

<210> SEQ ID NO 102
<211> LENGTH: 6
<212> TYPE: PRT
<213> ORGANISM: Unknown
```

```
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-4-chlorophenylalanine

<400> SEQUENCE: 102

Xaa Cys Ile Gly Arg Leu
1               5

<210> SEQ ID NO 103
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-4-chlorophenylalanine

<400> SEQUENCE: 103

Phe Cys Ile Gly Arg Xaa
1               5

<210> SEQ ID NO 104
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-4-nitro-phenylalanine

<400> SEQUENCE: 104

Phe Cys Ile Gly Arg Xaa
1               5

<210> SEQ ID NO 105
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated

<400> SEQUENCE: 105

Phe Cys Ile Gly Arg Phe
1               5

<210> SEQ ID NO 106
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-1,2,3,4-tetrahydroisoquinoline-3-
      carboxylic acid

<400> SEQUENCE: 106

Xaa Cys Ile Gly Arg Leu
1               5
```

```
<210> SEQ ID NO 107
<211> LENGTH: 6
<212> TYPE: PRT
<213> ORGANISM: Unknown
<220> FEATURE:
<223> OTHER INFORMATION: Tight junction agonist peptide

<400> SEQUENCE: 107

Ser Leu Ile Gly Arg Leu
1               5

<210> SEQ ID NO 108
<211> LENGTH: 6
<212> TYPE: PRT
<213> ORGANISM: Unknown
<220> FEATURE:
<223> OTHER INFORMATION: Tight junction agonist peptide

<400> SEQUENCE: 108

Leu Arg Gly Ile Cys Phe
1               5

<210> SEQ ID NO 109
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Cys may be d-Cys

<400> SEQUENCE: 109

Leu Arg Gly Ile Cys Phe
1               5

<210> SEQ ID NO 110
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu

<400> SEQUENCE: 110

Leu Arg Gly Ile Cys Phe
1               5

<210> SEQ ID NO 111
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Arg may be d-Arg

<400> SEQUENCE: 111

Leu Arg Gly Ile Cys Phe
1               5

<210> SEQ ID NO 112
```

```
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Arg may be d-Arg

<400> SEQUENCE: 112

Phe Cys Ile Gly Arg Leu
1               5

<210> SEQ ID NO 113
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Xaa may be N-methyl-L-isoleucine

<400> SEQUENCE: 113

Phe Cys Xaa Gly Arg Leu
1               5

<210> SEQ ID NO 114
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-beta-(2-thienyl)-alanine

<400> SEQUENCE: 114

Phe Cys Ile Gly Arg Xaa
1               5

<210> SEQ ID NO 115
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-beta-(2-thienyl)-alanine

<400> SEQUENCE: 115

Xaa Cys Ile Gly Arg Leu
1               5

<210> SEQ ID NO 116
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
```

```
<223> OTHER INFORMATION: Arg may be d-Arg
<220> FEATURE:
<221> NAME/KEY: misc_feature
<222> LOCATION: (4)..(4)
<223> OTHER INFORMATION: Ile may be d-Ile
<220> FEATURE:
<221> NAME/KEY: misc_feature
<222> LOCATION: (5)..(5)
<223> OTHER INFORMATION: Cys may be d-Cys
<220> FEATURE:
<221> NAME/KEY: misc_feature
<222> LOCATION: (6)..(6)
<223> OTHER INFORMATION: Phe may be d-Phe

<400> SEQUENCE: 116

Leu Arg Gly Ile Cys Phe
1               5

<210> SEQ ID NO 117
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (5)..(5)
<223> OTHER INFORMATION: Arg may be d-Arg
<220> FEATURE:
<221> NAME/KEY: misc_feature
<222> LOCATION: (6)..(6)
<223> OTHER INFORMATION: Leu may be d-Leu

<400> SEQUENCE: 117

Phe Cys Ile Gly Arg Leu
1               5

<210> SEQ ID NO 118
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (3)..(3)
<223> OTHER INFORMATION: Ile may be d-Ile
<220> FEATURE:
<221> NAME/KEY: misc_feature
<222> LOCATION: (6)..(6)
<223> OTHER INFORMATION: Leu may be d-Leu

<400> SEQUENCE: 118

Phe Cys Ile Gly Arg Leu
1               5

<210> SEQ ID NO 119
<211> LENGTH: 6
```

```
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Ile may be d-Ile

<400> SEQUENCE: 119

Phe Cys Ile Gly Arg Leu
1               5

<210> SEQ ID NO 120
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (3)..(3)
<223> OTHER INFORMATION: Ile may be d-Ile
<220> FEATURE:
<221> NAME/KEY: misc_feature
<222> LOCATION: (5)..(5)
<223> OTHER INFORMATION: Arg may be d-Arg
<220> FEATURE:
<221> NAME/KEY: misc_feature
<222> LOCATION: (6)..(6)
<223> OTHER INFORMATION: Leu may be d-Leu

<400> SEQUENCE: 120

Phe Cys Ile Gly Arg Leu
1               5

<210> SEQ ID NO 121
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe
<220> FEATURE:
<221> NAME/KEY: misc_feature
<222> LOCATION: (3)..(3)
<223> OTHER INFORMATION: Ile may be d-Ile
<220> FEATURE:
<221> NAME/KEY: misc_feature
<222> LOCATION: (5)..(5)
<223> OTHER INFORMATION: Arg may be d-Arg
<220> FEATURE:
<221> NAME/KEY: misc_feature
<222> LOCATION: (6)..(6)
<223> OTHER INFORMATION: Leu may be d-Leu

<400> SEQUENCE: 121

Phe Cys Ile Gly Arg Leu
1               5

<210> SEQ ID NO 122
<211> LENGTH: 6
<212> TYPE: PRT
<213> ORGANISM: Unknown
<220> FEATURE:
<223> OTHER INFORMATION: Tight junction agonist peptide
<220> FEATURE:
```

```
<221> NAME/KEY: misc_feature
<222> LOCATION: (6)..(6)
<223> OTHER INFORMATION: Phe may be d-Phe

<400> SEQUENCE: 122

Leu Arg Gly Ile Cys Phe
1               5

<210> SEQ ID NO 123
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
<222> LOCATION: (4)..(4)
<223> OTHER INFORMATION: Ile may be d-Ile
<220> FEATURE:
<221> NAME/KEY: misc_feature
<222> LOCATION: (6)..(6)
<223> OTHER INFORMATION: Phe may be d-Phe

<400> SEQUENCE: 123

Leu Arg Gly Ile Cys Phe
1               5

<210> SEQ ID NO 124
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
<222> LOCATION: (4)..(4)
<223> OTHER INFORMATION: Ile may be d-Ile
<220> FEATURE:
<221> NAME/KEY: misc_feature
<222> LOCATION: (5)..(5)
<223> OTHER INFORMATION: Cys may be d-Cys
<220> FEATURE:
<221> NAME/KEY: misc_feature
<222> LOCATION: (6)..(6)
<223> OTHER INFORMATION: Phe may be d-Phe

<400> SEQUENCE: 124

Leu Arg Gly Ile Cys Phe
1               5

<210> SEQ ID NO 125
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Ile may be d-Ile

<400> SEQUENCE: 125
```

```
Leu Arg Gly Ile Cys Phe
1               5

<210> SEQ ID NO 126
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (3)..(3)
<223> OTHER INFORMATION: Ile may be d-Ile
<220> FEATURE:
<221> NAME/KEY: misc_feature
<222> LOCATION: (5)..(5)
<223> OTHER INFORMATION: Arg may be d-Arg

<400> SEQUENCE: 126

Phe Cys Ile Gly Arg Leu
1               5

<210> SEQ ID NO 127
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
<222> LOCATION: (5)..(5)
<223> OTHER INFORMATION: Cys may be d-Cys
<220> FEATURE:
<221> NAME/KEY: misc_feature
<222> LOCATION: (6)..(6)
<223> OTHER INFORMATION: Phe may be d-Phe

<400> SEQUENCE: 127

Leu Arg Gly Ile Cys Phe
1               5

<210> SEQ ID NO 128
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (4)..(4)
<223> OTHER INFORMATION: Ile may be d-Ile
<220> FEATURE:
<221> NAME/KEY: misc_feature
<222> LOCATION: (5)..(5)
```

```
<223> OTHER INFORMATION: Cys may be d-Cys
<220> FEATURE:
<221> NAME/KEY: misc_feature
<222> LOCATION: (6)..(6)
<223> OTHER INFORMATION: Phe may be d-Phe

<400> SEQUENCE: 128

Leu Arg Gly Ile Cys Phe
1               5

<210> SEQ ID NO 129
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
<222> LOCATION: (4)..(4)
<223> OTHER INFORMATION: Ile may be d-Ile
<220> FEATURE:
<221> NAME/KEY: misc_feature
<222> LOCATION: (5)..(5)
<223> OTHER INFORMATION: Cys may be d-Cys

<400> SEQUENCE: 129

Leu Arg Gly Ile Cys Phe
1               5

<210> SEQ ID NO 130
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated
<220> FEATURE:
<221> NAME/KEY: misc_feature
<222> LOCATION: (2)..(2)
<223> OTHER INFORMATION: Xaa may be homoserine

<400> SEQUENCE: 130

Phe Xaa Ile Gly Arg Ala
1               5

<210> SEQ ID NO 131
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated
<220> FEATURE:
<221> NAME/KEY: misc_feature
<222> LOCATION: (2)..(2)
<223> OTHER INFORMATION: Xaa may be homoserine

<400> SEQUENCE: 131

Phe Xaa Ile Gly Arg Ser
```

```
1               5
```

<210> SEQ ID NO 132
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated
<220> FEATURE:
<221> NAME/KEY: misc_feature
<222> LOCATION: (2)..(2)
<223> OTHER INFORMATION: Xaa may be homoserine

<400> SEQUENCE: 132

```
Phe Xaa Ile Gly Arg Phe
1               5
```

<210> SEQ ID NO 133
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Xaa may be L-1,2,3,4-tetrahydroisoquinoline-3-
      carboxylic acid

<400> SEQUENCE: 133

```
Phe Cys Ile Gly Arg Xaa
1               5
```

<210> SEQ ID NO 134
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homoserine

<400> SEQUENCE: 134

```
Phe Xaa Ile Gly Arg Phe
1               5
```

<210> SEQ ID NO 135
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-S-benzyl-cysteine

<400> SEQUENCE: 135

```
Phe Xaa Ile Gly Arg Leu
1               5
```

<210> SEQ ID NO 136
<211> LENGTH: 6
<212> TYPE: PRT
<213> ORGANISM: Unknown

```
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-S-tert-butylthio-cysteine

<400> SEQUENCE: 136

Phe Xaa Ile Gly Arg Leu
1               5

<210> SEQ ID NO 137
<211> LENGTH: 6
<212> TYPE: PRT
<213> ORGANISM: Unknown
<220> FEATURE:
<223> OTHER INFORMATION: Tight junction agonist peptide

<400> SEQUENCE: 137

Phe Leu Ile Gly Arg Leu
1               5

<210> SEQ ID NO 138
<211> LENGTH: 7
<212> TYPE: PRT
<213> ORGANISM: Unknown
<220> FEATURE:
<223> OTHER INFORMATION: Tight junction agonist peptide

<400> SEQUENCE: 138

Phe Phe Leu Ile Gly Arg Leu
1               5

<210> SEQ ID NO 139
<211> LENGTH: 6
<212> TYPE: PRT
<213> ORGANISM: Unknown
<220> FEATURE:
<223> OTHER INFORMATION: Tight junction agonist peptide

<400> SEQUENCE: 139

Phe Phe Ile Gly Arg Leu
1               5

<210> SEQ ID NO 140
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-phenylglycine

<400> SEQUENCE: 140

Phe Xaa Ile Gly Arg Leu
1               5

<210> SEQ ID NO 141
<211> LENGTH: 6
<212> TYPE: PRT
<213> ORGANISM: Unknown
<220> FEATURE:
<223> OTHER INFORMATION: Tight junction agonist peptide

<400> SEQUENCE: 141

Phe Pro Ile Gly Arg Leu
1               5
```

```
<210> SEQ ID NO 142
<211> LENGTH: 6
<212> TYPE: PRT
<213> ORGANISM: Unknown
<220> FEATURE:
<221> NAME/KEY: misc_feature
<222> LOCATION: (2)..(2)
<223> OTHER INFORMATION: Val may be d-Val
<220> FEATURE:
<223> OTHER INFORMATION: Tight junction agonist peptide

<400> SEQUENCE: 142

Phe Val Ile Gly Arg Leu
1               5

<210> SEQ ID NO 143
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-cyclohexyl-alanine

<400> SEQUENCE: 143

Phe Xaa Ile Gly Arg Leu
1               5

<210> SEQ ID NO 144
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 144

Phe Xaa Ile Gly Arg Leu
1               5

<210> SEQ ID NO 145
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-tert-butylglycine

<400> SEQUENCE: 145

Phe Xaa Ile Gly Arg Leu
1               5

<210> SEQ ID NO 146
<211> LENGTH: 4
<212> TYPE: PRT
<213> ORGANISM: Unknown
<220> FEATURE:
<223> OTHER INFORMATION: Tight junction agonist peptide

<400> SEQUENCE: 146

Phe Cys Ala Gly
```

```
<210> SEQ ID NO 147
<211> LENGTH: 4
<212> TYPE: PRT
<213> ORGANISM: Unknown
<220> FEATURE:
<223> OTHER INFORMATION: Tight junction agonist peptide

<400> SEQUENCE: 147

Phe Cys Gly Gly
1

<210> SEQ ID NO 148
<211> LENGTH: 6
<212> TYPE: PRT
<213> ORGANISM: Unknown
<220> FEATURE:
<223> OTHER INFORMATION: Tight junction agonist peptide

<400> SEQUENCE: 148

Phe Trp Ile Gly Arg Leu
1               5

<210> SEQ ID NO 149
<211> LENGTH: 6
<212> TYPE: PRT
<213> ORGANISM: Unknown
<220> FEATURE:
<223> OTHER INFORMATION: Tight junction agonist peptide

<400> SEQUENCE: 149

Phe His Ile Gly Arg Leu
1               5

<210> SEQ ID NO 150
<211> LENGTH: 6
<212> TYPE: PRT
<213> ORGANISM: Unknown
<220> FEATURE:
<223> OTHER INFORMATION: Tight junction agonist peptide

<400> SEQUENCE: 150

Phe Pro Ile Gly Arg Leu
1               5

<210> SEQ ID NO 151
<211> LENGTH: 6
<212> TYPE: PRT
<213> ORGANISM: Unknown
<220> FEATURE:
<223> OTHER INFORMATION: Tight junction agonist peptide

<400> SEQUENCE: 151

Phe Asp Ile Gly Arg Leu
1               5

<210> SEQ ID NO 152
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-1,4-diaminobutyric acid

<400> SEQUENCE: 152
```

```
Phe Xaa Ile Gly Arg Leu
1               5

<210> SEQ ID NO 153
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (5)..(5)
<223> OTHER INFORMATION: Arg may be d-Arg

<400> SEQUENCE: 153

Phe Cys Ile Gly Arg Leu
1               5

<210> SEQ ID NO 154
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu

<400> SEQUENCE: 154

Leu Arg Gly Ile Cys Phe
1               5

<210> SEQ ID NO 155
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg

<400> SEQUENCE: 155

Leu Arg Gly Ile Cys Phe
1               5

<210> SEQ ID NO 156
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
```

<222> LOCATION: (6)..(6)
<223> OTHER INFORMATION: Phe may be d-Phe

<400> SEQUENCE: 156

Leu Arg Gly Ile Cys Phe
1               5

<210> SEQ ID NO 157
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu
<220> FEATURE:
<221> NAME/KEY: misc_feature
<222> LOCATION: (2)..(2)
<223> OTHER INFORMATION: Arg may be d-Arg
<220> FEATURE:
<221> NAME/KEY: misc_feature
<222> LOCATION: (5)..(5)
<223> OTHER INFORMATION: Cys may be d-Cys

<400> SEQUENCE: 157

Leu Arg Gly Ile Cys Phe
1               5

<210> SEQ ID NO 158
<211> LENGTH: 7
<212> TYPE: PRT
<213> ORGANISM: Unknown
<220> FEATURE:
<223> OTHER INFORMATION: Tight junction agonist peptide

<400> SEQUENCE: 158

Gly Phe Cys Ile Gly Arg Leu
1               5

<210> SEQ ID NO 159
<211> LENGTH: 6
<212> TYPE: PRT
<213> ORGANISM: Unknown
<220> FEATURE:
<223> OTHER INFORMATION: Tight junction agonist peptide

<400> SEQUENCE: 159

Phe Leu Ile Gly Arg Leu
1               5

<210> SEQ ID NO 160
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated

<400> SEQUENCE: 160

Phe Cys Ile Gly Arg Leu
1               5

<210> SEQ ID NO 161
<211> LENGTH: 6
<212> TYPE: PRT

```
<213> ORGANISM: Unknown
<220> FEATURE:
<223> OTHER INFORMATION: Tight junction agonist peptide

<400> SEQUENCE: 161

Phe Phe Ile Gly Arg Leu
1               5

<210> SEQ ID NO 162
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-(R,S)-3,4-cis-methanoproline

<400> SEQUENCE: 162

Phe Xaa Ile Gly Arg Leu
1               5

<210> SEQ ID NO 163
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-1,3-diaminopropionic acid

<400> SEQUENCE: 163

Phe Xaa Ile Gly Arg Leu
1               5

<210> SEQ ID NO 164
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-S-acetamidomethyl-penicillamine

<400> SEQUENCE: 164

Phe Xaa Ile Gly Arg Leu
1               5

<210> SEQ ID NO 165
<211> LENGTH: 6
<212> TYPE: PRT
<213> ORGANISM: Unknown
<220> FEATURE:
<223> OTHER INFORMATION: Tight junction agonist peptide

<400> SEQUENCE: 165

Leu Arg Gly Gly Arg Leu
1               5

<210> SEQ ID NO 166
<211> LENGTH: 6
<212> TYPE: PRT
<213> ORGANISM: Unknown
<220> FEATURE:
<223> OTHER INFORMATION: Tight junction agonist peptide
```

```
<220> FEATURE:
<221> NAME/KEY: misc_feature
<222> LOCATION: (1)..(1)
<223> OTHER INFORMATION: Phe may be d-Phe

<400> SEQUENCE: 166

Phe Cys Ile Gly Arg Leu
1               5

<210> SEQ ID NO 167
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be d-Phe
<220> FEATURE:
<221> NAME/KEY: misc_feature
<222> LOCATION: (2)..(2)
<223> OTHER INFORMATION: Cys may be d-Cys
<220> FEATURE:
<221> NAME/KEY: misc_feature
<222> LOCATION: (3)..(3)
<223> OTHER INFORMATION: Ile may be d-Ile
<220> FEATURE:
<221> NAME/KEY: misc_feature
<222> LOCATION: (5)..(5)
<223> OTHER INFORMATION: Arg may be d-Arg
<220> FEATURE:
<221> NAME/KEY: misc_feature
<222> LOCATION: (6)..(6)
<223> OTHER INFORMATION: Leu may be d-Leu

<400> SEQUENCE: 167

Phe Cys Ile Gly Arg Leu
1               5

<210> SEQ ID NO 168
<211> LENGTH: 6
<212> TYPE: PRT
<213> ORGANISM: Unknown
<220> FEATURE:
<223> OTHER INFORMATION: Tight junction agonist peptide

<400> SEQUENCE: 168

Phe Arg Ile Gly Arg Leu
1               5

<210> SEQ ID NO 169
<211> LENGTH: 6
<212> TYPE: PRT
<213> ORGANISM: Unknown
<220> FEATURE:
<223> OTHER INFORMATION: Tight junction agonist peptide

<400> SEQUENCE: 169

Phe Gly Ile Gly Arg Leu
1               5

<210> SEQ ID NO 170
<211> LENGTH: 6
<212> TYPE: PRT
<213> ORGANISM: Unknown
<220> FEATURE:
<223> OTHER INFORMATION: Tight junction agonist peptide

<400> SEQUENCE: 170

Phe Gln Ile Gly Arg Leu
```

```
<210> SEQ ID NO 171
<211> LENGTH: 6
<212> TYPE: PRT
<213> ORGANISM: Unknown
<220> FEATURE:
<223> OTHER INFORMATION: Tight junction agonist peptide

<400> SEQUENCE: 171

Phe Glu Ile Gly Arg Leu
1               5

<210> SEQ ID NO 172
<211> LENGTH: 6
<212> TYPE: PRT
<213> ORGANISM: Unknown
<220> FEATURE:
<223> OTHER INFORMATION: Tight junction agonist peptide

<400> SEQUENCE: 172

Phe Lys Ile Gly Arg Leu
1               5

<210> SEQ ID NO 173
<211> LENGTH: 6
<212> TYPE: PRT
<213> ORGANISM: Unknown
<220> FEATURE:
<223> OTHER INFORMATION: Tight junction agonist peptide

<400> SEQUENCE: 173

Phe Asn Ile Gly Arg Leu
1               5

<210> SEQ ID NO 174
<211> LENGTH: 6
<212> TYPE: PRT
<213> ORGANISM: Unknown
<220> FEATURE:
<223> OTHER INFORMATION: Tight junction agonist peptide

<400> SEQUENCE: 174

Phe Tyr Ile Gly Arg Leu
1               5

<210> SEQ ID NO 175
<211> LENGTH: 6
<212> TYPE: PRT
<213> ORGANISM: Unknown
<220> FEATURE:
<223> OTHER INFORMATION: Tight junction agonist peptide

<400> SEQUENCE: 175

Phe Leu Ile Gly Arg Leu
1               5

<210> SEQ ID NO 176
<211> LENGTH: 6
<212> TYPE: PRT
<213> ORGANISM: Unknown
<220> FEATURE:
<223> OTHER INFORMATION: Tight junction agonist peptide

<400> SEQUENCE: 176

Phe Val Ile Gly Arg Leu
1               5
```

```
<210> SEQ ID NO 177
<211> LENGTH: 6
<212> TYPE: PRT
<213> ORGANISM: Unknown
<220> FEATURE:
<223> OTHER INFORMATION: Tight junction agonist peptide

<400> SEQUENCE: 177

Phe Ile Ile Gly Arg Leu
1               5

<210> SEQ ID NO 178
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homocysteine

<400> SEQUENCE: 178

Phe Xaa Ile Gly Arg Leu
1               5

<210> SEQ ID NO 179
<211> LENGTH: 6
<212> TYPE: PRT
<213> ORGANISM: Unknown
<220> FEATURE:
<223> OTHER INFORMATION: Tight junction agonist peptide

<400> SEQUENCE: 179

Ser Leu Ile Gly Arg Leu
1               5

<210> SEQ ID NO 180
<211> LENGTH: 6
<212> TYPE: PRT
<213> ORGANISM: Unknown
<220> FEATURE:
<223> OTHER INFORMATION: Tight junction agonist peptide

<400> SEQUENCE: 180

Phe Cys Ala Gly Met Ser
1               5

<210> SEQ ID NO 181
<211> LENGTH: 6
<212> TYPE: PRT
<213> ORGANISM: Unknown
<220> FEATURE:
<223> OTHER INFORMATION: Tight junction agonist peptide

<400> SEQUENCE: 181

Phe Cys Val Gly Met Ser
1               5

<210> SEQ ID NO 182
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-(2-pyridyl)-alanine
```

```
<400> SEQUENCE: 182

Phe Xaa Ile Gly Arg Leu
1               5

<210> SEQ ID NO 183
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (3)..(3)
<223> OTHER INFORMATION: Ile may be d-Ile

<400> SEQUENCE: 183

Phe Leu Ile Gly Arg Leu
1               5

<210> SEQ ID NO 184
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated

<400> SEQUENCE: 184

Phe Leu Ile Gly Arg Leu
1               5

<210> SEQ ID NO 185
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Leu may be d-Leu

<400> SEQUENCE: 185

Phe Leu Ile Gly Arg Leu
1               5

<210> SEQ ID NO 186
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Ile may be d-Ile

<400> SEQUENCE: 186

Leu Arg Gly Ile Leu Phe
1               5

<210> SEQ ID NO 187
<211> LENGTH: 6
<212> TYPE: PRT
<213> ORGANISM: Unknown
<220> FEATURE:
```

```
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be an L-alpha-aminobutyric acid dimer

<400> SEQUENCE: 187

Phe Xaa Ile Gly Arg Leu
1               5

<210> SEQ ID NO 188
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be dehydro-leucine

<400> SEQUENCE: 188

Phe Xaa Ile Gly Arg Leu
1               5

<210> SEQ ID NO 189
<211> LENGTH: 6
<212> TYPE: PRT
<213> ORGANISM: Unknown
<220> FEATURE:
<223> OTHER INFORMATION: Tight junction agonist peptide

<400> SEQUENCE: 189

Leu Arg Gly Ile Leu Phe
1               5

<210> SEQ ID NO 190
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated
<220> FEATURE:
<221> NAME/KEY: misc_feature
<222> LOCATION: (2)..(2)
<223> OTHER INFORMATION: Xaa may be homoserine

<400> SEQUENCE: 190

Phe Xaa Ile Gly Arg
1               5

<210> SEQ ID NO 191
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homoserine
<220> FEATURE:
<221> NAME/KEY: misc_feature
<222> LOCATION: (3)..(3)
<223> OTHER INFORMATION: Ile may be d-Ile

<400> SEQUENCE: 191
```

```
Phe Xaa Ile Gly Arg
1               5

<210> SEQ ID NO 192
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Phe may be acetylated
<220> FEATURE:
<221> NAME/KEY: misc_feature
<222> LOCATION: (2)..(2)
<223> OTHER INFORMATION: Xaa may be homoserine

<400> SEQUENCE: 192

Phe Xaa Ile Gly Arg Leu
1               5

<210> SEQ ID NO 193
<211> LENGTH: 5
<212> TYPE: PRT
<213> ORGANISM: Unknown
<220> FEATURE:
<223> OTHER INFORMATION: Tight junction agonist peptide

<400> SEQUENCE: 193

Phe Leu Ile Gly Arg
1               5

<210> SEQ ID NO 194
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homoserine
<220> FEATURE:
<221> NAME/KEY: misc_feature
<222> LOCATION: (3)..(3)
<223> OTHER INFORMATION: Ile may be d-Ile

<400> SEQUENCE: 194

Phe Xaa Ile Gly Arg Leu
1               5

<210> SEQ ID NO 195
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-4-cyano-phenylalanine

<400> SEQUENCE: 195

Xaa Phe Ile Gly Arg Leu
1               5

<210> SEQ ID NO 196
<211> LENGTH: 6
<212> TYPE: PRT
<213> ORGANISM: Unknown
```

```
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Xaa may be L-3-methyl-phenylalanine

<400> SEQUENCE: 196

Xaa Phe Ile Gly Arg Leu
1               5

<210> SEQ ID NO 197
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-cyclopropyl-alanine

<400> SEQUENCE: 197

Phe Xaa Ile Gly Arg Leu
1               5

<210> SEQ ID NO 198
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 198

Phe Xaa Ile Gly Arg
1               5

<210> SEQ ID NO 199
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be D-allylglycine

<400> SEQUENCE: 199

Phe Xaa Ile Gly Arg
1               5

<210> SEQ ID NO 200
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-propargylglycine

<400> SEQUENCE: 200

Phe Xaa Ile Gly Arg
1               5
```

```
<210> SEQ ID NO 201
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 201

Phe Xaa Ile Thr Arg Leu
1               5

<210> SEQ ID NO 202
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 202

Phe Xaa Ile Leu Arg Leu
1               5

<210> SEQ ID NO 203
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 203

Phe Xaa Ile Ile Arg Leu
1               5

<210> SEQ ID NO 204
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 204

Phe Xaa Ile Ala Arg Leu
1               5

<210> SEQ ID NO 205
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine
```

-continued

```
<400> SEQUENCE: 205

Phe Xaa Ile Pro Arg Leu
1               5

<210> SEQ ID NO 206
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 206

Phe Xaa Pro Gly Arg Leu
1               5

<210> SEQ ID NO 207
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 207

Phe Xaa Phe Gly Arg Leu
1               5

<210> SEQ ID NO 208
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 208

Phe Xaa Thr Gly Arg Leu
1               5

<210> SEQ ID NO 209
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 209

Phe Xaa Leu Gly Arg Leu
1               5

<210> SEQ ID NO 210
<211> LENGTH: 6
<212> TYPE: PRT
<213> ORGANISM: Unknown
<220> FEATURE:
<223> OTHER INFORMATION: Tight junction agonist peptide
```

```
<220> FEATURE:
<221> NAME/KEY: misc_feature
<222> LOCATION: (2)..(2)
<223> OTHER INFORMATION: Xaa may be L-allylglycine

<400> SEQUENCE: 210

Phe Xaa Ser Gly Arg Leu
1               5

<210> SEQ ID NO 211
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 211

Phe Xaa Phe Gly Arg Leu
1               5

<210> SEQ ID NO 212
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 212

Phe Xaa Val Gly Arg Leu
1               5

<210> SEQ ID NO 213
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 213

Phe Xaa Gly Gly Arg Leu
1               5

<210> SEQ ID NO 214
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 214

Phe Xaa Ala Gly Arg Leu
1               5

<210> SEQ ID NO 215
```

```
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 215

Met Xaa Ile Gly Arg Leu
1               5

<210> SEQ ID NO 216
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 216

Gln Xaa Ile Gly Arg Leu
1               5

<210> SEQ ID NO 217
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 217

Leu Xaa Ile Gly Arg Leu
1               5

<210> SEQ ID NO 218
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 218

Ser Xaa Ile Gly Arg Leu
1               5

<210> SEQ ID NO 219
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 219
```

```
Thr Xaa Ile Gly Arg Leu
1               5

<210> SEQ ID NO 220
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 220

Glu Xaa Ile Gly Arg Leu
1               5

<210> SEQ ID NO 221
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 221

Val Xaa Ile Gly Arg Leu
1               5

<210> SEQ ID NO 222
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 222

Tyr Xaa Ile Gly Arg Leu
1               5

<210> SEQ ID NO 223
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 223

Gly Xaa Ile Gly Arg Leu
1               5

<210> SEQ ID NO 224
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
```

```
<222> LOCATION: (2)..(2)
<223> OTHER INFORMATION: Xaa may be L-allylglycine

<400> SEQUENCE: 224

Asp Xaa Ile Gly Arg Leu
1               5

<210> SEQ ID NO 225
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 225

Trp Xaa Ile Gly Arg Leu
1               5

<210> SEQ ID NO 226
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 226

Lys Xaa Ile Gly Arg Leu
1               5

<210> SEQ ID NO 227
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 227

Ala Xaa Ile Gly Arg Leu
1               5

<210> SEQ ID NO 228
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 228

His Xaa Ile Gly Arg Leu
1               5

<210> SEQ ID NO 229
<211> LENGTH: 6
<212> TYPE: PRT
```

```
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 229

Pro Xaa Ile Gly Arg Leu
 1               5

<210> SEQ ID NO 230
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 230

Arg Xaa Ile Gly Arg Leu
 1               5

<210> SEQ ID NO 231
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 231

Ile Xaa Ile Gly Arg Leu
 1               5

<210> SEQ ID NO 232
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 232

Met Xaa Ile Gly Arg Leu
 1               5

<210> SEQ ID NO 233
<211> LENGTH: 5
<212> TYPE: PRT
<213> ORGANISM: Unknown
<220> FEATURE:
<223> OTHER INFORMATION: Tight junction agonist peptide

<400> SEQUENCE: 233

Tyr Ile Gly Ser Arg
 1               5

<210> SEQ ID NO 234
<211> LENGTH: 5
```

```
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-(2-furyl)-alanine

<400> SEQUENCE: 234

Phe Xaa Ile Gly Arg
1               5

<210> SEQ ID NO 235
<211> LENGTH: 5
<212> TYPE: PRT
<213> ORGANISM: Unknown
<220> FEATURE:
<223> OTHER INFORMATION: Tight junction agonist peptide

<400> SEQUENCE: 235

Phe Thr Ile Gly Arg
1               5

<210> SEQ ID NO 236
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-styryl-alanine

<400> SEQUENCE: 236

Phe Xaa Ile Gly Arg Leu
1               5

<210> SEQ ID NO 237
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be homocitrulline

<400> SEQUENCE: 237

Phe Xaa Ile Gly Arg Leu
1               5

<210> SEQ ID NO 238
<211> LENGTH: 6
<212> TYPE: PRT
<213> ORGANISM: Unknown
<220> FEATURE:
<223> OTHER INFORMATION: Tight junction agonist peptide

<400> SEQUENCE: 238

Phe Thr Ile Gly Arg Leu
1               5

<210> SEQ ID NO 239
<211> LENGTH: 6
<212> TYPE: PRT
<213> ORGANISM: Unknown
<220> FEATURE:
```

```
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-beta-(2-furyl)-alanine

<400> SEQUENCE: 239

Phe Xaa Ile Gly Arg Leu
1               5

<210> SEQ ID NO 240
<211> LENGTH: 5
<212> TYPE: PRT
<213> ORGANISM: Unknown
<220> FEATURE:
<223> OTHER INFORMATION: Tight junction agonist peptide

<400> SEQUENCE: 240

Phe Ile Gly Arg Leu
1               5

<210> SEQ ID NO 241
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 241

Phe Xaa Ile Gly Arg Leu
1               5

<210> SEQ ID NO 242
<211> LENGTH: 5
<212> TYPE: PRT
<213> ORGANISM: Unknown
<220> FEATURE:
<223> OTHER INFORMATION: Tight junction agonist peptide

<400> SEQUENCE: 242

Arg Gly Ile Leu Phe
1               5

<210> SEQ ID NO 243
<211> LENGTH: 4
<212> TYPE: PRT
<213> ORGANISM: Unknown
<220> FEATURE:
<223> OTHER INFORMATION: Tight junction agonist peptide

<400> SEQUENCE: 243

Gly Ile Leu Phe
1

<210> SEQ ID NO 244
<211> LENGTH: 5
<212> TYPE: PRT
<213> ORGANISM: Unknown
<220> FEATURE:
<223> OTHER INFORMATION: Tight junction agonist peptide

<400> SEQUENCE: 244

Leu Arg Gly Ile Leu
1               5
```

```
<210> SEQ ID NO 245
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (4)..(4)
<223> OTHER INFORMATION: Ile may be d-Ile

<400> SEQUENCE: 245

Leu Arg Gly Ile Leu Phe
1               5

<210> SEQ ID NO 246
<211> LENGTH: 6
<212> TYPE: PRT
<213> ORGANISM: Unknown
<220> FEATURE:
<223> OTHER INFORMATION: Tight junction agonist peptide

<400> SEQUENCE: 246

Leu Arg Gly Phe Leu Phe
1               5

<210> SEQ ID NO 247
<211> LENGTH: 6
<212> TYPE: PRT
<213> ORGANISM: Unknown
<220> FEATURE:
<223> OTHER INFORMATION: Tight junction agonist peptide

<400> SEQUENCE: 247

Leu Arg Gly Leu Leu Phe
1               5

<210> SEQ ID NO 248
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (6)..(6)
<223> OTHER INFORMATION: Phe may be d-Phe

<400> SEQUENCE: 248

Leu Arg Gly Ile Leu Phe
1               5

<210> SEQ ID NO 249
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Leu may be d-Leu

<400> SEQUENCE: 249

Leu Arg Gly Ile Leu Phe
1               5

<210> SEQ ID NO 250
<211> LENGTH: 6
```

```
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Arg may be d-Arg

<400> SEQUENCE: 250

Leu Arg Gly Ile Leu Phe
1               5

<210> SEQ ID NO 251
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
<223> OTHER INFORMATION: Leu may be d-Leu

<400> SEQUENCE: 251

Leu Arg Gly Ile Leu Phe
1               5

<210> SEQ ID NO 252
<211> LENGTH: 6
<212> TYPE: PRT
<213> ORGANISM: Unknown
<220> FEATURE:
<223> OTHER INFORMATION: Tight junction agonist peptide

<400> SEQUENCE: 252

Phe Arg Gly Ile Leu Phe
1               5

<210> SEQ ID NO 253
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (5)..(5)
<223> OTHER INFORMATION: Xaa may be L-allylglycine

<400> SEQUENCE: 253

Leu Arg Gly Ile Xaa Phe
1               5

<210> SEQ ID NO 254
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 254

Phe Xaa Ile Gly Arg His
1               5

<210> SEQ ID NO 255
```

```
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 255

Phe Xaa Ile Gly Arg Asp
1               5

<210> SEQ ID NO 256
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 256

Phe Xaa Ile Gly Arg Arg
1               5

<210> SEQ ID NO 257
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 257

Phe Xaa Ile Gly Arg Phe
1               5

<210> SEQ ID NO 258
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 258

Phe Xaa Ile Gly Arg Ala
1               5

<210> SEQ ID NO 259
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 259
```

```
Phe Xaa Ile Gly Arg Gly
1               5
```

<210> SEQ ID NO 260
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 260

```
Phe Xaa Ile Gly Arg Gln
1               5
```

<210> SEQ ID NO 261
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 261

```
Phe Xaa Ile Gly Arg Glu
1               5
```

<210> SEQ ID NO 262
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 262

```
Phe Xaa Ile Gly Arg Thr
1               5
```

<210> SEQ ID NO 263
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 263

```
Phe Xaa Ile Gly Arg Tyr
1               5
```

<210> SEQ ID NO 264
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature

```
<222> LOCATION: (2)..(2)
<223> OTHER INFORMATION: Xaa may be L-allylglycine

<400> SEQUENCE: 264

Phe Xaa Ile Gly Arg Ser
1               5

<210> SEQ ID NO 265
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 265

Phe Xaa Ile Gly Arg Asn
1               5

<210> SEQ ID NO 266
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 266

Phe Xaa Ile Gly Arg Met
1               5

<210> SEQ ID NO 267
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 267

Phe Xaa Ile Gly Arg Lys
1               5

<210> SEQ ID NO 268
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 268

Phe Xaa Ile Gly Arg Ile
1               5

<210> SEQ ID NO 269
<211> LENGTH: 6
<212> TYPE: PRT
```

-continued

```
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 269

Phe Xaa Ile Gly Arg Trp
1               5

<210> SEQ ID NO 270
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 270

Phe Xaa Ile Gly Arg Pro
1               5

<210> SEQ ID NO 271
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 271

Phe Xaa Ile Gly Arg Val
1               5

<210> SEQ ID NO 272
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 272

Phe Xaa Ile Gly His Leu
1               5

<210> SEQ ID NO 273
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 273

Phe Xaa Ile Gly Asp Leu
1               5
```

```
<210> SEQ ID NO 274
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 274

Phe Xaa Ile Gly Glu Leu
1               5

<210> SEQ ID NO 275
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 275

Phe Xaa Ile Gly Gln Leu
1               5

<210> SEQ ID NO 276
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 276

Phe Xaa Ile Gly Gly Leu
1               5

<210> SEQ ID NO 277
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 277

Phe Xaa Ile Gly Ala Leu
1               5

<210> SEQ ID NO 278
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine
```

```
<400> SEQUENCE: 278

Phe Xaa Ile Gly Phe Leu
1               5

<210> SEQ ID NO 279
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 279

Phe Xaa Ile Gly Lys Leu
1               5

<210> SEQ ID NO 280
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 280

Phe Xaa Ile Gly Leu Leu
1               5

<210> SEQ ID NO 281
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 281

Phe Xaa Ile Gly Met Leu
1               5

<210> SEQ ID NO 282
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 282

Phe Xaa Ile Gly Asn Leu
1               5

<210> SEQ ID NO 283
<211> LENGTH: 6
<212> TYPE: PRT
<213> ORGANISM: Unknown
<220> FEATURE:
```

```
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 283

Phe Xaa Ile Gly Ser Leu
1               5

<210> SEQ ID NO 284
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 284

Phe Xaa Ile Gly Tyr Leu
1               5

<210> SEQ ID NO 285
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 285

Phe Xaa Ile Gly Thr Leu
1               5

<210> SEQ ID NO 286
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 286

Phe Xaa Ile Gly Ile Leu
1               5

<210> SEQ ID NO 287
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 287

Phe Xaa Ile Gly Trp Leu
1               5
```

```
<210> SEQ ID NO 288
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 288

Phe Xaa Ile Gly Pro Leu
1               5

<210> SEQ ID NO 289
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 289

Phe Xaa Ile Gly Val Leu
1               5

<210> SEQ ID NO 290
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be N-allylglycine

<400> SEQUENCE: 290

Phe Xaa Ile Gly Arg Leu
1               5

<210> SEQ ID NO 291
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 291

Phe Xaa Tyr Gly Arg Leu
1               5

<210> SEQ ID NO 292
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 292
```

Phe Xaa His Gly Arg Leu
1               5

<210> SEQ ID NO 293
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 293

Phe Xaa Asn Gly Arg Leu
1               5

<210> SEQ ID NO 294
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 294

Phe Xaa Asp Gly Arg Leu
1               5

<210> SEQ ID NO 295
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 295

Phe Xaa Gln Gly Arg Leu
1               5

<210> SEQ ID NO 296
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 296

Phe Xaa Glu Gly Arg Leu
1               5

<210> SEQ ID NO 297
<211> LENGTH: 6
<212> TYPE: PRT
<213> ORGANISM: Unknown
<220> FEATURE:
<223> OTHER INFORMATION: Tight junction agonist peptide
<220> FEATURE:

<221> NAME/KEY: misc_feature
<222> LOCATION: (2)..(2)
<223> OTHER INFORMATION: Xaa may be L-allylglycine

<400> SEQUENCE: 297

Phe Xaa Lys Gly Arg Leu
1               5

<210> SEQ ID NO 298
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 298

Phe Xaa Arg Gly Arg Leu
1               5

<210> SEQ ID NO 299
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 299

Phe Xaa Ile Arg Arg Leu
1               5

<210> SEQ ID NO 300
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 300

Phe Xaa Ile Asn Arg Leu
1               5

<210> SEQ ID NO 301
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 301

Phe Xaa Ile His Arg Leu
1               5

<210> SEQ ID NO 302
<211> LENGTH: 6

-continued

```
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 302

Phe Xaa Ile Lys Arg Leu
1               5

<210> SEQ ID NO 303
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 303

Phe Xaa Ile Gln Arg Leu
1               5

<210> SEQ ID NO 304
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 304

Phe Xaa Ile Phe Arg Leu
1               5

<210> SEQ ID NO 305
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 305

Phe Xaa Ile Ser Arg Leu
1               5

<210> SEQ ID NO 306
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 306

Phe Xaa Ile Val Arg Leu
```

```
<210> SEQ ID NO 307
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 307

Phe Xaa Ile Asp Arg Leu
1               5

<210> SEQ ID NO 308
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be L-allylglycine

<400> SEQUENCE: 308

Phe Xaa Ile Glu Arg Leu
1               5

<210> SEQ ID NO 309
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be N-allylglycine

<400> SEQUENCE: 309

Phe Xaa Ile Gly Arg
1               5

<210> SEQ ID NO 310
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (2)..(2)
<223> OTHER INFORMATION: Xaa may be N-allylglycine

<400> SEQUENCE: 310

Phe Xaa Ile Gly Arg Leu
1               5

<210> SEQ ID NO 311
<211> LENGTH: 5
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(1)
```

-continued

```
<223> OTHER INFORMATION: Xaa may be benzyl-allylglycine

<400> SEQUENCE: 311

Xaa Ile Gly Arg Leu
1               5

<210> SEQ ID NO 312
<211> LENGTH: 6
<212> TYPE: PRT
<213> ORGANISM: Unknown
<220> FEATURE:
<223> OTHER INFORMATION: Tight junction agonist peptide
<220> FEATURE:
<221> NAME/KEY: misc_feature
<222> LOCATION: (1)..(6)
<223> OTHER INFORMATION: peptide may be cyclical
<220> FEATURE:
<221> NAME/KEY: misc_feature
<222> LOCATION: (2)..(2)
<223> OTHER INFORMATION: Xaa may be L-allylglycine

<400> SEQUENCE: 312

Phe Xaa Ile Gly Arg Leu
1               5

<210> SEQ ID NO 313
<211> LENGTH: 6
<212> TYPE: PRT
<213> ORGANISM: Unknown
<220> FEATURE:
<223> OTHER INFORMATION: Tight junction agonist peptide

<400> SEQUENCE: 313

Gly Phe Gly Ile Leu Arg
1               5

<210> SEQ ID NO 314
<211> LENGTH: 6
<212> TYPE: PRT
<213> ORGANISM: Unknown
<220> FEATURE:
<223> OTHER INFORMATION: Tight junction agonist peptide

<400> SEQUENCE: 314

Ile Gly Phe Leu Arg Gly
1               5
```